US010487161B2

(12) United States Patent
Canich et al.

(10) Patent No.: US 10,487,161 B2
(45) Date of Patent: Nov. 26, 2019

(54) CYCLOPROPYL SUBSTITUTED METALLOCENE CATALYSTS

(71) Applicant: ExxonMobil Chemical Patents Inc., Baytown, TX (US)

(72) Inventors: Jo Ann M. Canich, Houston, TX (US); Alexander Z. Voskoboynikov, Moscow (RU); Dmitry V. Uborsky, Moscow (RU); Ilya S. Borisov, Moscow (RU); Alexey A. Tsarev, Moscow (RU); Pavel S. Kulyabin, Moscow (RU); Mikhail I. Sharikov, Moscow (RU); Oleg V. Samsonov, Moscow (RU); Georgy P. Goryunov, Moscow (RU)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/798,945

(22) Filed: Oct. 31, 2017

(65) Prior Publication Data
US 2018/0066083 A1 Mar. 8, 2018

Related U.S. Application Data

(62) Division of application No. 14/324,427, filed on Jul. 7, 2014, now Pat. No. 9,834,628.

(60) Provisional application No. 61/847,464, filed on Jul. 17, 2013.

(51) Int. Cl.
C07F 17/00 (2006.01)
C08F 4/6592 (2006.01)
C08F 110/06 (2006.01)
C08F 10/02 (2006.01)
C08F 2/00 (2006.01)
C08F 4/659 (2006.01)

(52) U.S. Cl.
CPC ............ C08F 110/06 (2013.01); C07F 17/00 (2013.01); C08F 2/00 (2013.01); C08F 4/65925 (2013.01); C08F 4/65927 (2013.01); C08F 10/02 (2013.01); C08F 4/65908 (2013.01); C08F 4/65912 (2013.01); C08F 2420/02 (2013.01)

(58) Field of Classification Search
CPC ................................ C07F 17/00; C08F 4/6592
See application file for complete search history.

(56) References Cited

U.S. PATENT DOCUMENTS

| 4,814,540 A | 3/1989 | Watanabe et al. |
| 5,049,535 A | 9/1991 | Resconi et al. |
| 5,276,208 A | 1/1994 | Winter et al. |
| 5,278,264 A | 1/1994 | Spaleck et al. |
| 5,304,614 A | 4/1994 | Winter et al. |
| 5,459,117 A | 10/1995 | Ewen |
| 5,532,396 A | 7/1996 | Winter et al. |
| 5,543,373 A | 8/1996 | Winter et al. |
| 5,585,509 A | 12/1996 | Langhauser et al. |
| 5,631,202 A | 5/1997 | Ewen |
| 5,677,408 A | 10/1997 | Ueda et al. |
| 5,696,045 A | 12/1997 | Winter et al. |
| 5,700,886 A | 12/1997 | Winter et al. |
| 5,739,366 A | 4/1998 | Imuta et al. |
| 5,767,033 A | 6/1998 | Imuta et al. |
| 5,770,753 A | 6/1998 | Kuber et al. |
| 5,786,432 A | 7/1998 | Kuber et al. |
| 5,840,644 A | 11/1998 | Kuber et al. |
| 5,869,584 A | 2/1999 | Winter et al. |
| 6,051,727 A | 4/2000 | Kuber et al. |
| 6,057,408 A | 5/2000 | Winter et al. |
| 6,121,182 A | 9/2000 | Okumura et al. |
| 6,136,743 A | 10/2000 | Sugimura et al. |
| 6,150,481 A | 11/2000 | Winter et al. |
| 6,242,544 B1 | 6/2001 | Kuber et al. |
| 6,255,506 B1 | 7/2001 | Kuber et al. |
| 6,355,819 B1 | 3/2002 | Leino et al. |
| 6,380,331 B1 | 4/2002 | Kuchta et al. |
| 6,399,533 B2 | 6/2002 | Sacchetti et al. |
| 6,444,833 B1 | 9/2002 | Ewen et al. |
| 6,492,465 B1 | 12/2002 | Burkhardt et al. |
| 6,559,252 B1 | 5/2003 | Horton et al. |
| 6,608,224 B2 | 8/2003 | Resconi et al. |
| 6,635,779 B1 | 10/2003 | Ewen et al. |
| 6,730,754 B2 | 5/2004 | Resconi et al. |
| 6,787,618 B1 | 9/2004 | Winter et al. |
| 6,841,501 B2 | 1/2005 | Resconi et al. |
| 6,878,786 B2 | 4/2005 | Resconi et al. |
| 6,949,614 B1 | 9/2005 | Schottek |
| 6,953,829 B2 | 10/2005 | Kratzer et al. |
| 6,995,279 B2 | 2/2006 | Ushioda et al. |
| 7,034,173 B2 | 4/2006 | Schottek |
| 7,119,206 B2 | 10/2006 | Wallace |
| 7,122,498 B2 | 10/2006 | Hart et al. |

(Continued)

FOREIGN PATENT DOCUMENTS

CN 101074276 11/2007
DE 10335341 4/2004

(Continued)

OTHER PUBLICATIONS

U.S. Appl. No. 14/324,314, filed Jul. 7, 2014 Yang et al.
Kaneyoshi, H. et al., "Synthesis of Block and Graft Copolymers with Linear Polyethylene Segments by Combination of Degenerative Transfer Coordination Polymerization and Atom Transfer Radical Polymerization," Macromolecules, vol. 38, Issue 13, 2005, pp. 5425-5435.
Mochalov et al., "Transformations of Arylcyclopropanes Under the Action of Dinitrogen Tetroxide", Journal of Organic Chemistry of the USSR (Translation of Zhurnal Organicheskoi Khimii) (1998), vol. 34, Issue 9, pp. 1322-1330.

(Continued)

Primary Examiner — Caixia Lu

(57) ABSTRACT

This invention relates to a novel group 2, 3 or 4 transition metal metallocene catalyst compound having at least one arenyl ligand substituted with: 1) a cyclopropyl group and, optionally, 2) at least one other group, such as a hydrocarbyl, a heteroatom or a heteroatom containing group.

42 Claims, No Drawings

(56) References Cited

U.S. PATENT DOCUMENTS

| | | |
|---|---|---|
| 7,141,527 B1 | 11/2006 | Van Baar et al. |
| 7,220,695 B2 | 5/2007 | Casty et al. |
| 7,314,903 B2 | 1/2008 | Resconi et al. |
| 7,342,078 B2 | 3/2008 | Schottek et al. |
| 7,385,015 B2 | 6/2008 | Holtcamp |
| 7,393,965 B2 | 7/2008 | Tohi et al. |
| 7,405,261 B2 | 7/2008 | Schulte et al. |
| 7,452,949 B2 | 11/2008 | Okumura et al. |
| 7,569,651 B2 | 8/2009 | Schottek et al. |
| 7,601,666 B2 | 10/2009 | Rix et al. |
| 7,615,597 B2 | 11/2009 | Resconi et al. |
| 7,741,417 B2 | 6/2010 | Casty et al. |
| 7,799,880 B2 | 9/2010 | Ciaccia |
| 7,829,495 B2 | 11/2010 | Floyd et al. |
| 7,964,679 B2 | 6/2011 | Resconi et al. |
| 7,985,799 B2 | 7/2011 | Resconi et al. |
| 8,008,653 B2 | 8/2011 | Lee et al. |
| 8,222,356 B2 | 7/2012 | Kipke et al. |
| 2002/0103312 A1 | 8/2002 | Rausch et al. |
| 2003/0120015 A1 | 6/2003 | Resconi et al. |
| 2003/0149199 A1 | 8/2003 | Schottek et al. |
| 2003/0199703 A1 | 10/2003 | Schulte et al. |
| 2004/0127731 A1 | 7/2004 | Ushioda et al. |
| 2004/0132933 A1 | 7/2004 | Crowther et al. |
| 2004/0132935 A1 | 7/2004 | Arjunan et al. |
| 2005/0182266 A1 | 8/2005 | Schulte et al. |
| 2005/0228155 A1 | 10/2005 | Kawai et al. |
| 2005/0261449 A1 | 11/2005 | Voskoboynikov et al. |
| 2006/0116490 A1 | 6/2006 | Paczkowski et al. |
| 2009/0259007 A1 | 10/2009 | Ciaccia |
| 2010/0249346 A1 | 9/2010 | Schiendorfer et al. |
| 2010/0261860 A1 | 10/2010 | Schulte et al. |
| 2010/0267907 A1 | 10/2010 | Dimeska et al. |
| 2011/0230630 A1 | 9/2011 | Sell et al. |
| 2012/0095157 A1 | 9/2012 | Jiang et al. |
| 2013/0085232 A1 | 4/2013 | Stewart |
| 2013/0150541 A1 | 6/2013 | Crowther et al. |
| 2016/0161013 A1 | 6/2016 | Brooks et al. |

FOREIGN PATENT DOCUMENTS

| | | |
|---|---|---|
| DE | 10258968 | 7/2004 |
| EP | 0576970 | 1/1994 |
| EP | 812854 | 12/1997 |
| EP | 1209165 | 5/2002 |
| EP | 1520863 | 4/2005 |
| EP | 1548018 | 6/2005 |
| EP | 2360163 | 8/2011 |
| JP | 53-37644 | 4/1978 |
| JP | 53037644 | 4/1978 |
| JP | 55-10599 | 3/1980 |
| JP | 1996-239416 | 9/1996 |
| JP | 2003-064115 | 3/2003 |
| RU | 2160276 | 12/2000 |
| WO | 1996/22995 | 8/1996 |
| WO | 97/40075 | 10/1997 |
| WO | 98/46616 | 10/1998 |
| WO | 2000/068279 | 11/2000 |
| WO | 01/48034 | 7/2001 |
| WO | 02/02575 | 1/2002 |
| WO | 02/02576 | 1/2002 |
| WO | 2002/18397 | 3/2002 |
| WO | 03/002583 | 1/2003 |
| WO | 03/045551 | 6/2003 |
| WO | 2003/050131 | 6/2003 |
| WO | 2004/017602 | 2/2004 |
| WO | 2004/106351 | 12/2004 |
| WO | 07/070040 | 6/2007 |
| WO | 2008/027116 | 3/2008 |
| WO | 2009/054832 | 4/2009 |
| WO | 2009/054833 | 4/2009 |
| WO | 2010/077230 | 7/2010 |
| WO | 2011/051705 | 5/2011 |
| WO | 2012/134715 | 10/2012 |
| WO | 2015/009479 | 1/2015 |

OTHER PUBLICATIONS

De Meijere et al., "An Efficient Three-Step Synthesis of Cyclpenta[b]pyrans via 2-Donor-Substituted Fischer Ethenylcarbenechromium Complexes", Chemistry: A European Journal, 2005, Wiley-VCH Verlag GmbH & Co. KGaA, Weinheim, vol. 11, pp. 4132-4148.

Izmer et al., "Synthesis and Molecular Structures of Zirconium and Hafnium Complexes Bearing Dimethylsilandiyl-bis-2,4,6-trimethylindenyl and Dimethylsilandiyl-bis-2-methyl-4,6-diisopropylindenyl Ligands", Journal of Organometallic Chemistry (2005), vol. 690, Issue 4, pp. 1067-1079.

Riemschneider et al., "Chemistry of Polyhalocyclopentadienes and Related Compounds. XVII. Reaction of Hexachlorocyclopentadiene with Unsaturated Compounds", Monatshefte fuer Chemie, 1960, vol. 91, Issue 1, pp. 22-40. (English language abstract attached.).

Rulhoff et al., "Synthesis and Characterization of Propylene and Linear Ethylene Oligomers (Cn=26-28) with Metallocenes/MAO Catalysts," Macromolecular Chemistry and Physics, vol. 207, Issue 16, 2006, pp. 1450-1460.

Mochalov et al., "Nitration of Biphenylcyclopropanes", Journal of Organic Chemistry of the USSR (Zhurnal Organicheskoi Khimii), May 1976, vol. 12, Issue 5, pp. 1008-1014.

Ransom et al., "Synthesis and Molecular Structures of Zirconium and Hafnium Complexes Bearing Dimethylsilandiyl-bis-2,4,6-trimethylindenyl and Dimethylsilandiyl-bis-2-methyl-4,6-diisopropylindenyl Ligands", Organometallics (2011), vol. 30, Issue 4, pp. 800-814.

Caldwell et al., "Are Perpendicular Alkene Triplets Just 1,2-Biradicals? Studies with the Cyclopropylcarbinyl Clock", Journal of the American Chemical Society, Mar. 1994, vol. 116, No. 6, pp. 2271-2275.

Deng et al., "Nickel-catalyzed Carboannulation Reaction of o-Bromobenzyl Zinc Bromide with Unsaturated Compounds", Organic Letters, 2007, vol. 9, No. 25, pp. 5207-5210.

Shabarov et al., "Reaction of 2-cyclpropylfluorene with Mercury Acetate", Vestnik Moskovskogo Universiteta, Seriya 2: Khimiya, Moscow University Chemistry Bulletin, 1976, vol. 17, Issue 5, pp. 620-621.

Yoshida, Z., "Novel Pi Systems Possessing Cyclopropenylidene Moiety", Pure & Applied Chemistry, vol. 54, No. 5 (1982), pp. 1059-1074.

Waugh et al., "Upper Excited State Photochemistry: Solution and Gas Phase Photochemistry and Photophysics of 2- and 3-Cyclopropylindene1", Journal of the American Chemical Society, Mar. 1999, vol. 121, Issue 13, pp. 3083-3092.

De Boer et al., "Phospholyl Catalysts for Olefin Polymerization", Journal, of Molecular Catalysis A; Chemical, 1998, vol. 128, pp. 155-165.

Hanlan et al., "Chemistry via Metal Atom Cocondensation: Isomerization and Complexation Reactions of Organocyclopropanes and Spirocycles", Inorg. Chem., 1980, vol. 19, No. 6, pp. 1543-1551.

Kolesnikov et al., Synthesis of Cyclopropyl-Containing Bisarene Complexes of Titanium and Chromium, Bulletin of the Academy of Sciences of the USSR, Division of Chemical Science, 1981, No. 2, pp. 376-378.

Resconi et al., "Olefin Polymerization of Bis(pentamethylcyclopentadienyl)zirconium and -hafnium Centers: Chain-Transfer Mechanisms", Journal of Am. Chem. Soc., 1992, vol. 14, No. 3, pp. 1025-1032.

Schobel et al., "Ultra-Rigid Metallocenes for Highly Iso- and Regiospecific Polymerization of Propene: The Search for the Perfect Polypropylene Helix", Chemistry, A European Journal, 2012, vol. 18, pp. 4174-4178.

CYCLOPROPYL SUBSTITUTED METALLOCENE CATALYSTS

PRIORITY

This application is a divisional of U.S. Ser. No. 14/324,427, filed Jul. 7, 2014, which claims the benefit of and priority to U.S. Provisional Application No. 61/847,464, filed Jul. 17, 2013, the disclosure of which is fully incorporated herein by reference.

FIELD OF THE INVENTION

This invention relates to novel metallocene compounds and metallocene catalyst systems comprising at least one cyclopropyl substituted indenyl group and uses thereof.

BACKGROUND OF THE INVENTION

Olefin polymerization catalysts are of great use in industry. Hence, there is interest in finding new catalyst systems that increase the commercial usefulness of the catalyst and allow the production of polymers having improved properties.

Catalysts for olefin polymerization are often based on metallocenes as catalyst precursors, which are activated either with an alumoxane or with an activator containing a non-coordinating anion.

Cyclopropyl substituted arenyl complexes are relatively unknown and there are no known early transition metal complexes containing a cyclopropyl substituted arenyl ligand. As a result there are no known early transition metal olefin polymerization catalysts bearing a cyclopropyl substituted arenyl ligand, and in particular, a cyclopropyl substituted indenyl ligand.

Cyclopropyl cyclopentadiene is reported in "Chemistry of Polyhalocyclo-pentadienes and related compounds: XVII Reaction of Hexachlorocyclopentadiene with unsaturated compounds," Reimschneider, R. et al, Monatshefte Fuer Chemie (1960).

2-Cyclopropyl indene is disclosed in: 1) "Nickle Catalyzed Carboannulation Reaction of o-Bromobenzyl Zinc Bromide with Unsaturated Compounds," Deng, Ruixue, et al., Organic Letters (2007) 9(25) pp. 5207-5210; and 2) "Are Perpendicular Alkene Triplets Just 1,2 Biradicals? Studies with the Cyclopropylcarbinyl Clock," Caldwell, Richard A. et al., Journals of the American Chemical Society (1994) 116(6), pp. 2271-2275.

1- and 3-cyclopropyl indene are disclosed in reference to the photolysis of 2-cyclopropyl indene (and have not been prepared in large scale) in "Upper Excited State Photochemistry: Solution and Gas Phase Photochemistry and Photophysics of 2- and 3-Cyclopropylindene", Waugh, Tim; Morrison, Harry; Journal of the American Chemical Society (1999), 121(13), pp. 3083-3092.

Cyclopropyl substituted fluorenyls are disclosed in "Transformations of arylcyclopropanes under the action of dinitrogen tetroxide" Mochalov, S. S.; Kuz'min, Ya. I.; Fedotov, A. N.; Trofimova, E. V.; Gazzaeva, R. A.; Shabarov, Y. S.; Zefirov, N. S., Russian Journal of Organic Chemistry (Translation of Zhurnal Organicheskoi Khimii) (1998), 34(9), pp. 1322-1330, MAIK Nauka/Interperiodica Publishing.

2-Cyclopropylfluorene is disclosed in the abstract of "Reaction of 2-cyclopropylfluorene with mercury acetate," Shabarov, Yu. S.; Bandaev, S. G.; Sychkova, L. D., Vestnik Moskovskogo Universiteta, Seriya 2: Khimiya, (1976), 17(5), pp. 620-1.

Nitration of 2-cyclopropylbiphenyl is disclosed in "Nitration of biphenylcyclopropanes" Mochalov, S. S.; Novokreshchennykh, V. D.; Shabarov, Yu. S., Zhurnal Organicheskoi Khimii (1976), 12(5), pp. 1008-14.

Other references of interest include: 1) "An efficient three-step synthesis of cyclopenta[b]pyrans via 2-donor-substituted Fischer ethenylcarbenechromium complexes," de Meijere, Armin; Schirmer, Heiko; Stein, Frank; Funke, Frank; Duetsch, Michael; Wu, Yao-Ting; Noltemeyer, Mathias; Belgardt, Thomas; Knieriem, Burkhard, Chemistry—A European Journal (2005), 11(14), pp. 4132-4148; 2) "Novel Pi Systems Possessing Cyclopropenylidene Moiety," Yoshida, Zenichi, Pure and Applied Chemistry (1982), 54(5), pp. 1059-74; 3) JP 55-010596 B (1980); 4) "An efficient three-step synthesis of cyclopenta[b]pyrans via 2-donor-substituted Fischer ethenylcarbene-chromium complexes," de Meijere, Armin; Schirmer, Heiko; Stein, Frank; Funke, Frank; Duetsch, Michael; Wu, Yao-Ting; Noltemeyer, Mathias; Belgardt, Thomas; Knieriem, Burkhard, Chemistry—A European Journal (2005), 11(14), pp. 4132-4148; and 5) "Novel Pi Systems Possessing Cyclopropenylidene Moiety," Yoshida, Zenichi, Pure and Applied Chemistry (1982), 54(5), pp. 1059-74.

U.S. Pat. No. 7,829,495 discloses alkyl substituted metallocenes having a " . . . $C_3$ or greater hydrocarbyl . . . substitutent bonded to either the $L^A$ or $L^B$ ring through a primary carbon atom . . . preferably an n-alkyl substituent . . . " (see column 4, lines 9-12). Further, in the Examples section, (n-propylcyclopentadienyl)(tetramethylcyclopentadienyl)zirconium dichloride combined with methylalumoxane and Davision™ 948 silica is used for ethylene hexene polymerization; bis(n-propyl cyclopentadienyl) zirconium dichloride combined with methylalumoxane and Davision™ 948 silica is used for ethylene hexene polymerization; and dimethylsilyl(flourenyl)(n-propyl cyclopentadienyl) zirconium dichloride combined with methylalumoxane and Davision silica is used for ethylene hexene polymerization.

Other references of interest include U.S. Pat. Nos. 6,051,727, 6,255,506, EP 0 576 970, U.S. Pat. Nos. 5,459,117, 5,532,396, 5,543,373, 5,585,509, 5,631,202, 5,696,045, 5,700,886, 6,492,465, 6,150,481, 5,770,753, 5,786,432, 5,840,644, 6,242,544, 5,869,584, 6,399,533, 6,444,833, 6,559,252, 6,608,224, 6,635,779, 6,841,501, 6,878,786, 6,949,614, 6,953,829, 7,034,173, 7,141,527, 7,314,903, 7,342,078, 7,405,261, 7,452,949 7,569,651, 7,615,597, 7,799,880, 7,964,679, 7,985,799, 8,222,356, 5,278,264, 5,276,208, 5,049,535, US2011/0230630, WO 02/022576, WO 02/022575, WO 2003/002583, U.S. Pat. No. 7,122,498, US 2011/0230630, US 2010/0267907, EP 1 250 365, WO 97/9740075 and WO 03/045551.

There is still a need in the art for new and improved catalyst systems for the polymerization of olefins, in order to achieve specific polymer properties, such as high melting point, high molecular weights, to increase conversion or comonomer incorporation, or to alter comonomer distribution without deteriorating the resulting polymer's properties.

It is therefore an object of the present invention to provide novel catalyst compounds, catalysts systems comprising such compounds, and processes for the polymerization of olefins using such compounds and systems.

SUMMARY OF THE INVENTION

This invention relates to a novel group 3, 4 or 5 transition metal metallocene catalyst compound having at least one arenyl ligand substituted with a cyclopropyl group.

This invention also relates to a novel group 3, 4 or 5 transition metal metallocene catalyst compound having at least one arenyl ligand substituted with: 1) a cyclopropyl group and 2) at least one other group, such as a substituted or unsubstituted hydrocarbyl group.

This invention further relates to a metallocene compound represented by the formula (1):

$A_e MX_{n-e}$ wherein:

e is 1 or 2; each A is a substituted monocyclic or polycyclic ligand that is pi-bonded to M and optionally includes one or more ring heteroatoms selected from boron, a group 14 atom that is not carbon, a group 15 atom, or a group 16 atom, and when e is 2, each A may be the same or different;

provided that at least one A is substituted with at least one cyclopropyl substituent directly bonded to any $sp^2$ carbon atom at a bondable ring position of the ligand, wherein the cyclopropyl substituent is represented by the formula:

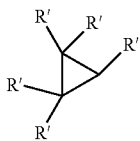

where each R' is, independently, hydrogen, a substituted or unsubstituted hydrocarbyl group, or a halogen; M is a transition metal atom having a coordination number of n and selected from group 3, 4, or 5 of the Periodic Table of Elements, or a lanthanide metal atom, or actinide metal atom; n is 3, 4, or 5; and each X is a univalent anionic ligand, or two Xs are joined and bound to the metal atom to form a metallocycle ring, or two Xs are joined to form a chelating ligand, a diene ligand, or an alkylidene ligand.

This invention further relates to a metallocene compound represented by one of the following formulae:

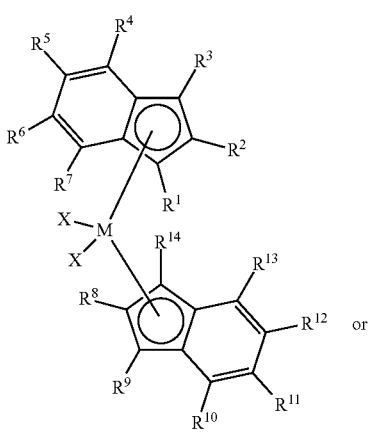

formula (1a)

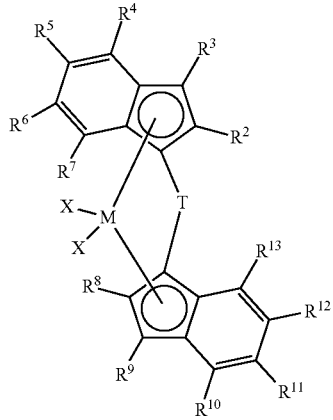

formula (1b)

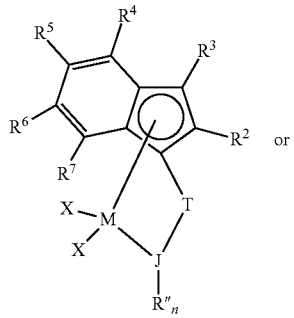

formula (2a)

or

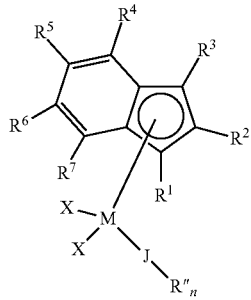

formula (2b)

wherein:
M is a transition metal atom selected from group 3, 4, or 5 of the Periodic Table of Elements;
T is a bridging group;
each X is a univalent anionic ligand, or two Xs are joined and bound to the metal atom to form a metallocycle ring, or two Xs are joined to form a chelating ligand, a diene ligand, or an alkylidene ligand;
each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is, independently, hydrogen, a substituted hydrocarbyl group, an unsubstituted hydrocarbyl group, or a halide, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is a cyclopropyl substituent;
provided that any adjacent $R^1$ to $R^{14}$ groups that are not a cyclopropyl substituent may form a fused ring or multi-center fused ring system where the rings may be aromatic, partially saturated or saturated;
J is a heteroatom with a coordination number of three from group 15 or with a coordination number of two from group 16 of the Periodic Table of Elements;
R" is a $C_1$-$C_{100}$ substituted or unsubstituted hydrocarbyl radical; and n is 0, 1 or 2 and n represents the number of R" substituents, and n is one when J is a group 15 heteroatom and T is present, or a group 16 heteroatom and T is absent; n is two when J is a group 15 heteroatom and T is absent; n is zero when J is a group 16 heteroatom and T is present.

This invention further relates to a metallocene compound represented by the formula (2):

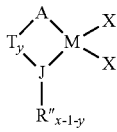

wherein:

M is a group 3, 4, or 5 transition metal atom, or a lanthanide metal atom, or actinide metal atom;

A is a substituted monocyclic or polycyclic ligand that is pi-bonded to M and is substituted with at least one cyclopropyl substituent directly bonded to any $sp^2$ carbon atom at a bondable ring position of the ligand; and wherein the cyclopropyl substituent is represented by the formula:

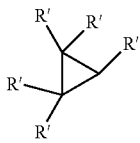

wherein each R' is, independently, hydrogen, a substituted hydrocarbyl group, an unsubstituted hydrocarbyl group, or a halogen;

T is an optional bridging group that is bonded to A and J, and is present when y is one and absent when y is zero;

y is zero or one;

J is a heteroatom with a coordination number of three from group 15 or with a coordination number of two from group 16 of the Periodic Table of Elements;

R" is a $C_1$-$C_{100}$ substituted or unsubstituted hydrocarbyl radical;

x is the coordination number of the heteroatom J where "x-1-y" indicates the number of R" substituents bonded to J; and each X is a univalent anionic ligand, or two Xs are joined and bound to the metal atom to form a metallocycle ring, or two Xs are joined to form a chelating ligand, a diene ligand, or an alkylidene ligand.

This invention further relates to a metallocene compound represented by the formula (3):

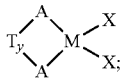

wherein:

M is a group 4 transition metal atom, or a lanthanide metal atom, or actinide metal atom;

each A is, independently, a substituted or unsubstituted monocyclic or polycyclic ligand pi-bonded to M, and optionally includes one or more ring heteroatoms selected from boron, a group 14 atom that is not carbon, a group 15 atom, or a group 16 atom, and each A may be the same or different, provided that at least one A is substituted with at least one cyclopropyl substituent directly bonded to any $sp^2$ carbon atom at a bondable ring position of the ligand;

T is an optional bridging group that is bonded to each A, and is present when y is one and absent when y is zero;

y is zero or one; and each X is a univalent anionic ligand, or two X are joined and bound to the metal atom to form a metallocycle ring, or two X are joined to form a chelating ligand, a diene ligand, or an alkylidene ligand.

This invention further relates to a catalyst system comprising said metallocene catalyst compound(s) and an activator.

This invention further relates to a method to polymerize olefins comprising contacting olefins with a catalyst system comprising said metallocene catalyst compound(s) described above and an activator.

This invention also relates to a method to prepare said metallocene catalyst compound(s).

This invention further relates to polymer compositions produced by the methods described herein.

DEFINITIONS

As used herein, the numbering scheme for the Periodic Table Groups is the new notation as set out in CHEMICAL AND ENGINEERING NEWS, 63(5), 27 (1985). Therefore, a "group 4 metal" is an element from group 4 of the Periodic Table, e.g. Zr, Ti, and Hf.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be a radical, which contains hydrogen atoms and up to 100 carbon atoms and which may be linear, branched, or cyclic, and when cyclic, aromatic or non-aromatic.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)₂—, —Ge(R*)₂—, —Sn(R*)₂—, —Pb(R*)₂— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include SiH₃, SiH₂R*, SiHR*₂, SiR*₃, SiH₂(OR*), SiH(OR*)₂, Si(OR*)₃, SiH₂(NR*₂), SiH(NR*₂)₂, Si(NR*₂)₃, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include GeH₃, GeH₂R*, GeHR*₂, GeR*₃, GeH₂(OR*), GeH(OR*)₂, Ge(OR*)₃, GeH₂(NR*₂), GeH(NR*₂)₂, Ge(NR*₂)₃, and the like where R* is independently a hydrocarbyl or halocarbyl radical and two or more R* may join together to form a substituted or unsubstituted saturated, partially unsaturated or aromatic cyclic or polycyclic ring structure.

Polar radicals or polar groups are groups in which a heteroatom functionality is bonded directly to the indicated atom or atoms. They include heteroatoms of Groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, sulfonates, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include NR*₂, OR*, SeR*, TeR*, PR*₂, AsR*₂, SbR*₂, SR*, BR*₂, SnR*₃, PbR*₃ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure. Also preferred are sulfonate radicals, S(=O)₂OR*, where R* is defined as above. Examples include SO₃Me (mesylate), SO₃(4-tosyl) (tosylate), SO₃CF₃ (triflate), SO₃(n-C₄F₉) (nonaflate) and the like.

In using the terms "substituted or unsubstituted cyclopentadienyl ligand", "substituted or unsubstituted indenyl ligand", "substituted or unsubstituted fluorenyl ligand", "substituted or unsubstituted cyclopentanaphthyl ligand", "substituted or unsubstituted monocyclic arenyl ligand", or "substituted or unsubstituted polycyclic arenyl ligand", the substitution to the aforementioned ligand is on a bondable ring position, and each occurrence is selected from hydrocarbyl, substituted hydrocarbyl, halocarbyl, substituted halocarbyl, silylcarbyl, germylcarbyl, a halogen radical, or a polar group.

In some embodiments of the invention, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, butylphenyl, dibutylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For nomenclature purposes, the following numbering schemes are used for cyclopentadienyl, indenyl, fluorenyl, and cyclopentanaphthyl (also termed benzindenyl). It should be noted that indenyl can be considered a cyclopentadienyl with fused a benzene ring. Analogously, fluorenyl can be considered an indenyl with two phenyl rings fused onto the cyclopentadienyl ring. Each structure below is drawn and named as an anion.

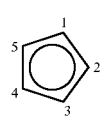 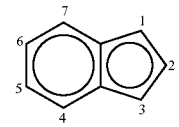

Cyclopentadienyl　　　Indenyl

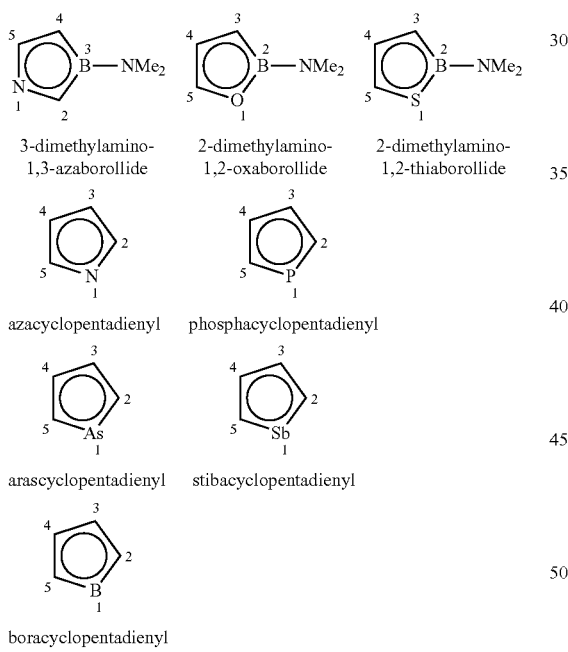

Fluorenyl cyclopenta[b]naphthyl cyclopenta[a]naphthyl

A similar numbering and nomenclature scheme is used for heterocyclopentadienyls, heterophenyls, heteropentalenyls, heterocyclopentapentalenyls, heteroindenyls, heterofluorenyls, heterocyclopentanaphthyls, heterocyclopentaindenyls, heterobenzocyclopentaindenyls, and the like, as illustrated below. Each structure is drawn and named as an anion.

Non-limiting examples of heterocyclopentadienyls include:

3-dimethylamino-1,3-azaborollide 2-dimethylamino-1,2-oxaborollide 2-dimethylamino-1,2-thiaborollide azacyclopentadienyl phosphacyclopentadienyl arascyclopentadienyl stibacyclopentadienyl boracyclopentadienyl Further non-limiting examples of heterocyclopentadienyls include 1,3-diazacyclopentadienyl, 1,3-diphosphacyclopentadienyl, 1,3-diarsacyclopentadienyl, 1,3-distibacyclopentadienyl, 1,3-diboracyclopentadienyl, 1,3-azaphosphacyclopentadienyl, 1,3-azaarsacylcopentadienyl, 1,3-azastibacyclopentadienyl, 1,3-azaboracyclopentadienyl, 1,3-arsaphosphacyclopentadienyl, 1,3-arsastibacyclopentadienyl, 1,3-arsaboracyclopentadienyl, 1,3-boraphosphacyclopentadienyl, 1,3-borastibacylcopentadienyl, 1,3-phosphastibacyclopentadienyl, 1,2-diazacyclopentadienyl, 1,2-diphosphacyclopentadienyl, 1,2-diarsacyclopentadienyl, 1,2-distibacyclopentadienyl, 1,2-diboracyclopentadienyl, 1,2-azaphosphacyclopentadienyl, 1,2-azaarsacylcopentadienyl, 1,2-azastibacyclopentadienyl, 1,2-azaboracyclopentadienyl, 1,2-arsaphosphacyclopentadienyl, 1,2-arsastibacyclopentadienyl, 1,2-arsaboracyclopentadienyl, 1,2-boraphosphacyclopentadienyl, 1,2-borastibacylcopentadienyl, 1,2-phosphastibacyclopentadienyl, 3-dihydrocarbylamino-1,3-azaborollide, 2-dihydrocarbylamino-1,2-oxaborollide, 2-dihydrocarbylamino-1,2-thiaborollide, 3-hydrocarbyloxy-1,3-azaborollide, 2-hydrocarbyloxy-1,2-oxaborollide, 2-hydrocarbyloxy-1,2-thiaborollide, 3-hydrocarbyl-1,3-azaborollide, 2-hydrocarbyl-1,2-oxaborollide, and 2-hydrocarbyl-1,2-thiaborollide, where hydrocarbyl is a "hydrocarbyl radical" as previously defined.

Non-limiting examples of heterophenyls include:

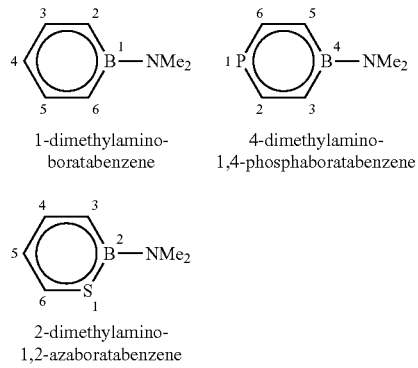

1-dimethylamino-boratabenzene 4-dimethylamino-1,4-phosphaboratabenzene 2-dimethylamino-1,2-azaboratabenzene Further non-limiting examples of heterophenyls include 1-dihydrocarbylaminoboratabenzene, 4-dihydrocarbylamino-1,4-phosphaboratabenzene, 2-dihydrocarbylamino-1,2-azaboratabenzene, 1-hydrocarbyloxyboratabenzene, 4-hydrocarbyloxy-1,4-phosphaboratabenzene, 2-hydrocarbyloxy-1,2-azaboratabenzene, 1-hydrocarbylboratabenzene, 4-hydrocarbyl-1,4-phosphaboratabenzene, and 2-hydrocarbyl-1,2-azaboratabenzene, where hydrocarbyl is a "hydrocarbyl radical" as previously defined.

Non-limiting examples of heteropentalenyls include:

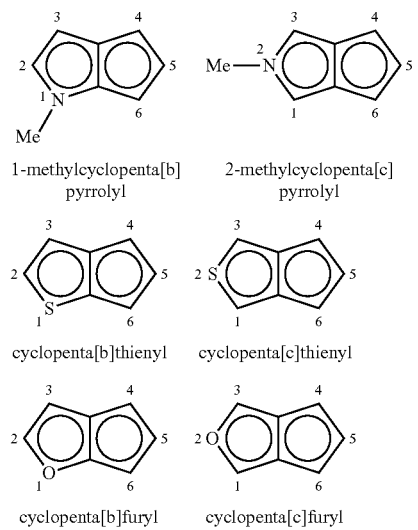

1-methylcyclopenta[b]pyrrolyl 2-methylcyclopenta[c]pyrrolyl cyclopenta[b]thienyl cyclopenta[c]thienyl cyclopenta[b]furyl cyclopenta[c]furyl -continued

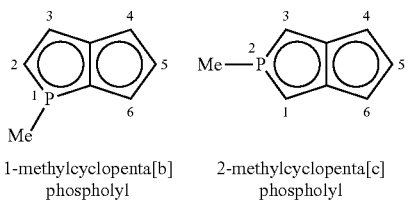

1-methylcyclopenta[b]phospholyl    2-methylcyclopenta[c]phospholyl

Further non-limiting examples of heteropentalenyls include cyclopenta[b]selenophenyl, cyclopenta[c]selenophenyl, cyclopenta[b]tellurophenyl, cyclopenta[c]tellurophenyl, 1-hydrocarbylcyclopenta[b]arsolyl, 2-hydrocarbylcyclopenta[c]arsolyl, 1-hydrocarbylcyclopenta[b]stibolyl, 2-hydrocarbylcyclopenta[c]stibolyl, 1-hydrocarbylcyclopenta[b]pyrrolyl, 2-hydrocarbylcyclopenta[c]pyrrolyl, 1-hydrocarbylcyclopenta[b]phospholyl, and 2-hydrocarbylcyclopenta[c]phospholyl, where hydrocarbyl is a "hydrocarbyl radical" as previously defined.

Non-limiting examples of heterocylopentapentalenyls include the following, where Z and Q independently represent the heteroatoms O, S, Se, or Te, or heteroatom groups, NR, PR, AsR, or SbR where R** is hydrogen, or a hydrocarbyl, substituted hydrocarbyl, halocarbyl, substituted halocarbyl, silylcarbyl, or germylcarbyl substituent.

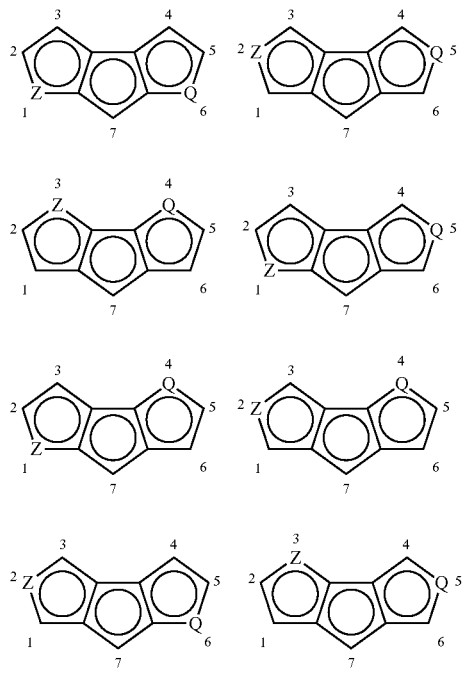

Non-limiting examples of heteroindenyls include:

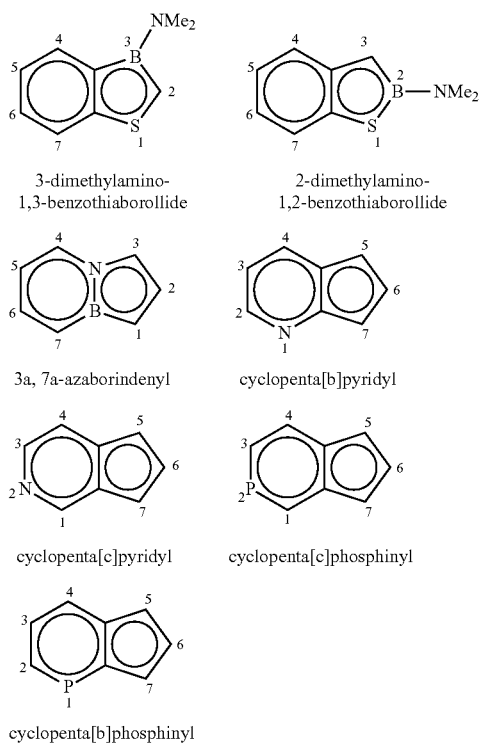

Further non-limiting examples of heteroindenyls include cyclopenta[b]arsinyl, cyclopenta[c]arsinyl, cyclopenta[b]stibinyl, cyclopenta[c]stibinyl, 3-dihydrocarbylamino-1,3-benzothiaborollide, 2-dihydrocarbylamino-1,2-benzothiaborollide, 3-hydrocarbyloxy-1,3-benzothiaborollide, 2-hydrocarbyloxy-1,2-benzothiaborollide, 3-hydrocarbyl-1,3-benzothiaborollide, and 2-hydrocarbyl-1,2-benzothiaborollide, where hydrocarbyl is a "hydrocarbyl radical" as previously defined.

Non-limiting examples of heterofluorenyls include:

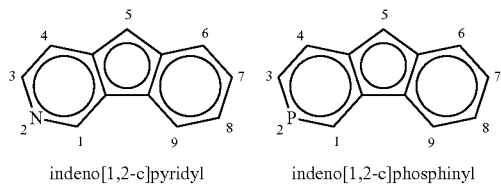

indeno[1,2-c]pyridyl    indeno[1,2-c]phosphinyl

Non-limiting examples of heterocyclopentanaphthyls include:

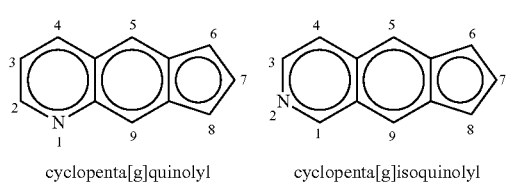

cyclopenta[g]quinolyl    cyclopenta[g]isoquinolyl

Further non-limiting examples of heterocyclopentanaphthyls include cyclopenta[g]phosphinolyl, cyclopenta[g]isophosphinolyl, cyclopenta[g]arsinolyl, and cyclopenta[g]isoarsinolyl.

Non-limiting examples of heterocyclopentaindenyls include:

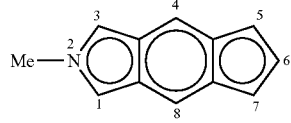

2-mthylcyclopenta[f]isoindolyl

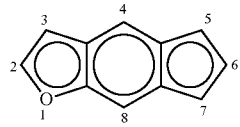

indeno[5,6-b]furyl

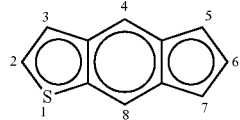

indeno[5,6-b]thienyl

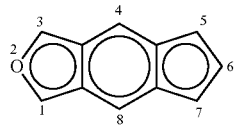

indeno[5,6-c]furyl

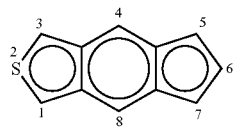

indeno[5,6-c]thienyl

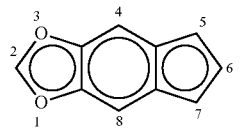

indeno[5,6-d]dioxolyl

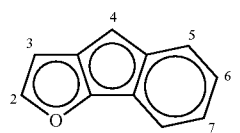

indeno[1,2-b]furyl

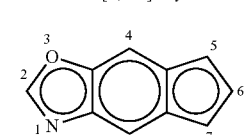

1-methylcyclopenta[f]indoyl

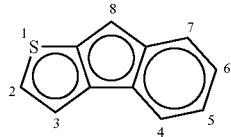

indeno[2,1-b]thienyl

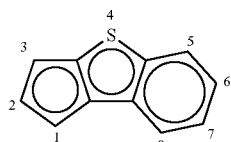

cyclopenta[b][1]benzothienyl

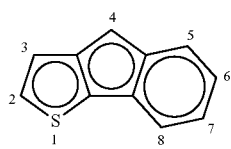

indeno[1,2-b]thienyl

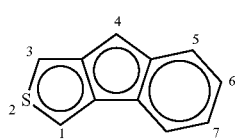

indeno[1,2-c]thienyl

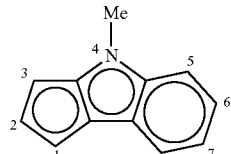

4-methylcyclopenta[b]indolyl

Further non-limiting examples of heterocyclopentaindenyls include 1-hydrocarbylcyclopenta[f]phosphindolyl, 2-hydrocarbylcyclopenta[f]isophosphindolyl, 1-hydrocarbylcyclopenta[f]arsindolyl, 2-hydrocarbylcyclopenta[f]isoarsindolyl, indeno[5,6-b]selenophenyl, indeno[5,6-b]tellurophenyl, indeno[5,6-c]selenophenyl, indeno[5,6-c]tellurophenyl, 2-hydrocarbylcyclopenta[f]isoindolyl, and 1-hydrocarbylcyclopenta[f]indolyl, where hydrocarbyl is a "hydrocarbyl radical" as previously defined.

Non-limiting examples of heterobenzocyclopentaindenyls include:

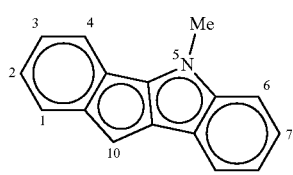

5-methylindeno[1,2-b]indolyl

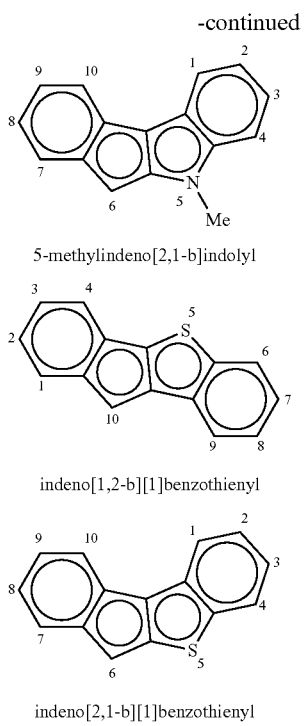

5-methylindeno[2,1-b]indolyl indeno[1,2-b][1]benzothienyl indeno[2,1-b][1]benzothienyl Further non-limiting examples of heterobenzocyclopentaindenyls include 5-hydrocarbylindeno[1,2-b]indolyl and 5-hydrocarbylindeno[2,1-b]indolyl, where hydrocarbyl is a "hydrocarbyl radical" as previously defined.

A "ring carbon atom" is a carbon atom that is part of a cyclic ring structure. By this definition, an indenyl fragment has nine ring carbon atoms. Whereas the monocyclic and polycyclic arene ligands described herein generally contain only ring carbon atoms, it is within the scope of the invention to replace one of more of the ring carbon atoms with a heteroatom, such as a boron atom, a Group 14 atom that is not carbon, a Group 15 atom, or a Group 16 atom. Preferred heteroatoms include boron, nitrogen, oxygen, phosphorus, and sulfur.

A "bondable ring position" is a ring position that is capable of bearing a substituent or bridging substituent. For example, indeno[5,6-c]thienyl has seven bondable ring positions (at the carbon atoms) and one non-bondable ring position (the sulfur atom).

The term "arenyl" ligand is used herein to mean an unsaturated cyclic hydrocarbyl ligand that can consist of one ring, or two or more fused or catenated rings.

As used herein, the term "monocyclic arenyl ligand" is used herein to mean a substituted or unsubstituted monoanionic $C_5$ to $C_{100}$ hydrocarbyl ligand that contains an aromatic five-membered single hydrocarbyl ring structure (also referred to as a cyclopentadienyl ring).

As used herein, the term "polycyclic arenyl ligand" is used herein to mean a substituted or unsubstituted monoanionic $C_8$ to $C_{103}$ hydrocarbyl ligand that contains an aromatic five-membered hydrocarbyl ring (also referred to as a cyclopentadienyl ring) that is fused to one or two partially unsaturated, or aromatic hydrocarbyl ring structures which may be fused to additional saturated, partially unsaturated, or aromatic hydrocarbyl rings.

Non-limiting examples of polycyclic arenyl ligands, named also as monoanionic ligands, include indenyl, 4,5-dihydroindenyl, 4,7-dihydroindenyl, 4,5,6,7-tetrahydroindenyl, fluorenyl, 1,2-dihydrotetrahydrofluorenyl, 1,4-dihydrotetrahydrofluorenyl, 3,4-dihydrotetrahydrofluorenyl, 1,2,3,4-tetrahydrofluorenyl, 1,2,5,6-tetrahydrofluorenyl, 1,2,7,8-tetrahydrofluorenyl, 3,4,5,6-tetrahydrofluorenyl, 1,4,5,8-tetrahydrofluorenyl, 1,2,3,4,5,6,7,8-octahydrofluorenyl, cyclopenta[b]naphthyl, 4,4a-dihydrocyclopenta[b]naphthyl, 5,6-dihydrocyclopenta[b]naphthyl, 5,8-dihydrocyclopenta[b]naphthyl, 4,9-dihydrocyclopenta[b]naphthyl, 4,4a,5,6-tetrahydrocyclopenta[b]naphthyl, 4,5,8,9-tetrahydrocyclopenta[b]naphthyl, 4,4a,7,8-tetrahydrocyclopenta[b]naphthyl, 4,4a,8a,9-tetrahydrocyclopenta[b]naphthyl, 5,6,7,8-tetrahydrocyclopenta[b]naphthyl, 4,4a,5,8-tetrahydrocyclopenta[b]naphthyl, 4,5,6,9-tetrahydrocyclopenta[b]naphthyl, 4,6,7,8-tetrahydrocyclopenta[b]naphthyl, 4,6,7,9-tetrahydrocyclopenta[b]naphthyl, 4,4a,5,9-tetrahydrocyclopenta[b]naphthyl, 4,4a,5,6,7,8-hexahydrocyclopenta[b]naphthyl, 4,4a,5,6,8a,9-hexahydrocyclopenta[b]naphthyl, 4,4a,5,8,8a,9-hexahydrocyclopenta[b]naphthyl, 4,5,6,7,8,9-hexahydrocyclopenta[b]naphthyl, 4,4a,5,6,7,9-hexahydrocyclopenta[b]naphthyl, 4,4a,5,6,7,8,8a,9-octahydrocyclopenta[b]naphthyl, cyclopenta[a]naphthyl, 4,5-dihydrocyclopenta[a]naphthyl, 6,7-dihydrocyclopenta[a]naphthyl, 8,9-dihydrocyclopenta[a]naphthyl, 5a,9a-dihydrocyclopenta[a]naphthyl, 6,9-dihydrocyclopenta[a]naphthyl, 7,9a-dihydrocyclopenta[a]naphthyl, 4,9a-dihydrocyclopenta[a]naphthyl, 5a,8-dihydrocyclopenta[a]naphthyl, 4,5,5a,9a-tetrahydrocyclopenta[a]naphthyl, 4,5,6,7-tetrahydrocyclopenta[a]naphthyl, 4,5,8,9-tetrahydrocyclopenta[a]naphthyl, 5a,6,7,9a-tetrahydrocyclopenta[a]naphthyl, 6,7,8,9-tetrahydrocyclopenta[a]naphthyl, 5a,8,9,9a-tetrahydrocyclopenta[a]naphthyl, 4,5,7,9a-tetrahydrocyclopenta[a]naphthyl, 5a,6,7,9a-tetrahydrocyclopenta[a]naphthyl, 7,8,9,9a-tetrahydrocyclopenta[a]naphthyl, 4,6,7,9a-tetrahydrocyclopenta[a]naphthyl, 4,8,9,9a-tetrahydrocyclopenta[a]naphthyl, 4,5,6,9-tetrahydrocyclopenta[a]naphthyl, 4,5,5a,8-tetrahydrocyclopenta[a]naphthyl, 5a,6,7,8-tetrahydrocyclopenta[a]naphthyl, 5a,6,9,9a-tetrahydrocyclopenta[a]naphthyl, 5a,6,7,8,9,9a-hexahydrocyclopenta[a]naphthyl, 4,6,7,8,9,9a-hexahydrocyclopenta[a]naphthyl, 4,5,7,8,9,9a-hexahydrocyclopenta[a]naphthyl, 4,5,5a,8,9,9a-hexahydrocyclopenta[a]naphthyl, 4,5,5a,6,9,9a-hexahydrocyclopenta[a]naphthyl, 4,5,5a,6,7,9a-hexahydrocyclopenta[a]naphthyl, 4,5,5a,6,7,8-hexahydrocyclopenta[a]naphthyl, 4,5,6,7,8,9-hexahydrocyclopenta[a]naphthyl, 4,5,5a,6,7,8,9,9a-hexahydrocyclopenta[a]naphthyl, 4,5,5a,6,7,8,9,9a-octahydrocyclopenta[a]naphthyl, 5,6-trimethyleneindenyl, 4,5-trimethyleneindenyl, 5,6-pentamethyleneindenyl, 4,5-pentamethyleneindenyl, 5,6-hexamethyleneindenyl, 4,5-hexamethyleneindenyl, 5,6-heptamethyleneindenyl, 4,5-heptamethyleneindenyl, 5,6-octamethyleneindenyl, 4,5-octamethyleneindenyl, 5,6-nonamethyleneindenyl, 4,5-nonamethyleneindenyl, 5,6-decamethyleneindenyl, 4,5-decamethyleneindenyl, 5,6-undecamethyleneindenyl, 4,5-undecamethyleneindenyl, 5,6-dodecamethyleneindenyl, 4,5-dodecamethyleneindenyl, 5,6-tridecamethyleneindenyl, 4,5-tridecamethyleneindenyl, 5,6-tetradecamethyleneindenyl, 4,5-tetradecamethyleneindenyl, 5,6-pentadecamethyleneindenyl, 4,5-pentadecamethyleneindenyl, 5,6-hexadecamethyleneindenyl, 4,5-hexadecamethyleneindenyl, 5,6-heptadecamethyleneindenyl, 4,5-heptadecamethyleneindenyl, 5,6-octadecamethyleneindenyl, 4,5-octadecamethyleneindenyl, 5,6-nonadecamethyleneindenyl, 4,5-nonadecamethyleneindenyl, 5,6-eicosamethyleneindenyl, 4,5-eicosamethyleneindenyl, (6Z,8Z,10Z)-cycloocta[e]indenyl, (5Z,7Z,9Z)-cycloocta[f]indenyl, (5E,7Z,9E,11Z,13E)-cyclododeca[f]indenyl, (6E,8Z,10E,12Z,14E)-cyclododeca[e]indenyl, benz[a]fluorenyl, benz[b]fluorenyl, benz[c]fluorenyl, naphth[2,3-a]fluorenyl, naphth[2,3-b]fluorenyl, naphth[2,3-c]fluorenyl, naphth[1,2-a]fluorenyl, naphth[1,2-b]fluorenyl, naphth[1,2-c]fluorenyl, 2,3-tetramethylenefluorenyl, 1,2-tetramethylenefluorenyl, 3,4-tetramethylenefluorenyl, 2,3-trimethylenefluorenyl, 1,2-trimethylenefluorenyl, 3,4-trimethylenefluorenyl, 2,3-pentamethylenefluorenyl, 1,2-pentamethylenefluorenyl, 3,4-pentamethylenefluorenyl, 2,3-hexamethylenefluorenyl, 1,2-hexamethylenefluorenyl, 3,4-hexamethylenefluorenyl, 2,3-heptamethylenefluorenyl, 1,2-heptamethylenefluorenyl, 3,4-heptamethylenefluorenyl, 2,3-octamethylenefluorenyl, 1,2-octamethylenefluorenyl, 3,4-octamethylenefluorenyl, 2,3-nonamethylenefluorenyl, 1,2-nonamethylenefluorenyl, 3,4-nonamethylenefluorenyl, 2,3-decamethylenefluorenyl, 1,2-decamethylenefluorenyl, 3,4-decamethylenefluorenyl, 2,3-undecamethylenefluorenyl, 1,2-undecamethylenefluorenyl, 3,4-undecamethylenefluorenyl, 2,3-dodecamethylenefluorenyl, 1,2-dodecamethylenefluorenyl, 3,4-dodecamethylenefluorenyl, 2,3-tetramethylene-6,7-tetramethylenefluorenyl, 1,2-tetramethylene-7,8-tetramethylenefluorenyl, 3,4-tetramethylene-5,6-tetramethylenefluorenyl, bis-benz[2,3;6,7]fluorenyl, bis-benz[2,3;5,6]fluorenyl, bis-benz[1,2;7,8]fluorenyl, bis-benz[1,2;5,6]fluorenyl, bis-benz[1,2;6,7]fluorenyl, bis-benz[1,2;7,8]fluorenyl, and bis-benz[3,4;5,6]fluorenyl.

Partially hydrogenated polycyclic arenyl ligands retain the numbering scheme of the parent polycyclic arenyl ligand, namely the numbering schemes defined for indenyl, fluorenyl, cyclopenta[b]naphthyl, and cyclopenta[a]naphthyl ligands.

In the context of this document, "homopolymerization" would produce a polymer made from one monomer. For example, homopolymerization of propylene would produce homopolypropylene. Homopolymerization of ethylene would produce homopolyethylene. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An oligomer is typically a polymer having a low molecular weight (such an Mn of less than 25,000 g/mol, preferably less than 2,500 g/mol) or a low number of mer units (such as 75 mer units or less). An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

Non-limiting examples of α-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbomane.

Non-limiting examples of cyclic olefins and diolefins include cyclobutene, cyclopentene, cyclohexene, cycloheptene, cyclooctene, cyclononene, cyclodecene, norbornene, 4-methylnorbomene, 2-methylcyclopentene, 4-methylcyclopentene, vinylcyclohexane, norbomadiene, dicyclopentadiene, 5-ethylidene-2-norbornene, vinylcyclohexene, 5-vinyl-2-norbomene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

Non-limiting examples of vinylaromatic olefins include styrene, para-methylstyrene, para-t-butylstyrene, vinylnaphthylene, vinyltoluene, and divinylbenzene.

Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and non-silicon atoms such as for example B, O, S, Se, Te, N, P, Ge, Sn, Pb, As, F, Cl, Br, or I, are contemplated, where such non-carbon or non-silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or non-silicon moiety is preferably 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or non-silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng., v.* 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. Copolymerization can also incorporate α-olefinic macromonomers of up to 2000 mer units.

The term "catalyst system" is defined to mean a catalyst precursor/activator pair, and an optional support material. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst compound, catalyst precursor, transition metal compound or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

A polymerization catalyst system is a catalyst system that can polymerize monomers to polymer. An "anionic ligand" is a negatively charged ligand which donates one or more pairs of electrons to a metal ion. A "neutral donor ligand" is a neutrally charged ligand which donates one or more pairs of electrons to a metal ion.

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

For the purposes of this invention, ethylene shall be considered an α-olefin.

As used herein, Mn is number average molecular weight, Mw is weight average molecular weight, and Mz is z average molecular weight, wt % is weight percent, and mol % is mole percent. Molecular weight distribution (MWD), also referred to as polydispersity (PDI), is defined to be Mw divided by Mn. Unless otherwise noted, all molecular weight units (e.g., Mw, Mn, Mz) are g/mol. The following abbreviations may be used herein: Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, $^t$Bu is tert-butyl, Oct is octyl, Ph is phenyl, Bn is benzyl, THF or thf is tetrahydrofuran, MAO is methylalumoxane.

The term "continuous" means a system that operates without interruption or cessation. For example a continuous process to produce a polymer would be one where the reactants are continually introduced into one or more reactors and polymer product is continually withdrawn.

For purposes of this invention and claims thereto, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may comprise at least one aromatic group.

DETAILED DESCRIPTION

Metallocene Catalyst Compounds

This invention relates to a novel group 3, 4 or 5 (preferably 4, preferably Hf, Zr, and Ti) transition metal metallocene catalyst compound having at least one arenyl ligand substituted with a cyclopropyl group. This invention relates to a novel group 3, 4 or 5 (preferably 4, preferably Hf, Zr, and Ti) transition metal metallocene catalyst compound having at least one arenyl ligand substituted with: 1) a cyclopropyl group and optionally, 2) at least one other group, such as a substituted or unsubstituted hydrocarbyl group.

This invention also relates to a metallocene compound represented by the formula (1): $A_eMX_{n-e}$ wherein: e is 1 or 2; each A is a substituted monocyclic or polycyclic ligand that is pi-bonded to M and optionally includes one or more ring heteroatoms selected from boron, a group 14 atom that is not carbon, a group 15 atom, or a group 16 atom, and when e is 2 each A may be the same or different, provided that at least one A is substituted with at least one cyclopropyl substituent directly bonded to any $sp^2$ carbon atom at a bondable ring position of the ligand, wherein the cyclopropyl substituent is represented by the formula:

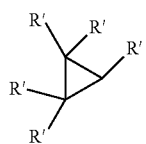

where each R' is, independently, hydrogen, a substituted or unsubstituted hydrocarbyl group, or a halogen; M is a transition metal atom having a coordination number of n and selected from group 3, 4, or 5 of the Periodic Table of Elements (preferably group 4, preferably Ti, Zr or Hf), or a lanthanide metal atom, or actinide metal atom; n is 3, 4, or 5; and each X is a univalent anionic ligand, or two Xs are joined and bound to the metal atom to form a metallocycle ring, or two Xs are joined to form a chelating ligand, a diene ligand, or an alkylidene ligand.

In a preferred embodiment of the invention, in formula 1, e is 2.

In a preferred embodiment of the invention, in formula 1, e is 2 and the two As are bonded together by a bridging group T, wherein the two As may be the same or different.

In a preferred embodiment of the invention, in formula 1, the monocyclic ligand is selected from the group consisting of substituted or unsubstituted cyclopentadienyl, heterocyclopentadienyl, and heterophenyl ligands provided that when e is one, the monocyclic ligand is substituted with at least one cyclopropyl substituent.

In a preferred embodiment of the invention, in formula 1, at least one A is a polycyclic ligand selected from the group consisting of substituted or unsubstituted indenyl, fluorenyl, cyclopenta[a]naphthyl, cyclopenta[b]naphthyl, heteropentalenyl, heterocyclopentapentalenyl, heteroindenyl, heterofluorenyl, heterocyclopentanaphthyl, heterocyclopentaindenyl, and heterobenzocyclopentaindenyl ligands, provided that when e is one, the polycyclic ligand is substituted with at least one cyclopropyl substituent.

In a preferred embodiment of the invention, in formula 1, M is a group 4 metal, preferably Ti, Zr or Hf.

In a preferred embodiment of the invention, in formula 1, each R' is hydrogen.

In a preferred embodiment of the invention, in formula 1, at least one A is a substituted or unsubstituted indenyl ligand, provided that when e is one, the indenyl ligand is substituted with at least one cyclopropyl substituent, preferably the indenyl ligand is substituted with one or more cyclopropyl substituents in any bondable ring position.

In a preferred embodiment of the invention, in formula 1, A is substituted or unsubstituted indenyl ligand and at least one A is substituted with one or more cyclopropyl substituents.

In a preferred embodiment of the invention, in formula 1, the indenyl ligand is substituted with one or more cyclopropyl substituents in one of the 2 or 4 positions.

In a preferred embodiment of the invention, in formula 1, e is 2, the two As are bonded together by a bridging group T, wherein the two As may be the same or different, and at least one A is an indenyl ligand substituted with one or more cyclopropyl substituents, preferably in any of the 2, 4, 5, 6, or 7 positions, preferably the indenyl ligand is substituted with one or more cyclopropyl substituents in the 2 and/or 4 positions.

In a preferred embodiment of the invention, in formula 1, e is 2, the two As are bonded together by a bridging group T, wherein the two As may be the same or different, and T is represented by the formula, $(R'''_2G)_g$, where each G is C, Si, or Ge, g is 1 or 2, and each R''' is, independently, hydrogen, halogen, $C_1$ to $C_{20}$ hydrocarbyl or a $C_1$ to $C_{20}$ substituted hydrocarbyl, and two or more R''' can form a cyclic structure including aromatic, partially saturated, or saturated cyclic or fused ring system. Preferably T is $CH_2$, $CH_2CH_2$, $C(CH_3)_2$, $SiMe_2$, $SiPh_2$, $SiMePh$, $Si(CH_2)_3$, $Si(CH_2)_4$, or $Si(CH_2)_5$.

In a preferred embodiment of the invention, the metallocene compound is represented by one of the following formulae:

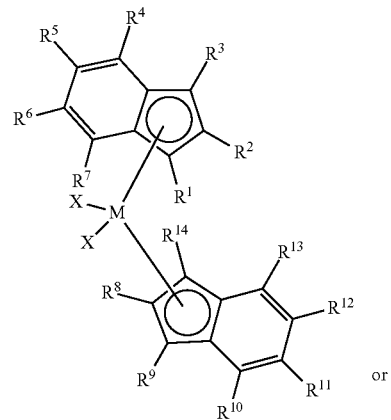

formula (1a)

or

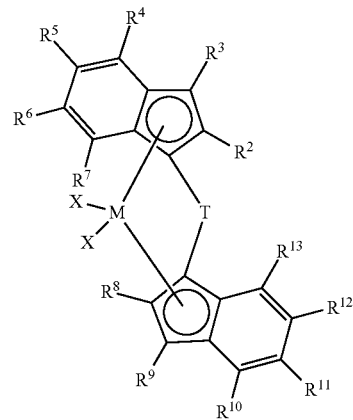

formula (1b)

wherein:

M is a transition metal atom selected from group 3, 4, or 5 of the Periodic Table of Elements (preferably group 4, preferably Hf, Ti or Zr);

T is a bridging group;

each X is a univalent anionic ligand, or two Xs are joined and bound to the metal atom to form a metallocycle ring, or two Xs are joined to form a chelating ligand, a diene ligand, or an alkylidene ligand;

each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is, independently, hydrogen, a substituted hydrocarbyl group, an unsubstituted hydrocarbyl group, or a halide, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is a cyclopropyl substituent wherein the cyclopropyl substituent is represented by the formula:

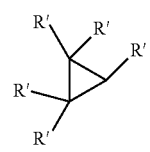

where each R' is, independently, hydrogen, a substituted or unsubstituted hydrocarbyl group, or a halogen;

provided that any adjacent $R^1$ to $R^{14}$ groups that are not a cyclopropyl substituent may form a fused ring or multi-center fused ring system where the rings may be aromatic, partially saturated or saturated. In a preferred embodiment of the invention, when one of $R^1$, $R^2$, $R^3$, $R^4$, $R^5$, $R^6$, and $R^7$ is a cyclopropyl substituent, at least one of the other $R^1$ to $R^7$ groups is not hydrogen. In a preferred embodiment of the invention, when one of $R^8$, $R^9$, $R^{10}$, $R^{11}$, $R^{12}$, $R^{13}$, and $R^{14}$ is a cyclopropyl substituent, at least one of the other $R^8$ to $R^{14}$ groups is not hydrogen. In a preferred embodiment of the invention, when one of $R^1$, $R^2$, $R^3$, $R^4$, $R^5$, $R^6$, and $R^7$ is a cyclopropyl substituent, at least one of the other $R^1$ to $R^7$ groups is not hydrogen, and when one of $R^8$, $R^9$, $R^{10}$, $R^{11}$, $R^{12}$, $R^{13}$, and $R^{14}$ is a cyclopropyl substituent, at least one of the other $R^8$ to $R^{14}$ groups is not hydrogen.

In a preferred embodiment of the invention, in any of formula 1a or 1b, M is a group 4 metal, preferably Ti, Zr or Hf, preferably Zr or Hf.

In a preferred embodiment of the invention, in any of formula 1a or 1b, each R' is hydrogen.

In a preferred embodiment of the invention, in any of formula 1a or 1b, T is represented by the formula, $(R'''_2G)_g$, where each G is C, Si, or Ge, g is 1 or 2, and each R''' is, independently, hydrogen, halogen, $C_1$ to $C_{20}$ hydrocarbyl or a $C_1$ to $C_{20}$ substituted hydrocarbyl, and two or more R''' can form a cyclic structure including aromatic, partially saturated, or saturated cyclic or fused ring system, preferably T is $CH_2$, $CH_2CH_2$, $C(CH_3)_2$, $SiMe_2$, $SiPh_2$, $SiMePh$, $Si(CH_2)_3$, $Si(CH_2)_4$, or $Si(CH_2)_5$.

In a preferred embodiment of the invention, in any of formula 1a or 1b, $R^2$ and/or $R^8$ are cyclopropyl substituents, preferably cyclopropyl, and/or $R^4$ and/or $R^{10}$ are cyclopropyl substituents, preferably cyclopropyl.

In a preferred embodiment of the invention, in any of formula 1a or 1b, one of $R^1$, $R^2$, $R^3$, $R^4$, $R^5$, $R^6$ and $R^7$ is a cyclopropyl substituent, at least one of the other $R^1$ to $R^7$ substitutents is not hydrogen, and when one of $R^8$, $R^9$, $R^{10}$, $R^{11}$, $R^{12}$, $R^{13}$, and $R^{14}$ is a cyclopropyl substituent, at least one of the other $R^8$ to $R^{14}$ groups is not hydrogen.

In a preferred embodiment of the invention, in any of formula 1a or 1b, $R^4$ and/or $R^{10}$ are hydrocarbyl or halogen and/or $R^2$ is cyclopropyl and $R^8$ is hydrogen or hydrocarbyl.

In a preferred embodiment of the invention, in any of formula 1a or 1b, $R^4$ and $R^{10}$ are cyclopropyl.

In a preferred embodiment of the invention, in any of formula 1a or 1b, $R^2$ and $R^8$ are hydrocarbyl.

In a preferred embodiment of the invention, in any of formula 1a or 1b, $R^4$ and $R^{10}$ are cyclopropyl and $R^2$ and $R^8$ are hydrocarbyl.

In a preferred embodiment of the invention of formula 1b, $R^2$ and $R^8$ are cyclopropyl, and $R^4$ and $R^{10}$ are independently halogen or substituted or unsubstituted hydrocarbyl and $R^3$, $R^5$, $R^6$, $R^7$, $R^9$, $R^{11}$, $R^{12}$, and $R^{13}$ are hydrogen.

In a preferred embodiment of the invention of formula 1b, $R^2$ and $R^8$ are a cyclopropyl substituent, and $R^4$, $R^7$, $R^{10}$ and $R^{13}$ are independently halogen or substituted or unsubstituted hydrocarbyl, and $R^3$, $R^5$, $R^6$, $R^9$, $R^{11}$, and $R^{12}$ are hydrogen.

In a preferred embodiment of the invention of formula 1b, $R^2$ and $R^8$ are cyclopropyl, and $R^4$ and $R^{10}$ are independently substituted or unsubstituted aryl substituents, and $R^3$, $R^5$, $R^6$, $R^7$, $R^9$, $R^{11}$, $R^{12}$, and $R^{13}$ are hydrogen.

In a preferred embodiment of the invention of formula 1b, $R^2$ and $R^8$ are cyclopropyl, and $R^4$ and $R^{10}$ are independently selected from phenyl, naphthyl, anthraceneyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-di-isopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, cyclopropyl, cyclobutyl, cyclopentyl, cyclohexyl, carbazolyl, indolyl, pyrrolyl, cyclopenta[b]thiopheneyl and $R^3$, $R^5$, $R^6$, $R^7$, $R^9$, $R^{11}$, $R^{12}$, and $R^{13}$ are hydrogen.

In a preferred embodiment of the invention of formula 1b, $R^2$ and $R^8$ are cyclopropyl, and $R^4$ and $R^{10}$ are independently selected from fluoro, chloro, bromo, iodo, methyl, ethyl, n-propyl, isopropyl, cyclopropyl, n-butyl, isobutyl, sec-butyl, tert-butyl, cyclobutyl, n-pentyl, isopentyl, cyclopentyl, n-hexyl, isohexyl, and cyclohexyl, and $R^3$, $R^5$, $R^6$, $R^7$, $R^9$, $R^{11}$, $R^{12}$, and $R^{13}$ are hydrogen.

In a preferred embodiment of the invention of formula 1b, $R^2$ and $R^8$ are cyclopropyl, and $R^4$, $R^7$, $R^{10}$ and $R^{13}$ are independently selected from fluoro, chloro, bromo, iodo, methyl, ethyl, n-propyl, isopropyl, cyclopropyl, n-butyl, isobutyl, sec-butyl, tert-butyl, and cyclobutyl, and $R^3$, $R^5$, $R^6$, $R^9$, $R^{11}$, and $R^{12}$ are hydrogen.

In a preferred embodiment of the invention of formula 1b, $R^4$ and $R^{10}$ are cyclopropyl, and $R^2$ and $R^8$ are independently substituted or unsubstituted hydrocarbyl, and $R^3$, $R^5$, $R^6$, $R^7$, $R^9$, $R^{11}$, $R^{12}$, and $R^{13}$ are hydrogen.

In a preferred embodiment of the invention of formula 1b, $R^4$ and $R^{10}$ are cyclopropyl, and $R^2$ and $R^8$ are independently selected from hydrogen, methyl, ethyl, n-propyl, isopropyl, cyclopropyl, n-butyl, isobutyl, sec-butyl, tert-butyl, cyclobutyl, n-pentyl, isopentyl, cyclopentyl, n-hexyl, isohexyl, and cyclohexyl, and $R^3$, $R^5$, $R^6$, $R^7$, $R^9$, $R^{11}$, $R^{12}$, and $R^{13}$ are hydrogen.

In a preferred embodiment of the invention of formula 1b, $R^6$ and $R^{12}$ are independently a cyclopropyl substituent, and $R^2$, $R^4$, $R^8$ and $R^{10}$ are independently substituted or unsubstituted hydrocarbyl, and $R^3$, $R^5$, $R^7$, $R^9$, $R^{11}$, and $R^{13}$ are hydrogen.

In a preferred embodiment of the invention of formula 1b, $R^6$ and $R^{12}$ are cyclopropyl, and $R^2$, $R^4$, $R^8$ and $R^{10}$ are independently selected from hydrogen, methyl, ethyl, n-propyl, isopropyl, cyclopropyl, n-butyl, isobutyl, sec-butyl, tert-butyl, cyclobutyl, n-pentyl, isopentyl, cyclopentyl, n-hexyl, isohexyl, phenyl, and cyclohexyl, and $R^3$, $R^5$, $R^7$, $R^9$, $R^{11}$, and $R^{13}$ are hydrogen.

In a preferred embodiment of the invention, in any of formula 1a, $R^2$ and $R^8$ are cyclopropyl, and $R^4$, $R^7$, $R^{10}$ and $R^{13}$ are independently selected from hydrogen, fluoro, chloro, bromo, iodo, methyl, ethyl, n-propyl, isopropyl, cyclopropyl, n-butyl, isobutyl, sec-butyl, tert-butyl, and cyclobutyl, and $R^3$, $R^5$, $R^6$, $R^9$, $R^{11}$, and $R^{12}$ are hydrogen.

In a preferred embodiment of the invention, in any of formula 1a or 1b, when one $R^1$, $R^2$, $R^3$, $R^4$, $R^5$, $R^6$ and $R^7$ is a cyclopropyl substituent, at least one of the other $R^1$ to $R^7$ substitutents is not hydrogen.

In a preferred embodiment of the invention, in any of formula 1a or 1b, when one of $R^1$, $R^2$, $R^3$, $R^4$, $R^5$, $R^6$, and $R^7$ is a cyclopropyl substituent, at least one of the other $R^1$ to $R^7$ groups is not hydrogen, and when one of $R^8$, $R^9$, $R^{10}$, $R^{11}$, $R^{12}$, $R^{13}$, and $R^{14}$ is a cyclopropyl substituent, at least one of the other $R^8$ to $R^{14}$ groups is not hydrogen.

In a preferred embodiment of the invention, the metallocene compound is represented by the formula (2):

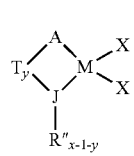

wherein:

M is a group 3, 4 or 5 transition metal atom, or a lanthanide metal atom, or actinide metal atom;

A is a substituted monocyclic or polycyclic ligand that is pi-bonded to M and is substituted with at least one cyclopropyl substituent directly bonded to any $sp^2$ carbon atom at a bondable ring position of the ligand;

wherein the cyclopropyl substituent is represented by the formula:

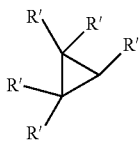

wherein each R' is, independently, hydrogen, a substituted hydrocarbyl group, an unsubstituted hydrocarbyl group, or a halogen;

T is an optional bridging group that is bonded to A and J, and is present when y is one and absent when y is zero;

y is zero or one;

J is a heteroatom with a coordination number of three from group 15 or with a coordination number of two from group 16 of the Periodic Table of Elements;

R" is a $C_1$-$C_{100}$ substituted or unsubstituted hydrocarbyl radical;

x is the coordination number of the heteroatom J where "x-1-y" indicates the number of R" substituents bonded to J; and each X is a univalent anionic ligand, or two Xs are joined and bound to the metal atom to form a metallocycle ring, or two Xs are joined to form a chelating ligand, a diene ligand, or an alkylidene ligand.

In a preferred embodiment of the invention, the metallocene compound of formula (2) is represented by one of the following formulae:

formula (2a)

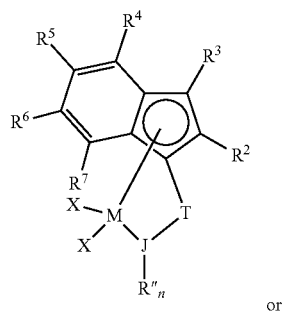

or formula (2b)

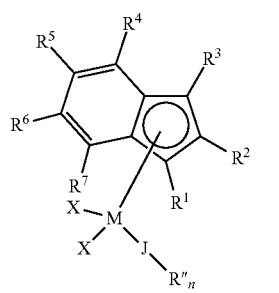

wherein:

T is a bridging group;

J is a heteroatom with a coordination number of three from group 15 or with a coordination number of two from group 16 of the Periodic Table of Elements;

M, X and R" are as defined for formula (2); n is 0, 1 or 2 and n represents the number of R" substituents, and n is one when J is a group 15 heteroatom and T is present, or a group 16 heteroatom and T is absent;

n is two when J is a group 15 heteroatom and T is absent;

n is zero when J is a group 16 heteroatom and T is present;

each $R^1$, $R^2$, $R^3$, $R^4$, $R^5$, $R^6$, and $R^7$ is, independently, hydrogen, a substituted hydrocarbyl group, an unsubstituted hydrocarbyl group, or a halide, provided that at least one of $R^1$, $R^2$, $R^3$, $R^4$, $R^5$, $R^6$, and $R^7$ is a cyclopropyl substituent; and provided that any adjacent $R^1$ to $R^7$ groups that are not a cyclopropyl substituent may form a fused ring or multicenter fused ring system where the rings may be aromatic, partially saturated or saturated; wherein the cyclopropyl substituent is represented by the formula:

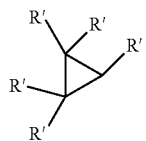

wherein each R' is, independently, hydrogen, a substituted hydrocarbyl group, an unsubstituted hydrocarbyl group, or a halogen.

In an alternate embodiment of the invention, when one of $R^1$, $R^2$, $R^3$, $R^4$, $R^5$, $R^6$, and $R^7$ is a cyclopropyl substituent, at least one of the other $R^1$ to $R^7$ groups is not hydrogen.

In a preferred embodiment of the invention, in any of formula 2, A is a monocyclic ligand and is selected from the group consisting of substituted cyclopentadienyl, heterocyclopentadienyl, and heterophenyl ligands.

In a preferred embodiment of the invention, in any of formula 2, A is a polycyclic ligand and is selected from the group consisting of substituted indenyl, fluorenyl, cyclopenta[a]naphthyl, cyclopenta[b]naphthyl, heteropentalenyl, heterocyclopentapentalenyl, heteroindenyl, heterofluorenyl, heterocyclopentanaphthyl, heterocyclopentaindenyl, and heterobenzocyclopentaindenyl ligands.

In a preferred embodiment of the invention, in any of formula 2, 2a or 2b, M is a group 4 metal, preferably Hf, Ti or Zr.

In a preferred embodiment of the invention, in any of formula 2, 2a or 2b, M is preferably Ti.

In a preferred embodiment of the invention, in any of formula 2, 2a or 2b, each R' is hydrogen.

In a preferred embodiment of the invention, in any of formula 2 or 2a, T is represented by the formula, $(R'''_2G)_g$, where each G is C, Si, or Ge, g is 1 or 2, and each R''' is, independently, hydrogen, halogen, $C_1$ to $C_{20}$ hydrocarbyl or a $C_1$ to $C_{20}$ substituted hydrocarbyl, and two or more R''' can form a cyclic structure including aromatic, partially saturated, or saturated cyclic or fused ring system preferably T is $CH_2$, $CH_2CH_2$, $C(CH_3)_2$, $SiMe_2$, $SiPh_2$, $SiMePh$, $Si(CH_2)_3$, $Si(CH_2)_4$, or $Si(CH_2)_5$.

In a preferred embodiment of the invention, in any of formula 2, A is a substituted indenyl ligand, preferably substituted with one or more cyclopropyl substituents in the 2 and/or 4 positions.

In a preferred embodiment of the invention, in any of formula 2, 2a or 2b, J is nitrogen, phosphorus, oxygen or sulfur.

In a preferred embodiment of the invention, in any of formula 2a or 2b, when one $R^1$, $R^2$, $R^3$, $R^4$, $R^5$, $R^6$ and $R^7$ is a cyclopropyl substituent, at least one of the other $R^1$ to $R^7$ substitutents is not hydrogen.

In an alternate embodiment of the invention, in any of formulae described herein, when one $R^1$, $R^2$, $R^3$, $R^4$, $R^5$, $R^6$ and $R^7$ is a cyclopropyl substituent, at least one of the other $R^1$ to $R^7$ substitutents is not hydrogen.

In a preferred embodiment of the invention, in any of formula 2a or 2b, $R^2$ is cyclopropyl, and $R^2$, $R^3$, $R^4$, $R^5$, $R^6$ and $R^7$ is hydrogen.

In a preferred embodiment of the invention, in any formula 2, 2a or 2b, R" is selected from methyl, ethyl, phenyl, naphthyl, benzyl, adamantyl, norbornyl, cyclopropyl, cyclobutyl, cyclopentyl, cyclohexyl, cycloheptyl, cyclooctyl, cyclodecyl, cyclododecyl and all isomers of propyl, butyl, pentyl, hexyl, heptyl, octyl, nonyl, decyl, undecyl, dodecyl, methylphenyl, ethylphenyl, propylphenyl, butylphenyl, dimethylphenyl, trimethylphenyl, diethylphenyl, dipropylphenyl, tripropylphenyl, dibutylphenyl, dimethylpropylphenyl, and dimethylbutylyphenyl.

In a preferred embodiment of the invention, the metallocene compound is represented by the formula (3):

wherein:

M is a group 4 transition metal atom, or a lanthanide metal atom, or actinide metal atom;

each A is, independently, a substituted or unsubstituted monocyclic or polycyclic ligand pi-bonded to M, and optionally includes one or more ring heteroatoms selected from boron, a group 14 atom that is not carbon, a group 15 atom, or a group 16 atom, and each A may be the same or different, provided that at least one A is substituted with at least one cyclopropyl substituent directly bonded to any $sp^2$ carbon atom at a bondable ring position of the ligand;

T is an optional bridging group that is bonded to each A, and is present when y is one and absent when y is zero;

y is zero or one; and each X is a univalent anionic ligand, or two X are joined and bound to the metal atom to form a metallocycle ring, or two X are joined to form a chelating ligand, a diene ligand, or an alkylidene ligand.

In a preferred embodiment of the invention in any formula described herein having one or more R groups, at least two (alternately at least three, alternately at least four, alternately at least 5, alternately at least 6) of $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ are a cyclopropyl group.

In a preferred embodiment of the invention in any formula described herein having one or more R groups, at least two (alternately at least three, alternately at least four, alternately at least 5, alternately at least 6) of $R^1$, $R^2$, $R^3$, $R^4$, $R^5$, $R^6$, or $R^7$ are a cyclopropyl group.

In a preferred embodiment of the invention in any formula described herein having one or more R groups, at least two (preferably at least three, preferably at least four) of $R^2$, $R^4$, $R^8$ and $R^{10}$ are a cyclopropyl group.

In a preferred embodiment of the invention in any bis-indenyl formula described herein, $R^2$ and $R^8$ are a cyclopropyl group.

In a preferred embodiment of the invention in any formula described herein, at least one of $R^1$, $R^2$, $R^3$, $R^4$, $R^5$, $R^6$, and $R^7$ is a cyclopropyl group, at least one of the other $R^1$ to $R^7$ groups is a substituted or unsubstituted aryl group; and, in bis-indenyl formulae, at least one of $R^8$, $R^9$, $R^{10}$, $R^{11}$, $R^{12}$, $R^{13}$, and $R^{14}$ is a cyclopropyl group and at least one of the other $R^8$ to $R^{14}$ groups is substituted or unsubstituted aryl group.

In a preferred embodiment, at least one of $R^1$, $R^2$, $R^3$, $R^4$, $R^5$, $R^6$, and $R^7$ (preferably $R^2$) is a cyclopropyl group, at least one of the other $R^1$ to $R^7$ groups (preferably $R^4$) is a substituted or unsubstituted aryl group (preferably carbazol, substituted carbazol, naphthyl, substituted naphthyl, phenyl or substituted phenyl), and in bis-indenyl formulae (1a or 1b) at least one of $R^8$, $R^9$, $R^{10}$, $R^{11}$, $R^{12}$, $R^{13}$, and $R^{14}$ (preferably $R^8$) is a cyclopropyl group, at least one of the other $R^8$ to $R^{14}$ groups (preferably $R^{10}$) is substituted or unsubstituted aryl group (preferably carbazol, substituted carbazol, naphthyl, substituted naphthyl, phenyl, or substituted phenyl).

In a preferred embodiment of the invention in any embodiment of any formula described herein, $R^2$ (and $R^8$ in bis-indenyl formulae) is/are cyclopropyl, and $R^4$ (and $R^{10}$ in bis-indenyl formulae) is/are phenyl, carbazolyl, and/or naphthyl.

In a preferred embodiment of the invention in any embodiment of any formula described herein, $R^2$ (and $R^8$ in bis-indenyl formulae) is/are cyclopropyl, and $R^4$ (and $R^{10}$ in bis-indenyl formulae) is/are a substituted or unsubstituted aryl group.

An aryl group is defined to be a single or multiple fused ring group where at least on ring is aromatic. A substituted aryl group is an aryl group where a hydrogen has been replaced by a substituted or unsubstituted hydrocarbyl group, and/or wherein one or more ring carbons have been replaced by a heteroatom or heteroatom group. Examples of useful aryl groups include phenyl, benzyl, carbazolyl, indolyl, naphthyl, and the like.

In a preferred embodiment of the invention in any embodiment of any formula described herein, each R' of the cyclopropyl group is independently, hydrogen or a substituted hydrocarbyl group or unsubstituted hydrocarbyl group, or a heteroatom, preferably hydrogen, methyl, ethyl, propyl, butyl, pentyl, hexyl, or an isomer thereof.

Preferred cyclopropyl groups include: cyclopropyl and methylcyclopropyl.

In a preferred embodiment of the invention in any embodiment of any formula described herein, each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from halides and $C_1$ to $C_5$ alkyl groups, preferably each X is a methyl group.

In a preferred embodiment of the invention in any embodiment of any formula described herein, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is, independently, hydrogen or a substituted hydrocarbyl group or unsubstituted hydrocarbyl group, preferably a heteroatom, hydrogen, methyl, ethyl, propyl, butyl, pentyl, hexyl, or an isomer thereof, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is a cyclopropyl group.

In a preferred embodiment of any formula described herein, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is, independently selected from hydrogen, methyl, ethyl, phenyl, benzyl, cyclobutyl, cyclopentyl, cyclohexyl, naphthyl, anthracenyl, carbazolyl, indolyl, pyrrolyl, cyclopenta[b]thiopheneyl, fluoro, chloro, bromo, iodo and isomers of propyl, butyl, pentyl, hexyl, heptyl, octyl, nonyl, decyl, methylphenyl, dimethylphenyl, ethylphenyl, diethylphenyl, propylphenyl, dipropylphenyl, butylphenyl, dibutylphenyl, methylbenzyl, methylpyrrolyl, dimethylpyrrolyl, methylindolyl, dimethylindolyl, methylcarbazolyl, dimethylcarbazolyl, methylcyclopenta[b]thiopheneyl dimethylcyclopenta[b]thiopheneyl.

In a preferred embodiment of the invention in any embodiment of any formula described herein, T is a bridging group and comprises Si, Ge, or C, preferably T is dialkyl silylene or dialkyl germanylene, preferably T is dimethyl silylene.

In a preferred embodiment of the invention in any embodiment of any formula described herein, T is a bridging group and is represented by R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C═CR', R'C═CR'CR'$_2$, R'$_2$CCR'═CR'CR'$_2$, R'C═CR'CR'═CR', R'C═CR'CR'$_2$CR'$_2$, R'$_2$CSiR'$_2$, R'$_2$SiSiR'$_2$, R$_2$CSiR'$_2$CR'$_2$, R'$_2$SiCR'$_2$SiR'$_2$, R'C═CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C═CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'═CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'═CR', R'$_2$C—Se—CR'$_2$, R'$_2$CR'$_2$C—Se—CR'$_2$CR'$_2$, R'$_2$C—Se—CR$_2$CR'$_2$, R'$_2$C—Se—CR'═CR', R'$_2$C—N═CR', R'$_2$C—NR'—CR'$_2$, R'$_2$C—NR'—CR'$_2$CR'$_2$, R'$_2$C—NR'—CR'═CR', R'$_2$CR'$_2$C—NR'—CR'$_2$CR'$_2$, R'$_2$C—P═CR', or R'$_2$C—PR'—CR'$_2$ where each R' is, independently, hydrogen or a $C_1$ to $C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferably, T is a bridging group comprising carbon or silica, such as dialkylsilylene, preferably T is selected from $CH_2$, $CH_2CH_2$, $C(CH_3)_2$, $SiMe_2$, $SiPh_2$, SiMePh, cyclotrimethylenesilylene ($Si(CH_2)_3$), $(Ph)_2C$, $(p-(Et)_3SiPh)_2C$, cyclotetramethylenesilylene ($Si(CH_2)_4$), and cyclopentamethylenesilylene ($Si(CH_2)_5$).

In a preferred embodiment of the invention in any embodiment of any formula described herein, T is represented by the formula $R_2{}^aJ$, where J is C, Si, or Ge, and each $R^a$ is, independently, hydrogen, halogen, $C_1$ to $C_{20}$ hydrocarbyl or a $C_1$ to $C_{20}$ substituted hydrocarbyl, and two $R^a$ can form a cyclic structure including aromatic, partially saturated, or saturated cyclic or fused ring system.

In a preferred embodiment of the invention in any embodiment of any formula described herein, T is represented by the formula, $(R'''_2G)_g$, where each G is C, Si, or Ge, g is 1 or 2, and each R''' is, independently, hydrogen, halogen, $C_1$ to $C_{20}$ hydrocarbyl or a $C_1$ to $C_{20}$ substituted hydrocarbyl, and two or more R''' can form a cyclic structure including aromatic, partially saturated, or saturated cyclic or fused ring system, preferably T is $CH_2$, $CH_2CH_2$, $C(CH_3)_2$, $SiMe_2$, $SiPh_2$, SiMePh, $Si(CH_2)_3$, $Si(CH_2)_4$, or $Si(CH_2)_5$.

Metallocene compounds that are particularly useful in this invention include one or more of:

dimethylsilylene-bis(2-cyclopropyl-4-carbazol-9-ylindenyl) zirconium dichloride;
dimethylsilylene-bis(2-cyclopropyl-4-naphth-1-ylindenyl) zirconium dichloride;
dimethylsilylene-(2-cyclopropyl-4-carbazol-9-ylindenyl)(2-cyclopropyl-4-phenylindenyl)zirconium dichloride;
dimethylsilylene-(2-cyclopropyl-4-carbazol-9-ylindenyl)(2-methyl-4-phenylindenyl) zirconium dichloride;
bis(2-cyclopropylindenyl)zirconium dichloride;
dimethylsilylene-(2-cyclopropylindenyl)(tert-butylamido) zirconium dichloride;
dimethylsilylene-(2-cyclopropylindenyl)(tert-butylamido) titanium dichloride;
dimethylsilylene-bis(2-cyclopropyl-4-para-tert-butylphenylindenyl)zirconium dichloride;
dimethylsilylene-bis(2-cyclopropyl-4-naphth-1-ylindenyl) hafnium dichloride;
dimethylsilylene-bis(2-cyclopropyl-4-chloroindenyl)zirconium dichloride;
dimethylsilylene-bis(2-cyclopropyl-4,7-dimethylindenyl) zirconium dichloride;
dimethylsilylene-bis(2-cyclopropyl-4,7-dimethylindenyl) hafnium dichloride;
dimethylsilylene-bis(2-cyclopropyl-4-carbazol-9-ylindenyl) hafnium dichloride;
dimethylsilylene-bis(2-methyl-4-cyclopropylindenyl)zirconium dichloride;
cyclotetramethylenesilylene-(2-cyclopropyl-4-phenylindenyl)(2-cyclopropyl-4-carbazol-9-ylindenyl) zirconium dichloride;
dimethylsilylene-bis(2-cyclopropyl-4-phenylindenyl)zirconium dichloride;
dimethylsilylene-(2-cyclopropyl-4-para-tert-butylphenylindenyl)(2-methyl-4-phenylindenyl)zirconium dichloride;
dimethylsilylene-bis(2-cyclopropyl-4-para-tert-butylphenylindenyl)hafnium dichloride;
cyclotetramethylenesilylene-bis(2-methyl-4-cyclopropylindenyl)zirconium dichloride;
cyclotetramethylenesilylene-bis(2-methyl-4-cyclopropylindenyl)hafnium dichloride;
dimethylsilylene-bis(2,4-dicyclopropylindenyl)zirconium dichloride;
dimethylsilylene-bis(2-methyl-4-cyclopropylindenyl)hafnium dichloride;
cyclotetramethylenesilylene-bis(2-ethyl-4-cyclopropylindenyl)hafnium dichloride;
cyclotrimethylenesilylene-bis(2-ethyl-4-cyclopropylindenyl)hafnium dichloride;
cyclotrimethylenesilylene-bis(2-isopropyl-4-cyclopropylindenyl)hafnium dichloride;
dimethylsilylene-bis(2-methyl-4-phenyl-6-cyclopropylindenyl)zirconium dichloride;
dimethylsilylene-bis(2-ethyl-4-cyclopropylindenyl)hafnium dichloride;
dimethylsilylene-bis(2-isopropyl-4-cyclopropylindenyl)hafnium dichloride;
where, in alternate embodiments, the dichloride in any of the compounds listed above may be replaced with dialkyl (such as dimethyl), dialkaryl, diflouride, diiodide, or dibromide, or a combination thereof.

In a preferred embodiment, the dichloride in any of the compounds listed above may be replaced with dialkyl (such as dimethyl) or dibromo. In a preferred embodiment, the zirconium in any of the compounds listed above is replaced with hafnium or titanium. In a preferred embodiment, the hafnium in any of the compounds listed above is replaced with zirconium or titanium. In a particularly preferred embodiment, the dichloride in any of the compounds listed above replaced with dimethyl and the metal is replaced with hafnium. In a particularly preferred embodiment, the dichloride in any of the compounds listed above replaced with dimethyl and the metal is replaced with titanium.

Particularly preferred compounds include: dimethylsilylene-bis(2-cyclopropyl-4,7-dimethylindenyl)hafnium dichloride; dimethylsilylene-(2-cyclopropylindenyl)(tert-butylamido)titanium dichloride; and dimethylsilylene-bis(2-cyclopropyl-4-para-tert-butylphenyl indenyl)zirconium dimethyl.

Preferred metallocene compounds that are particularly useful in this invention include one or more of: dimethylsilylene-bis(2-cyclopropyl-4-carbazol-9-ylindenyl)zirconium dichloride; dimethylsilylene-bis(2-cyclopropyl-4-naphth-1-ylindenyl)zirconium dichloride; dimethylsilylene-(2-cyclopropyl-4-carbazol-9-ylindenyl) (2-cyclopropyl-4-phenylindenyl) zirconium dichloride; bis(2-cyclopropylindenyl)zirconium dichloride; dimethylsilylene-(2-cyclopropylindenyl)(tert-butylamido)zirconium dichloride; dimethylsilylene-bis(2-cyclopropyl-4-para-tert-butylphenylindenyl)zirconium dichloride; dimethylsilylene-bis(2-cyclopropyl-4-naphth-1-ylindenyl)zirconium dichloride; dimethylsilylene-bis(2-cyclopropyl-4-chloroindenyl) zirconium dichloride; dimethylsilylene-bis(2-cyclopropyl-4, 7-dimethylindenyl)zirconium dichloride; dimethylsilylene-bis(2-cyclopropyl-4-carbazol-9-ylindenyl)zirconium dichloride; dimethylsilylene-bis(2-methyl-4-cyclopropylindenyl)zirconium dichloride; dimethylsilylene-(2-cyclopropyl-4-phenylindenyl)(2-cyclopropyl-4-carbazol-1-ylindenyl)zirconium dichloride, where, in alternate embodiments, the dichloride in any of the compounds listed above may be replaced with dialkyl, diflouride, diiodide, or dibromide.

In a preferred embodiment in any of the processes described herein one metallocene catalyst compound is used, e.g. the metallocene catalyst compounds are not different. For purposes of this invention one metallocene catalyst compound is considered different from another if they differ by at least one atom. For example "bis-indenyl zirconium dichloride" is different from (indenyl)(2-methyl-indenyl) zirconium dichloride" which is different from "(indenyl)(2-methylindenyl) hafnium dichloride." Thus, metallocene catalyst compounds that differ only by isomer are considered the same, e.g., rac-dimethylsilylbis(2-methyl-4-phenyl) hafnium dimethyl is considered to be the same as meso-dimethylsilylbis(2-methyl-4-phenyl) hafnium dimethyl.

In a preferred embodiment of the invention, the catalyst compound is in the rac form. In a preferred embodiment of the invention, at least 90 wt % of the catalyst compound is in the rac form, based upon the weight of the rac and meso forms present, preferably from 92 to 100 wt %, preferably from 95 to 100 wt %, preferably from 98 to 100 wt %. In a preferred embodiment of the invention, the ratio of rac to meso in the catalyst compound is from 1:100 to 100:1, preferably 1:1 to 50:1, preferably 5:1 to 20:1, preferably 5:1 to 15:1.

Amounts of rac and meso isomers are determined by proton NMR. $^1$H NMR data are collected at 22° C. in a 5 mm probe using a 400 MHz Bruker spectrometer with deuterated solvent in which the precatalyst compound is completely soluble. Data is recorded using a maximum pulse width of 45°, 8 seconds between pulses and signal averaging 16 transients.

In some embodiments, two or more different metallocene catalyst compounds are present in the catalyst system used herein. In some embodiments, two or more different metallocene catalyst compounds are present in the reaction zone where the process(es) described herein occur. When two transition metal compound based catalysts are used in one reactor as a mixed catalyst system, the two transition metal compounds should be chosen such that the two are compatible. A simple screening method such as by $^1$H or $^{13}$C NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination. If one or more transition metal compounds contain an X ligand which is not a hydride, hydrocarbyl, or substituted hydrocarbyl, then the alumoxane may be contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

Methods to Prepare the Metallocene Compounds

Ni-catalyzed Kumada reaction with cyclopropylmagnesium bromide can be used to produce cyclopropyl substituted indenes useful herein. Typically, a carbene-phosphine Ni complex is used to achieve cyclopropyl-substituted indenes starting from the respective bromo-substituted indenes. Production of bromo-substituted indenes is generally described in US 2007/0135594; US2007/0135623; U.S. Pat. Nos. 7,557,171; 7,538,168; 7,446,216; 7,550,544; 7,709,670; and 7,812,104.

For example, cyclopropyl substituted indenes may be prepared according the scheme A below:

Scheme A:

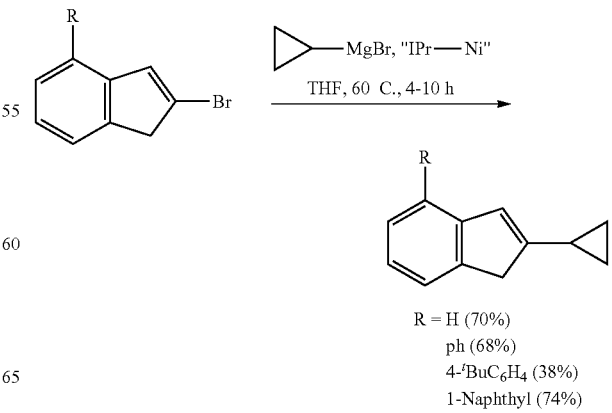

R = H (70%)
ph (68%)
4-$^t$BuC$_6$H$_4$ (38%)
1-Naphthyl (74%)

"IPr—Ni" = 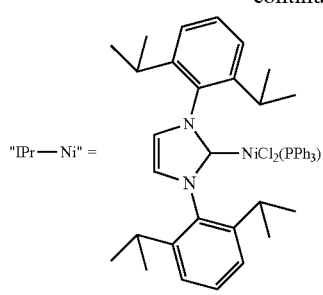

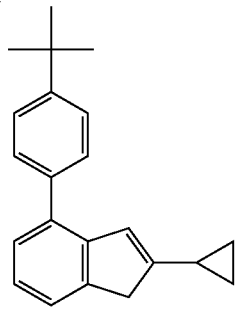

However, the synthesis of 2-cyclopropyl-substituted indenes from the respective 2-bromo-4-arylindenes can be achieved via 2-cyclopropyl-4-chloroindene which then could be used in cross-coupling reactions with suitable aryl- or azol-containing substrates. For example, 2-bromo-4-chloroindene can be obtained from 4-chloroindene and NBS (N-Bromosuccinimide). Thereafter, one can use a Ni-catalyzed cross-coupling reaction of this substrate with cyclopropylmagnesium bromide to obtain 2-cyclopropyl-4-chloroindene a illustrated in Scheme B.

Scheme B:

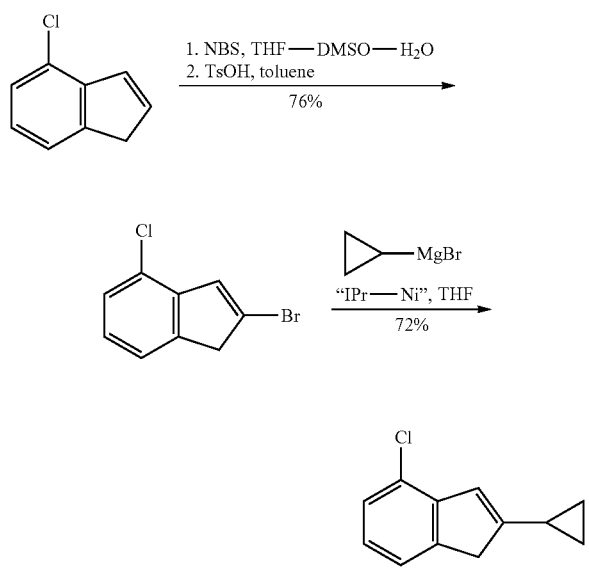

where NBS is N-Bromosuccinimide; THF-DMSO is tetrahydrofuran-dimethyl sulfoxide; and TsOH is tosylic acid.

Alternatively, this indene may be synthesized via Pd-catalyzed cross-coupling reaction of 2-cyclopropyl-4-chloroindene and 4-tert-butylphenylboronic acid as illustrated in Scheme C.

Scheme C:

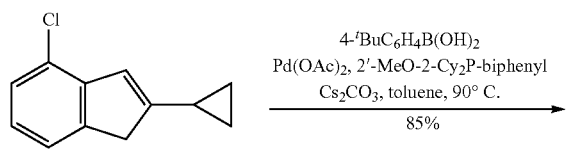

where OAc is acetate; and Cy is cyanate.

Activators

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

In one embodiment, alumoxane activators are utilized as an activator in the catalyst composition. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

When the activator is an alumoxane (modified or unmodified), some embodiments select the maximum amount of activator at a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

The term "non-coordinating anion" (NCA) means an anion which either does not coordinate to a cation or which is only weakly coordinated to a cation thereby remaining sufficiently labile to be displaced by a neutral Lewis base.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; 5,502,124; and U.S. patent application Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the group 4 cation) which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277, 003 A1, and EP 0 277,004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following formula (1):

$$(Z)_d^+ (A^{d-}) \quad (1)$$

wherein Z is (L-H) or a reducible Lewis Acid, L is an neutral Lewis base; H is hydrogen; (L-H)$^+$ is a Bronsted acid; $A^{d-}$ is a non-coordinating anion having the charge d−; and d is an integer from 1 to 3.

When Z is (L-H) such that the cation component is (L-H)$_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation (L-H)$_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: (Ar$_3$C$^+$), where Ar is aryl or aryl substituted with a heteroatom, a C$_1$ to C$_{40}$ hydrocarbyl, or a substituted C1 to C40 hydrocarbyl, preferably the reducible Lewis acid is represented by the formula: (Ph$_3$C$^+$), where Ph is phenyl or phenyl substituted with a heteroatom, a C$_1$ to C$_{40}$ hydrocarbyl, or a substituted C$_1$ to C$_{40}$ hydrocarbyl. In a preferred embodiment, the reducible Lewis acid is triphenyl carbenium.

The anion component $A^{d-}$ include those having the formula [M$^{k+}$Q$_n$]$^{d-}$ wherein k is 1, 2, or 3; n is 1, 2, 3, 4, 5, or 6, preferably 3, 4, 5 or 6; n−k=d; M is an element selected from group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ components also include diboron compounds as disclosed in U.S. Pat. No. 5,447,895, which is fully incorporated herein by reference.

In a preferred embodiment, this invention relates to a method to polymerize olefins comprising contacting olefins (preferably ethylene) with a metallocene catalyst compound, a chain transfer agent and a boron containing NCA activator represented by the formula (2):

$$Z_d^+ (A^{d-}) \quad (2)$$

where: Z is (L-H) or a reducible Lewis acid; L is an neutral Lewis base (as further described above); H is hydrogen; (L-H) is a Bronsted acid (as further described above); $A^{d-}$ is a boron containing non-coordinating anion having the charge d (as further described above); d is 1, 2, or 3.

In a preferred embodiment in any NCA's represented by Formula 2 described above, the reducible Lewis acid is represented by the formula: (Ar$_3$C$^+$), where Ar is aryl or aryl substituted with a heteroatom, a C$_1$ to C$_{40}$ hydrocarbyl, or a substituted C1 to C40 hydrocarbyl, preferably the reducible Lewis acid is represented by the formula: ($Ph_3C^+$), where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's represented by Formula 2 described above, $Z_d^+$ is represented by the formula: $(L\text{-}H)_d^+$, wherein L is an neutral Lewis base; H is hydrogen; (L-H) is a Bronsted acid; and d is 1, 2, or 3, preferably $(L\text{-}H)_d^+$ is a Bronsted acid selected from ammoniums, oxoniums, phosphoniums, silyliums, and mixtures thereof.

In a preferred embodiment in any of the NCA's represented by Formula 2 described above, the anion component $A^{d-}$ is represented by the formula $[M^*k^*+Q^*n^*]^{d*-}$ wherein k* is 1, 2, or 3; n* is 1, 2, 3, 4, 5, or 6 (preferably 1, 2, 3, or 4); n*–k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene) with a metallocene catalyst compound, a chain transfer agent and an NCA activator represented by the formula (3):

where R is a monoanionic ligand; M** is a group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula 3 also comprises a suitable cation that is essentially non-interfering with the ionic catalyst complexes formed with the transition metal compounds, preferably the cation is $Z_d^+$ as described above.

In a preferred embodiment in any of the NCA's comprising an anion represented by Formula 3 described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; $-SR^1$, $-NR^2_2$, and $-PR^3_2$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment in any of the NCA's comprising an anion represented by Formula 3 described above, the NCA also comprises cation comprising a reducible Lewis acid represented by the formula: ($Ar_3C^+$), where Ar is aryl or aryl substituted with a heteroatom, a $C_1$ to $C_{40}$ hydrocarbyl, or a substituted C1 to C40 hydrocarbyl, preferably the reducible Lewis acid represented by the formula: ($Ph_3C^+$), where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's comprising an anion represented by Formula 3 described above, the NCA also comprises a cation represented by the formula, $(L\text{-}H)_d^+$, wherein L is an neutral Lewis base; H is hydrogen; (L-H) is a Bronsted acid; and d is 1, 2, or 3, preferably $(L\text{-}H)_d^+$ is a Bronsted acid selected from ammoniums, oxoniums, phosphoniums, silyliums, and mixtures thereof.

Further examples of useful activators include those disclosed in U.S. Pat. Nos. 7,297,653 and 7,799,879.

Another activator useful herein comprises a salt of a cationic oxidizing agent and a noncoordinating, compatible anion represented by the formula (4):

wherein $OX^{e+}$ is a cationic oxidizing agent having a charge of e+; e is 1, 2, or 3; d is 1, 2 or 3; and $A^{d-}$ is a non-coordinating anion having the charge of d– (as further described above). Examples of cationic oxidizing agents include: ferrocenium, hydrocarbyl-substituted ferrocenium, $Ag^+$, or $Pb^{+2}$. Preferred embodiments of $A^{d-}$ include tetrakis (pentafluorophenyl)borate.

In another embodiment, the metallocene catalyst compounds and CTA's described herein can be used with Bulky activators. A "Bulky activator" as used herein refers to anionic activators represented by the formula:

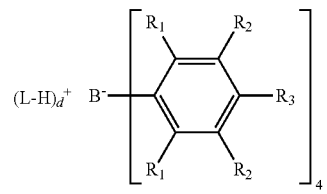

where:
each $R_1$ is, independently, a halide, preferably a fluoride;
each $R_2$ is, independently, a halide, a $C_6$ to $C_{20}$ substituted aromatic hydrocarbyl group or a siloxy group of the formula $-O-Si-R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula $-O-Si-R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);
L is an neutral Lewis base; (L-H)+ is a Bronsted acid; d is 1, 2, or 3;
wherein the anion has a molecular weight of greater than 1020 g/mol; and
wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: MV=8.3$V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
|---|---|
| H | 1 |
| 1$^{st}$ short period, Li to F | 2 |
| 2$^{nd}$ short period, Na to Cl | 4 |
| 1$^{st}$ long period, K to Br | 5 |
| 2$^{nd}$ long period, Rb to I | 7.5 |
| 3$^{rd}$ long period, Cs to Bi | 9 |

Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | MV Per subst. (Å$^3$) | Total MV (Å$^3$) |
|---|---|---|---|---|
| Dimethylanilinium tetrakis(perfluoronaphthyl)borate | [perfluoronaphthyl structure] | $C_{10}F_7$ | 261 | 1044 |
| Dimethylanilinium tetrakis(perfluorobiphenyl)borate | [perfluorobiphenyl structure] | $C_{12}F_9$ | 349 | 1396 |
| [4-tButyl-PhNMe$_2$H] [($C_6F_3(C_6F_5)_2)_4$B] | [perfluoroterphenyl structure] | $C_{18}F_{13}$ | 515 | 2060 |

Exemplary bulky activators useful in catalyst systems herein include: trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, [4-t-butyl-PhNMe$_2$H] [($C_6F_3(C_6F_5)_2)_4$B], and the types disclosed in U.S. Pat. No. 7,297,653.

Illustrative, but not limiting, examples of boron compounds which may be used as an activator in the processes of this invention are: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N- dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium) tetrakis(3,5-bis(trifluoromethyl)phenyl)borate, and dialkyl ammonium salts, such as: di-(i-propyl)ammonium tetrakis(pentafluorophenyl)borate, and dicyclohexylammonium tetrakis(pentafluorophenyl)borate; and additional tri-substituted phosphonium salts, such as tri(o-tolyl)phosphonium tetrakis(pentafluorophenyl)borate, and tri(2,6-dimethylphenyl)phosphonium tetrakis(pentafluorophenyl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4^-]$, $[Me_3NH^+][B(C_6F_5)_4^-]$; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

In a preferred embodiment, any of the activators described herein may be mixed together before or after combination with the catalyst compound(s), preferably before being mixed with the catalyst compound(s).

In some embodiments two NCA activators may be used in the polymerization and the molar ratio of the first NCA activator to the second NCA activator can be any ratio. In some embodiments, the molar ratio of the first NCA activator to the second NCA activator is 0.01:1 to 10,000:1, preferably 0.1:1 to 1000:1, preferably 1:1 to 100:1.

Further, the typical activator-to-catalyst ratio, e.g., all NCA activators-to-catalyst ratio is a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see for example, U.S. Pat. Nos. 5,153,157, 5,453,410, EP 0 573 120 B1, WO 94/07928, and WO 95/14044 which discuss the use of an alumoxane in combination with an ionizing activator).

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum and the like. Other oxophilic species such as diethyl zinc may be used.

Optional Support Materials

In embodiments herein, the catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. Most preferably the surface area of the support material is in the range is from about 100 to about 400 $m^2/g$, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2$/gm; pore volume of 1.65 $cm^3$/gm). Preferred silicas are marketed under the tradenames of DAVISON 952 or DAVISON 955 by the Davison Chemical Division of W.R. Grace and Company. In other embodiments DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the metallocene compound is then contacted with the isolated support/activator. In some embodiments, the supported catalyst system is generated in situ. In alternate embodiment, the slurry of the support material is first contacted with the catalyst compound for a period of time in the range of from about 0.5 hours to about 24 hours, from about 2 hours to about 16 hours, or from about 4 hours to about 8 hours. The slurry of the supported metallocene compound is then contacted with the activator solution.

The mixture of the metallocene, activator and support is heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In embodiments herein, the invention relates to polymerization processes where monomer (such as ethylene), and optionally comonomer, are contacted with a catalyst system comprising an activator and at least one metallocene compound, as described above. The catalyst compound and activator may be combined in any order, and are combined typically prior to contacting with the monomer.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene and isomers thereof.

In a preferred embodiment, the monomer comprises ethylene and an optional comonomers comprising one or more $C_3$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

In another preferred embodiment, the monomer comprises propylene and an optional comonomers comprising one or more of ethylene or $C_4$ to $C_{40}$ olefins, preferably ethylene or $C_4$ to $C_{20}$ olefins, or preferably ethylene or $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. divinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In some embodiments, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example, $C_4$ raffinate streams, and can therefore be substantially less expensive than pure 1-butene.

Preferably the comonomer(s) are present in the copolymer at less than 50 mol %, preferably from 0.5 to 45 mol %, preferably from 1 to 30 mol %, preferably from 3 to 25 mol %, preferably from 5 to 20 mol %, preferably from 7 to 15 mol %, with the balance of the copolymer being made up of the main monomer (such as ethylene or propylene).

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In a some embodiments hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In an alternate embodiment, the activity of the catalyst is at least 50 g/mmol/hour, preferably 500 or more g/mmol/hour, preferably 5000 or more g/mmol/hr, preferably 50,000 or more g/mmol/hr. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more.

In a preferred embodiment, little or no alumoxane is used in the process to produce the polymers. Preferably, alumoxane is present at zero mol %, alternately the alumoxane is present at a molar ratio of aluminum to transition metal less than 500:1, preferably less than 300:1, preferably less than 100:1, preferably less than 1:1.

In a preferred embodiment, little or no scavenger is used in the process to produce the ethylene polymer. Preferably, scavenger (such as tri alkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 0 to 300° C. (preferably 25 to 150° C., preferably 40 to 120° C., preferably 45 to 80° C.); 2) is conducted at a pressure of atmospheric pressure to 10 MPa (preferably 0.35 to 10 MPa, preferably from 0.45 to 6 MPa, preferably from 0.5 to 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); 4) wherein the catalyst system used in the polymerization comprises less than 0.5 mol %, preferably 0 mol % alumoxane, alternately the alumoxane is present at a molar ratio of aluminum to transition metal less than 500:1, preferably less than 300:1, preferably less than 100:1, preferably less than 1:1; 5) the polymerization preferably occurs in one reaction zone; 6) the productivity of the catalyst compound is at least 80,000 g/mmol/hr (preferably at least 150,000 g/mmol/hr, preferably at least 200,000 g/mmol/hr, preferably at least 250,000 g/mmol/hr, preferably at least 300,000 g/mmol/hr); 7) optionally scavengers (such as trialkyl aluminum compounds) are absent (e.g. present at zero mol %, alternately the scavenger is present at a molar ratio of scavenger metal to transition metal of less than 100:1, preferably less than 50:1, preferably less than 15:1, preferably less than 10:1); and 8) optionally hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)). In a preferred embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone. Room temperature is 23° C. unless otherwise noted.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

In a preferred embodiment of the invention, the polymerization occurs in a supercritical or supersolution state.

The terms "dense fluid" "solid-fluid phase transition temperature" "phase transition" "solid-fluid phase transition pressure" "fluid-fluid phase transition pressure" "fluid-fluid phase transition temperature" "cloud point" "cloud point pressure" "cloud point temperature" "supercritical state" "critical temperature (Tc)" "critical pressure (Pc)" "supercritical polymerization" "homogeneous polymerization" "homogeneous polymerization system" are defined in U.S. Pat. No. 7,812,104, which is incorporated by reference herein.

A supercritical polymerization means a polymerization process in which the polymerization system is in a dense (i.e. its density is 300 kg/m$^3$ or higher), supercritical state.

A super solution polymerization or supersolution polymerization system is one where the polymerization occurs at a temperature of 65° C. to 150° C. and a pressure of between 250 to 5,000 psi (1.72 to 34.5 MPa), preferably the super solution polymerization polymerizes a $C_2$ to $C_{20}$ monomer (preferably propylene), and has: 1) 0 to 20 wt % of one or more comonomers (based upon the weight of all monomers and comonomers present in the feed) selected from the group consisting of ethylene and $C_4$ to $C_{12}$ olefins, 2) from 20 to 65 wt % diluent or solvent, based upon the total weight of feeds to the polymerization reactor, 3) 0 to 5 wt % scavenger, based upon the total weight of feeds to the polymerization reactor, 4) the olefin monomers and any comonomers are present in the polymerization system at 15 wt % or more, 5) the polymerization temperature is above the solid-fluid phase transition temperature of the polymerization system and above a pressure greater than 1 MPa below the cloud point pressure of the polymerization system, provided however that the polymerization occurs: (1) at a temperature below the critical temperature of the polymerization system, or (2) at a pressure below the critical pressure of the polymerization system.

In a preferred embodiment of the invention, the polymerization process is conducted under homogeneous (such as solution, supersolution, or supercritical) conditions preferably including a temperature of about 60° C. to about 200° C., preferably for 65° C. to 195° C., preferably for 90° C. to 190° C., preferably from greater than 100° C. to about 180° C., such as 105° C. to 170° C., preferably from about 110° C. to about 160° C. The process may conducted at a pressure in excess of 1.7 MPa, especially under supersolution conditions including a pressure of between 1.7 MPa and 30 MPa, or especially under supercritical conditions including a pressure of between 15 MPa and 1500 MPa, especially when the monomer composition comprises propylene or a mixture of propylene with at least one $C_4$ to $C_{20}$ α-olefin. In a preferred embodiment the monomer is propylene and the propylene is present at 15 wt % or more in the polymerization system, preferably at 20 wt % or more, preferably at 30 wt % or more, preferably at 40 wt % or more, preferably at 50 wt % or more, preferably at 60 wt % or more, preferably at 70 wt % or more, preferably 80 wt % or more. In an alternate embodiment, the monomer and any comonomer present are present at 15 wt % or more in the polymerization system, preferably at 20 wt % or more, preferably at 30 wt % or more, preferably at 40 wt % or more, preferably at 50 wt % or more, preferably at 60 wt % or more, preferably at 70 wt % or more, preferably 80 wt % or more.

In a preferred embodiment of the invention, the polymerization process is conducted under supersolution conditions including temperatures from about 65° C. to about 150° C., preferably from about 75° C. to about 140° C., preferably from about 90° C. to about 140° C., more preferably from about 100° C. to about 140° C., and pressures of between 1.72 MPa and 35 MPa, preferably between 5 and 30 MPa.

In another particular embodiment of the invention, the polymerization process is conducted under supercritical conditions (preferably homogeneous supercritical conditions, e.g. above the supercritical point and above the cloud point) including temperatures from about 90° C. to about 200° C., and pressures of between 15 MPa and 1500 MPa, preferably between 20 MPa and 140 MPa.

A particular embodiment of this invention relates to a process to polymerize propylene comprising contacting, at a temperature of 60° C. or more and a pressure of between 15 MPa (150 Bar, or about 2175 psi) to 1500 MPa (15,000 Bar, or about 217,557 psi), one or more olefin monomers having three or more carbon atoms, with: 1) the catalyst system, 2) optionally one or more comonomers, 3) optionally diluent or solvent, and 4) optionally scavenger, wherein: a) the olefin monomers and any comonomers are present in the polymerization system at 40 wt % or more, b) the propylene is present at 80 wt % or more based upon the weight of all monomers and comonomers present in the feed, c) the polymerization occurs at a temperature above the solid-fluid phase transition temperature of the polymerization system and a pressure no lower than 2 MPa below the cloud point pressure of the polymerization system.

Another particular embodiment of this invention relates to a process to polymerize olefins comprising contacting propylene, at a temperature of 65° C. to 150° C. and a pressure of between 250 to 5,000 psi (1.72 to 34.5 MPa), with: 1) the catalyst system, 2) 0 to 20 wt % of one or more comonomers (based upon the weight of all monomers and comonomers present in the feed) selected from the group consisting of ethylene and $C_4$ to $C_{12}$ olefins, 3) from 20 to 65 wt % diluent or solvent, based upon the total weight of feeds to the polymerization reactor, and 4) 0 to 5 wt % scavenger, based upon the total weight of feeds to the polymerization reactor, wherein: a) the olefin monomers and any comonomers are present in the polymerization system at 15 wt % or more, b) the propylene is present at 80 wt % or more based upon the weight of all monomers and comonomers present in the feed, c) the polymerization occurs at a temperature above the solid-fluid phase transition temperature of the polymerization system and above a pressure greater than 1 MPa below the cloud point pressure of the polymerization system, provided however that the polymerization occurs: (1) at a temperature below the critical temperature of the polymerization system, or (2) at a pressure below the critical pressure of the polymerization system.

In another embodiment, the polymerization occurs at a temperature above the solid-fluid phase transition temperature of the polymerization system and a pressure no lower than 10 MPa below the cloud point pressure (CPP) of the polymerization system (preferably no lower than 8 MPa below the CPP, preferably no lower than 6 MPa below the CPP, preferably no lower than 4 MPa below the CPP, preferably no lower than 2 MPa below the CPP). Preferably, the polymerization occurs at a temperature and pressure above the solid-fluid phase transition temperature and pressure of the polymerization system and, preferably above the fluid-fluid phase transition temperature and pressure of the polymerization system.

In an alternate embodiment, the polymerization occurs at a temperature above the solid-fluid phase transition temperature of the polymerization system and a pressure greater than 1 MPa below the cloud point pressure (CPP) of the polymerization system (preferably greater than 0.5 MPa below the CPP, preferably greater than the CCP), and the polymerization occurs: (1) at a temperature below the critical temperature of the polymerization system, or (2) at a pressure below the critical pressure of the polymerization system, preferably the polymerization occurs at a pressure and temperature below the critical point of the polymerization system, most preferably the polymerization occurs: (1) at a temperature below the critical temperature of the polymerization system, and (2) at a pressure below the critical pressure of the polymerization system.

Alternately, the polymerization occurs at a temperature and pressure above the solid-fluid phase transition temperature and pressure of the polymerization system. Alternately, the polymerization occurs at a temperature and pressure above the fluid-fluid phase transition temperature and pressure of the polymerization system. Alternately, the polymerization occurs at a temperature and pressure below the fluid-fluid phase transition temperature and pressure of the polymerization system.

In another embodiment, the polymerization system is preferably a homogeneous, single phase polymerization system, preferably a homogeneous dense fluid polymerization system.

In another embodiment, the reaction temperature is preferably below the critical temperature of the polymerization system. Preferably, the temperature is above the solid-fluid phase transition temperature of the polymer-containing fluid reaction medium at the reactor pressure or at least 5° C. above the solid-fluid phase transition temperature of the polymer-containing fluid reaction medium at the reactor pressure, or at least 10° C. above the solid-fluid phase transformation point of the polymer-containing fluid reaction medium at the reactor pressure. In another embodiment, the temperature is above the cloud point of the single-phase fluid reaction medium at the reactor pressure, or 2° C. or more above the cloud point of the fluid reaction medium at the reactor pressure. In yet another embodiment, the temperature is between 60° C. and 150° C., between 60° C. and 140° C., between 70° C. and 130° C., or between 80° C. and 130° C. In one embodiment, the temperature is above 60° C., 65° C., 70° C., 75° C., 80° C., 85° C., 90° C., 95° C., 100° C., 105° C., or 110° C. In another embodiment, the temperature is below 150° C., 140° C., 130° C., or 120° C. In another embodiment, the cloud point temperature is below the supercritical temperature of the polymerization system or between 70° C. and 150° C.

In another embodiment, the polymerization occurs at a temperature and pressure above the solid-fluid phase transition temperature of the polymerization system, preferably the polymerization occurs at a temperature at least 5° C. higher (preferably at least 10° C. higher, preferably at least 20° C. higher) than the solid-fluid phase transition temperature and at a pressure at least 2 MPa higher (preferably at least 5 MPa higher, preferably at least 10 MPa higher) than the cloud point pressure of the polymerization system. In a preferred embodiment, the polymerization occurs at a pressure above the fluid-fluid phase transition pressure of the polymerization system (preferably at least 2 MPa higher, preferably at least 5 MPa higher, preferably at least 10 MPa higher than the fluid-fluid phase transition pressure). Alternately, the polymerization occurs at a temperature at least 5° C. higher (preferably at least 10° C. higher, preferably at least 20° C. higher) than the solid-fluid phase transition temperature and at a pressure higher than, (preferably at least 2 MPa higher, preferably at least 5 MPa higher, preferably at least 10 MPa higher) than the fluid-fluid phase transition pressure of the polymerization system.

In another embodiment, the polymerization occurs at a temperature above the solid-fluid phase transition temperature of the polymer-containing fluid reaction medium at the reactor pressure, preferably at least 5° C. above the solid-fluid phase transition temperature of the polymer-containing fluid reaction medium at the reactor pressure, or preferably at least 10° C. above the solid-fluid phase transformation point of the polymer-containing fluid reaction medium at the reactor pressure.

In another useful embodiment, the polymerization occurs at a temperature above the cloud point of the single-phase fluid reaction medium at the reactor pressure, more preferably 2° C. or more (preferably 5° C. or more, preferably 10° C. or more, preferably 30° C. or more) above the cloud point of the fluid reaction medium at the reactor pressure. Alternately, in another useful embodiment, the polymerization occurs at a temperature above the cloud point of the polymerization system at the reactor pressure, more preferably 2° C. or more (preferably 5° C. or more, preferably 10° C. or more, preferably 30° C. or more) above the cloud point of the polymerization system.

In another embodiment, the polymerization process temperature is above the solid-fluid phase transition temperature of the polymer-containing fluid polymerization system at the reactor pressure, or at least 2° C. above the solid-fluid phase transition temperature of the polymer-containing fluid polymerization system at the reactor pressure, or at least 5° C. above the solid-fluid phase transition temperature of the polymer-containing fluid polymerization at the reactor pressure, or at least 10° C. above the solid-fluid phase transformation point of the polymer-containing fluid polymerization system at the reactor pressure. In another embodiment, the polymerization process temperature should be above the cloud point of the single-phase fluid polymerization system at the reactor pressure, or 2° C. or more above the cloud point of the fluid polymerization system at the reactor pressure. In still another embodiment, the polymerization process temperature is between 50° C. and 350° C., or between 60° C. and 250° C., or between 70° C. and 250° C., or between 80° C. and 250° C. Exemplary lower polymerization temperature limits are 50° C., or 60° C., or 70° C., or 80° C., or 90° C., or 95° C., or 100° C., or 110° C., or 120° C. Exemplary upper polymerization temperature limits are 350° C., or 250° C., or 240° C., or 230° C., or 220° C., or 210° C., or 200° C.

Polyolefin Products

This invention also relates to compositions of matter produced by the methods described herein.

In a preferred embodiment of the invention, the process described herein produces ethylene homopolymers or ethylene copolymers, such as ethylene-alphaolefin (preferably $C_3$ to $C_{20}$) copolymers (such as ethylene-propylene copolymers, ethylene-hexene copolymers or ethylene-octene copolymers) having: a Mw/Mn of greater than 1 to 4 (preferably greater than 1 to 3).

In a preferred embodiment of the invention, the process described herein produces propylene homopolymers or propylene copolymers, such as propylene-alphaolefin (preferably ethylene or $C_4$ to $C_{20}$) copolymers (such as propylene-ethylene copolymers, propylene-hexene copolymers or propylene-octene copolymers) having: a Mw/Mn of greater than 1 to 4 (preferably greater than 1 to 3).

Likewise, the process of this invention produces olefin polymers, preferably polyethylene and polypropylene homopolymers and copolymers. In a preferred embodiment, the polymers produced herein are homopolymers of ethylene or propylene, are copolymers of ethylene preferably having from 0 to 25 mole % (alternately from 0.5 to 20 mole %, alternately from 1 to 15 mole %, preferably from 3 to 10 mole %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene), or are copolymers of propylene preferably having from 0 to 25 mole % (alternately from 0.5 to 20 mole %, alternately from 1 to 15 mole %, preferably from 3 to 10 mole %) of one or more of $C_2$ or $C_4$ to $C_{20}$ olefin comonomer (preferably ethylene or $C_4$ to $C_{12}$ alpha-olefin, preferably ethylene, butene, hexene, octene, decene, dodecene, preferably ethylene, butene, hexene, octene).

Polypropylene homopolymers produced may be isotactic, atactic, hemiisotactic or syndiotactic. The structure produced is influenced by the catalyst choosen.

In a preferred embodiment, the monomer is ethylene and the comonomer is hexene, preferably from 1 to 15 mole % hexene, alternately 1 to 10 mole %.

Typically, the polymers produced herein have an Mw of 5,000 to 1,000,000 g/mol (preferably 25,000 to 750,000 g/mol, preferably 50,000 to 500,000 g/mol), and/or an Mw/Mn of greater than 1 to 40 (alternately 1.2 to 20, alternately 1.3 to 10, alternately 1.4 to 5, 1.5 to 4, ultimately 1.5 to 3).

In a preferred embodiment the polymer produced herein has a unimodal or multimodal molecular weight distribution as determined by Gel Permeation Chromotography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

Unless otherwise indicated, Mw, Mn, MWD (Mw/Mn) are determined by GPC as described in US 2006/0173123 page 24-25, paragraphs [0334] to [0341].

In a preferred embodiment the polymer produced herein has a composition distribution breadth index (CDBI) of 50% or more, preferably 60% or more, preferably 70% or more. CDBI is a measure of the composition distribution of monomer within the polymer chains and is measured by the procedure described in PCT publication WO 93/03093, published Feb. 18, 1993, specifically columns 7 and 8 as well as in Wild et al, J. Poly. Sci., Poly. Phys. Ed., Vol. 20, p. 441 (1982) and U.S. Pat. No. 5,008,204, including that fractions having a weight average molecular weight (Mw) below 15,000 are ignored when determining CDBI.

Blends

In another embodiment, the polymer (preferably the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Specifically, any of the foregoing polymers, including blends thereof, may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15, preferably 7 to 9. However, in another embodiment the film is oriented to the same extent in both the MD and TD directions.

The films may vary in thickness depending on the intended application; however, films of a thickness from 1 to 50 µm are usually suitable. Films intended for packaging are usually from 10 to 50 µm thick. The thickness of the sealing layer is typically 0.2 to 50 µm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

Molded Products

The polymers described herein (preferably propylene polymers) and blends thereof may also be used to prepare molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

Further, the polymers described herein (preferably propylene polymers) may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. Typically, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The tool stays closed to cool the film and the tool is then opened. The shaped laminate is then removed from the tool. The thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution.

Blow molding is another suitable forming means for use with the compositions of this invention, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING pp. 90-92 (Jacqueline I. Kroschwitz, ed., John Wiley & Sons 1990).

Likewise, molded articles may be fabricated by injecting molten polymer into a mold that shapes and solidifies the molten polymer into desirable geometry and thickness of molded articles. Sheets may be made either by extruding a substantially flat profile from a die, onto a chill roll, or alternatively by calendaring. Sheets are generally considered to have a thickness of from 10 mils to 100 mils (254 μm to 2540 μm), although any given sheet may be substantially thicker.

Non-Wovens and Fibers

The polymers produced herein may also be used to prepare nonwoven fabrics and fibers in any nonwoven fabric and fiber making process, including but not limited to, melt blowing, spunbonding, film aperturing, and staple fiber carding. A continuous filament process may also be used. Preferably a spunbonding process is used. The spunbonding process is well known in the art. Generally it involves the extrusion of fibers through a spinneret. These fibers are then drawn using high velocity air and laid on an endless belt. A calendar roll is generally then used to heat the web and bond the fibers to one another although other techniques may be used such as sonic bonding and adhesive bonding.

In another embodiment, this invention relates to:

1. A metallocene compound represented by the formula (1): $A_eMX_{n-e}$, or the formula (1c) $TA_2MX_{n-2}$, wherein: e is 1 or 2; T is a bridging group between two A groups; each A is a substituted monocyclic or polycyclic ligand that is pi-bonded to M and optionally includes one or more ring heteroatoms selected from boron, a group 14 atom that is not carbon, a group 15 atom, or a group 16 atom, and when e is 2 each A may be the same or different, provided that at least one A is substituted with at least one cyclopropyl substituent directly bonded to any $sp^2$ carbon atom at a bondable ring position of the ligand, wherein the cyclopropyl substituent is represented by the formula:

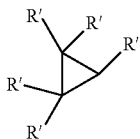

where each R' is, independently, hydrogen, a substituted or unsubstituted hydrocarbyl group, or a halogen; M is a transition metal atom having a coordination number of n and selected from group 3, 4, or 5 of the Periodic Table of Elements, or a lanthanide metal atom, or actinide metal atom; n is 3, 4, or 5; and each X is a univalent anionic ligand, or two Xs are joined and bound to the metal atom to form a metallocycle ring, or two Xs are joined to form a chelating ligand, a diene ligand, or an alkylidene ligand.

2. The metallocene compound of paragraph 1, where the compound is represented by the formula: $Ty(A)_e(E)MX_{n-e-1}$ where E is $J-R''_{x-1-y}$, J is a heteroatom with a coordination number of three from group 15 or with a coordination number of two from group 16 of the Periodic Table of Elements; R" is a $C_1-C_{100}$ substituted or unsubstituted hydrocarbyl radical; x is the coordination number of the heteroatom J where "x-1-y" indicates the number of R" substituents bonded to J; T is a bridging group between A and E, A and E are bound to M, y is 0 or 1; and A, e, M, X and n are as defined in paragraph 1.

3. The metallocene compound of paragraph 1 or 2, wherein the metallocene compound is represented by one of the following formulae:

formula (1a)

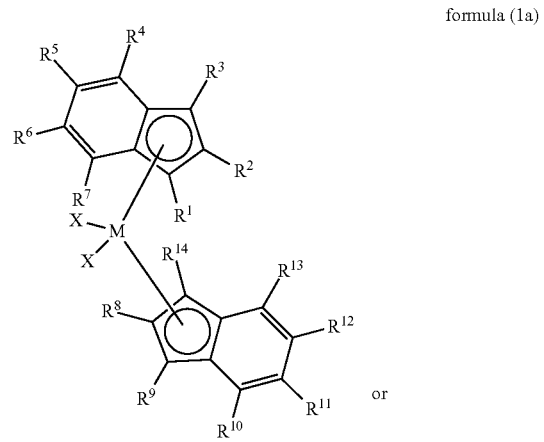

or formula (1b)

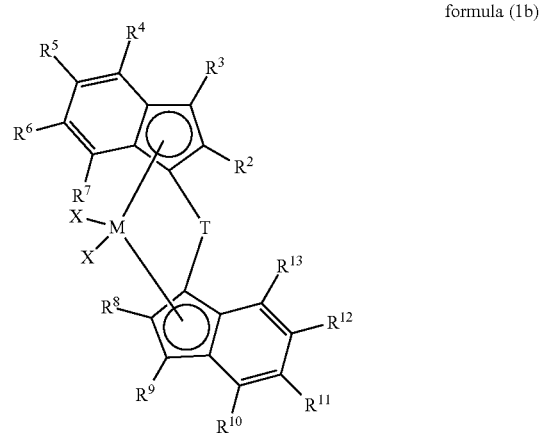

formula (2a)

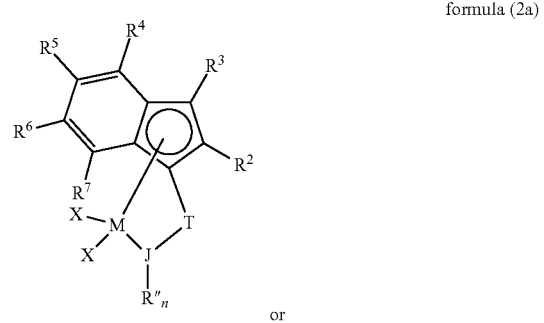

or formula (2b)

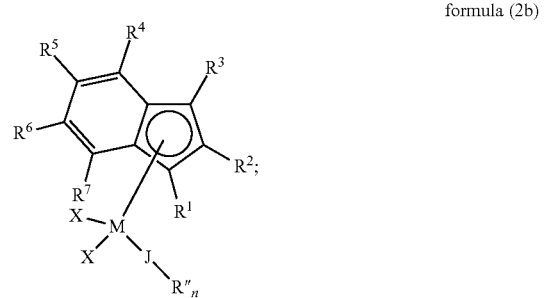

where M, T, X, are as defined in paragraph 1; J, R'', and n are as defined in paragraph 2, and each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is, independently, hydrogen, a substituted hydrocarbyl group, an unsubstituted hydrocarbyl group, or a halide, provided that in formula 1a and 1b, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ is a cyclopropyl substituent and in formula 2a and 2b at least one of $R^1$, $R^2$, $R^3$, $R^4$, $R^5$, $R^6$, or $R^7$, is a cyclopropyl substituent; and provided that any adjacent $R^1$ to $R^{14}$ groups that are not a cyclopropyl substituent may form a fused ring or multicenter fused ring system where the rings may be aromatic, partially saturated or saturated.

4. The metallocene compound of paragraph 1 or 2, wherein at least one A is monocyclic ligand selected from the group consisting of substituted or unsubstituted cyclopentadienyl, heterocyclopentadienyl, and heterophenyl ligands provided that when e is one, the monocyclic ligand is substituted with at least one cyclopropyl substituent.

5. The metallocene compound of paragraph 1 or 2, wherein at least one A is a polycyclic ligand selected from the group consisting of substituted or unsubstituted indenyl, fluorenyl, cyclopenta[a]naphthyl, cyclopenta[b]naphthyl, heteropentalenyl, heterocyclopentapentalenyl, heteroindenyl, heterofluorenyl, heterocyclopentanaphthyl, heterocyclopentaindenyl, and heterobenzocyclopentaindenyl ligands, provided that when e is one, the polycyclic ligand is substituted with at least one cyclopropyl substituent.

6. The metallocene compound of paragraph 1, 2, 3, 4, or 5 wherein M is a group 4 metal, preferably Hf, Ti or Zr.

7. The metallocene compound of any of paragraphs 1 to 6, wherein each R' is hydrogen.

8. The metallocene compound of any of paragraphs 1 to 7, wherein at least one A is a substituted or unsubstituted indenyl ligand, provided that when e is one, the indenyl ligand is substituted with at least one cyclopropyl substituent, preferably in the 2 and/or 4 positions.

9. The metallocene compound of any of paragraphs 2 to 8, wherein T is represented by the formula, $(R'''_2G)_g$, where each G is C, Si, or Ge, g is 1 or 2, and each R''' is, independently, hydrogen, halogen, $C_1$ to $C_{20}$ hydrocarbyl or a $C_1$ to $C_{20}$ substituted hydrocarbyl, and two or more R''' can form a cyclic structure including aromatic, partially saturated, or saturated cyclic or fused ring system.

10. The metallocene compound of any of paragraphs 3 to 9 wherein $R^2$ and/or $R^8$ are cyclopropyl substituents and/or $R^4$ and/or $R^{10}$ are cyclopropyl substituents.

11. The metallocene compound of any of paragraphs 3 to 10 wherein when one of $R^1$, $R^2$, $R^3$, $R^4$, $R^5$, $R^6$, and $R^7$ is a cyclopropyl substituent, at least one of the other $R^1$ to $R^7$ substitutents is not hydrogen, and when one of $R^8$, $R^9$, $R^{10}$, $R^{11}$, $R^{12}$, $R^{13}$, and $R^{14}$ is a cyclopropyl substituent, at least one of the other $R^8$ to $R^{14}$ groups is not hydrogen.

12. The metallocene of compound any of paragraphs 3 to 11 wherein $R^2$ and $R^8$ are cyclopropyl and/or $R^4$ and/or $R^{10}$ are hydrocarbyl or halogen.

13. The metallocene compound of any of paragraphs 3 to 12 where in J is nitrogen, phosphorus, oxygen or sulfur.

14. The metallocene catalyst compound of paragraph 1 wherein the metallocene compound is one or more of: dimethylsilylene-bis(2-cyclopropyl-4-carbazol-9-ylindenyl)zirconium dichloride; dimethylsilylene-bis(2-cyclopropyl-4-naphth-1-ylindenyl)zirconium dichloride; dimethylsilyl(2-cyclopropyl-4-carbazol-9-ylindenyl)(2-cyclopropyl-4-phenylindenyl)zirconium dichloride; dimethylsilylene-(2-cyclopropyl-4-carbazol-9-ylindenyl)(2-methyl-4-phenylindenyl) zirconium dichloride; bis(2-cyclopropylindenyl)zirconium dichloride; dimethylsilylene-(2-cyclopropylindenyl)(tert-butylamido)zirconium dichloride; dimethylsilylene-(2-cyclopropylindenyl)(tert-butylamido)titanium dichloride; dimethylsilylene-bis(2-cyclopropyl-4-para-tert-butylphenylindenyl)zirconium dichloride; dimethylsilylene-bis(2-cyclopropyl-4-naphth-1-ylindenyl)hafnium dichloride; dimethylsilylene-bis(2-cyclopropyl-4-chloroindenyl)zirconium dichloride; dimethylsilylene-bis(2-cyclopropyl-4,7-dimethylindenyl) zirconium dichloride; dimethylsilylene-bis(2-cyclopropyl-4,7-dimethylindenyl)hafnium dichloride; dimethylsilylene-bis (2-cyclopropyl-4-carbazol-9-ylindenyl)hafnium dichloride; dimethylsilylene-bis(2-methyl-4-cyclopropylindenyl)zirconium dichloride; cyclotetramethylenesilylene-(2-cyclopropyl-4-phenylindenyl)(2-cyclopropyl-4-carbazol-9-ylindenyl) zirconium dichloride; dimethylsilylene-bis(2-cyclopropyl-4-phenylindenyl)zirconium dichloride; dimethylsilylene-(2-cyclopropyl-4-para-tert-butylphenylindenyl)(2-methyl-4-phenylindenyl)zirconium dichloride; dimethylsilylene-bis(2-cyclopropyl-4-para-tert-butylphenylindenyl)hafnium dichloride; cyclotetramethylenesilylene-(bis(2-methyl-4-cyclopropylindenyl)zirconium dichloride; dimethylsilylene-bis(2,4-dicyclopropylindenyl) zirconium dichloride; dimethylsilylene-bis(2-methyl-4-cyclopropylindenyl)hafnium dichloride; where, in alternate embodiments, the dichloride in any of the compounds listed above may be replaced with dialkyl, dialkaryl, diflouride, diiodide, or dibromide, or a combination thereof.

15. A catalyst system comprising activator and the metallocene catalyst compound of any of paragraph 1 to 14.

16. The catalyst system of paragraph 15 wherein the activator comprises alumoxane or a non-coordinating anion activator.

17. The catalyst system of paragraph 15 wherein the activator is one or more of any of the activators named in this specification.

18. The catalyst system of paragraph 15 wherein the catalyst system is supported, preferably on silica.

19. A process to polymerize olefins comprising contacting one or more olefins with the catalyst system any of claims 15 to 18.

20. The process of paragraph 19 wherein the process occurs in solution, preferably at a temperature of from about 0° C. to about 300° C., at a pressure in the range of from about 0.35 MPa to about 10 MPa, and at a time up to 300 minutes.

21. The process of paragraph 20 further comprising obtaining polymer, preferably polymer comprising ethylene and or propylene.

22. The process of paragraph 20 or 21 wherein an ethylene polymer (preferably a homopolymer of ethylene or a copolymer of ethylene and one or more of propylene, butene, hexene or octene) is obtained.

23. The process of paragraph 20 or 21 wherein a propylene polymer (preferably a homopolymer of propylene or a copolymer of propylene and one or more of ethylene, butene, hexene or octene) is obtained.

24. The process of paragraph 20 or 21 wherein an isotactic polymer is obtained, preferably an isotactic propylene polymer.

EXPERIMENTAL

Starting Materials

9H-Carbazole (Merck), p-toluenesulfonic acid (TsOH, Aldrich), 2.5 M ⁿBuLi in hexanes (Chemetall GmbH), MeMgBr in ether (Aldrich), 4-ᵗBuC$_6$H$_4$MgBr in ether (Aldrich), TiCl$_4$ (Merck), ZrCl$_4$(THF)$_2$ (Strem), HfCl$_4$(THF)$_2$ (Strem), lithium tert-butoxide (Aldrich), bis(dibenzylideneacetone)palladium(0) (pd(dba)$_2$, Strem), P$^t$Bu$_3$ (Strem), Celite 545 (Aldrich), Na$_2$SO$_4$ (Akzo Nobel), 2-chlorobenzyl chloride (Merck), 1-bromonaphthalene (Acros), bromobenzene (Acros), anhydrous ethanol (Merck), 96% ethanol (Merck), sodium lump (Merck), diethyl malonate (Acros), potassium hydroxide (Merck), thionyl chloride (Merck), AlCl$_3$ (Merck), 37% hydrochloric acid (Merck), dichloromethane (Merck), n-hexane (Merck), hexanes (Merck), dimethoxyethane (DME, Merck), toluene (Merck), ethyl acetate (Merck), dimethylsulfoxide (DMSO, Merck), NH$_4$Cl (Merck), NaBH$_4$ (Aldrich), MgSO$_4$ (Merck), CuCN (Merck), N-bromosuccinimide (NBS, Alfa Aesar), methylcyclohexane (Merck), silica gel 60 (40-63 um; Merck), NaHCO$_3$ (Merck) and CDCl$_3$ (Deutero GmbH) were used as received. tert-butylamine (Merck) was dried over CaH$_2$ before use. Dichlorodimethylsilane (Merck) was distilled in argon atmosphere before use. Tetrahydrofuran (THF, Merck) and ether (Merck) freshly distilled from benzophenone ketyl were used for organometallic synthesis and catalysis. Toluene (Merck) and n-hexane (Merck) for organometallic synthesis were distilled over Na/K alloy. Dichloromethane for organometallic synthesis and dichloromethane-d2 for NMR measurements were distilled over P$_4$O$_{10}$ before use. Brine used means the saturated aqueous solution of NaCl (Merck), i.e. solution of ca. 36 g of NaCl in 100 ml of water at room temperature. 2-Bromo-1H-indene and 2-bromo-4,7-dimethyl-1H-indene were obtained as described in [Voets, M.; Antes, I.; Scherer, C.; Mueller-Vieira, U.; Biemel, K.; Marchais-Oberwinkler, S.; Hartmann, R. W. J. Med. Chem. 2006, 49, 2222] and [Schumann, H.; Karasiak, D. F.; Muehle, S. H.; Halterman, R. L.; Kaminisky, W.; Weingarten, U. J. Organomet. Chem. 1999, 579, 356], respectively. 7-Bromo-2-methyl-1H-indene and 7-bromo-1H-indene were obtained as described in [Izmer, V. V.; Lebedev, A. Y.; Nikulin, M. V.; Ryabov, A. N.; Asachenko, A. F.; Lygin, A. V.; Sorokin, D. A.; Voskoboynikov, A. Z. Organometallics, 2006, 1217] and [Adamczyk, M.; Watt, D. S.; Netzel, D. A. J. Org. Chem. 1984, 49, 4226], respectively. Chloro(2-methyl-4-phenyl-1H-inden-1-yl)dimethylsilane was obtained from 2-methyl-4-phenyl-1H-indene (Aldrich) as described in [Thomas, E. J.; Rausch, M. D.; Chien, J. C. W. J. Organomet. Chem. 2001, 631, 29]. 4-Bromo-1-methoxyindane was obtained as described in [Voskoboynikov, A. Z.; Izmer, V. V.; Asachenko, A. F.; Nikulin, M. V.; Ryabov, A. N.; Lebedev, A. Y.; Coker, C. L.; Canich, J. A. M. U.S. Pat. No. 7,763,562 Jul. 27, 2010. Cyclopropylmagnesium bromide ($^c$PrMgBr) and (1-methoxy-2,3-dihydro-1H-inden-4-yl)magnesium bromide were obtained from cyclopropylbromide (Aldrich) and 4-bromo-1-methoxyindane, respectively, and magnesium turnings (Acros) in THF. The latter was used as a 0.93 M solution of (1-methoxy-2,3-dihydro-1H-inden-4-yl)magnesium bromide in THF. 1,1-Dichlorosilolane was obtained as described in [Daiss, J. O.; Burschka, C.; Mills, J. S.; Montana, J. G.; Showell, G. A.; Wameck, J. B. H.; Tacke, R. Organometallics 2006, 25, 1188]. [1,3-Bis[2,6-diisopropylphenyl]-1,3-dihydro-2H-imidazol-2-ylidene][triphenylphosphine]nickel dichloride, complex "iPrNi", was obtained from Ni(PPh$_3$)$_2$Cl$_2$ and bis(2,6-diisopropylphenyl)imidazolium chloride as described in [Matsubara, K.; Ueno, K.; Shibata, Y. Organometallics 2006, 25, 3422 (compound 3a)]. Bis(2,6-diisopropylphenyl)imidazolium chloride and Ni(PPh$_3$)$_2$Cl$_2$ were obtained as described in [Arduengo, A. J., III; Dias, H. V. R.; Harlow, R. L.; Kline, M. J. Am. Chem. Soc. 1992, 114, 5530] and [Venanzi, L. M. J. Chem. Soc. 1958, 719], respectively.

Analytical and semi-preparative liquid chromatography was performed using a Waters Delta 600 HPLC system including a 996 Photodiode Array Detector, Nova-Pack C18 or HR Silica (60 Å, 6 μm, 3.9 and 19×300 mm) and Symmetry C18 (5 μm, 4.6×250 mm) columns. MPLC (Medium Pressure Liquid Chromatography, pressure 5-15 bars) was performed using MPLC glass columns and fittings (Ace Glass), a PD5130 pump drive equipped with a J1 gear-well pump head (Heidolph), a 996 Photodiode Array Detector and a Fraction Collector II (Waters Corp.). $^1$H and $^{13}$C spectra were recorded with a Brucker Avance-400 spectrometer. Chemical shifts for $^1$H and $^{13}$C were measured relative to tetramethylsilane (TMS). $^1$H NMR spectral assignments were made on the basis of double resonance and Nuclear Overhauser Effect (NOE) experiments. CHN microanalyses were done using a CHN—O-Rapid analyzer (Heraecus Ltd., Banau, Germany).

Example 1: Synthesis of bis(2-cyclopropylindenyl)zirconium dichloride (1)

2-Cyclopropyl-1H-indene

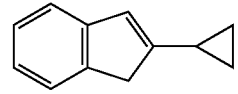 [SMILES: C1=C(C2CC2)Cc2ccccc21]

To a solution of 15.0 g (76.9 mmol) of 2-bromo-1H-indene in 200 ml of THF, 0.60 g (0.77 mmol) of "iPrNi" was added. This mixture was stirred for 5 minutes, and then 183 ml (115 mmol) of 0.63 M $^c$PrMgBr in THF was added dropwise by vigorous stirring for 10 minutes at room temperature. This mixture was stirred for 8 h at 60° C. and then poured into a mixture of 600 ml of water and 400 ml of hexane. The organic layer was separated, and the aqueous layer was extracted with 2×150 ml of hexane. The combined organic extract was dried over Na$_2$SO$_4$ and then evaporated to dryness. The crude product was purified by flash chromatography on silica gel 60 (40-63 um; eluent: hexanes). Yield 8.40 g (70%) of colorless oil. Calcd. for C$_{12}$H$_{12}$: C, 92.26; H, 7.74. Found: C, 92.03; H, 7.92. $^1$H NMR (CDCl$_3$): δ 7.37 (m, 1H, 4-H in indene), 7.21-7.27 (m, 2H, 5,7-H in indene), 7.11 (m, 1H, 6—H in indene), 6.53 (m, 1H, 3-H in indene), 3.22 (m, 2H, 1,1-H in indene), 1.86 (m, 1H, 1-H in $^c$Pr), 0.92 (m, 2H, 2,3-H in $^c$Pr), 0.69 (m, 2H, 2',3'-H in $^c$Pr).

Bis(2-cyclopropylindenyl)zirconium Dichloride (1)

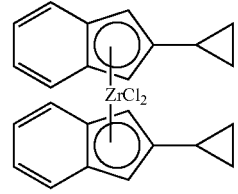

To a solution of 1.00 g (2.56 mmol) of 2-cyclopropyl-1H-indene in 60 ml of ether cooled to 0° C., 2.56 ml (6.40 mmol) of 2.5 M $^n$BuLi in hexanes was added dropwise. The resulting mixture was stirred for 12 h at room temperature, then cooled to −50° C., and 1.21 g (3.20 mmol) of ZrCl$_4$(THF)$_2$ was added. The obtained mixture was stirred overnight at room temperature and then filtered through glass frit (G3). The precipitate was poured into 50 ml of hot toluene, and the obtained suspension was filtered through a Celite pad. The filtrate was evaporated to ca. 15 ml and filtered through glass frit (G4). Crystals that precipitated from this filtrate at −30° C. were collected, washed by 10 ml of cold hexane, and dried in vacuum. Yield 2.11 g (70%) of yellow crystalline powder. Calcd. for $C_{24}H_{22}Cl_2Zr$: C, 61.00; H, 4.69. Found: C, 61.12; H, 4.88. $^1H$ NMR ($C_6D_6$): δ 7.36 (m, 4H, 4,7-H in indenyl), 6.90 (m, 4H, 5,6-H in indenyl), 5.58 (s, 4H, 1,3-H in indenyl), 1.74 (m, 2H, 1-H in $^cPr$), 0.69 (m, 4H, 2,3-H in $^cPr$), 0.35 (m, 4H, 2',3'-H in $^cPr$).

Example 2: Synthesis rac-dimethylsilylene-bis[4-(4-tert-butylphenyl)-2-cyclopropylinden-1-yl)]dimethylzirconium (2)

4/7-(4-tert-Butylphenyl)-1H-indene

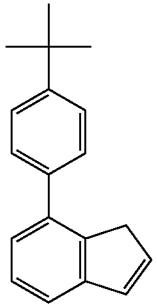

To a solution of 44.0 g (226 mmol) of 7-bromo-1H-indene in 400 ml of THF, 0.88 g (1.13 mmol) of "iPrNi" was added. This mixture was stirred for 5 minutes, and then 330 ml (290 mmol) of 0.88 M 4-$^tBuC_6H_4MgBr$ in THF was added dropwise by vigorous stirring for 30 minutes at room temperature. Further on, 0.40 g (0.51 mmol) of "iPrNi" was added. The resulting mixture was refluxed for 30 minutes, stirred for 12 h at 55° C., and then cooled to room temperature. Next, 300 ml of water was added, and the obtained mixture was acidified with 10% HCl to pH~6. The organic layer was separated, washed by aqueous $NaHCO_3$ and water, then dried over $Na_2SO_4$, and evaporated to dryness. The residue was distilled in vacuum, b.p. 180-185° C./0.5 mm Hg. Yield 31.0 g (55%) of colorless oil as a ca. 1 to 1 mixture of isomeric compounds. Calcd. for $C_{19}H_{20}$: C, 91.88; H, 8.12. Found: C, 91.75; H, 8.22. $^1H$ NMR ($CDCl_3$): δ 7.24-7.56 (m), 7.12 (m), 6.96 (m), 6.60 (m), 3.52 (m), 3.49 (m), 1.41 (s).

2-Bromo-4/7-(4-tert-butylphenyl)indan-1-ol

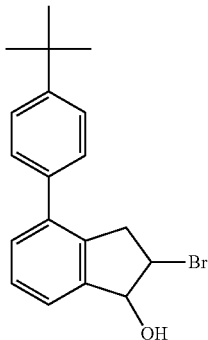 [SMILES: CC(C)(C)c1ccc(-c2cccc3c2CC(Br)C3O)cc1]

To a mixture of 30.0 g (121 mmol) of 4/7-(4-tert-butylphenyl)-1H-indene, 4.50 ml (250 mmol) of water, 200 ml of DMSO, and 100 ml of THF cooled to 0° C., 22.6 g (127 mmol) of N-bromosuccinimide was added in small portions by vigorous stirring during 1 h. The obtained mixture was stirred for 12 h at room temperature. Further on, one more portion of 11 g (61.8 mmol) of N-bromosuccinimide was added, and the reaction mixture was stirred for 72 h. After that it was diluted with 1000 ml of water, and crude product was extracted with 3×100 ml of ether. The combined organic extract was washed with 5×100 ml of water, dried over $Na_2SO_4$, and evaporated to dryness. The residue was purified by flash chromatography on silica gel 60 (40-63 um; eluent: hexanes-ethyl acetate=10:1 and then 2:1, vol.). Yield 37.7 g (90%) of orange oil of a ca. 1 to 1 mixture of two isomeric compounds. A sample of this mixture was separated by semi-preparative HPLC to characterize each isomer by NMR spectroscopy. Calcd. for $C_{19}H_{21}BrO$: C, 66.09; H, 6.13. Found: C, 65.84; H, 6.22. 2-Bromo-4-(4-tert-butylphenyl)indan-1-ol. $^1H$ NMR ($CDCl_3$): δ 7.44-7.48 (m, 2H, 2,6-H in 4-$^tBuC_6H_4$), 7.35-7.40 (m, 3H, 5,6,7-H in indane), 7.32-7.35 (m, 2H, 3,5-H in 4-$^tBuC_6H_4$), 5.36 (d, J=6.2 Hz, 1H, 1-H in indane), 4.21 (m, 1H, 2-H in indane), 3.60 (dd, J=16.2 Hz, J=7.2 Hz, 1H, 3-H in indane), 3.34 (dd, J=16.2 Hz, J=7.8 Hz, 1H, 3'-H in indane), 2.53 (br.s, 1H, OH), 1.37 (s, 9H, $^tBu$). 2-Bromo-7-(4-tert-butylphenyl)indan-1-ol. $^1H$ NMR ($CDCl_3$): δ 7.49 (m, 4H, 2,3,5,6-H in 4-$^tBuC_6H_4$), 7.38 (m, 1H, 5-H in indane), 7.29 (m, 1H, 6-H in indane), 7.25 (m, 1H, 4-H in indane), 5.50 (br.s, 1H, 1-H in indane), 4.42 (ddd, J=6.2 Hz, J=3.8 Hz, J=3.0 Hz, 1H, 2-H in indane), 3.82 (dd, J=17.0 Hz, J=6.2 Hz, 1H, 3-H in indane), 3.27 (dd, J=17.0 Hz, J=3.8 Hz, 1H, 3'-H in indane), 2.11 (br.s, 1H, OH), 1.38 (s, 9H, $^tBu$).

2-Bromo-4/7-(4-tert-butylphenyl)-1H-indene

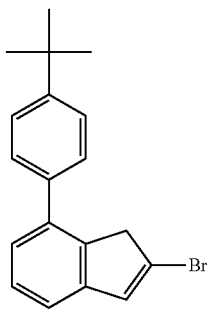 [SMILES: CC(C)(C)c1ccc(-c2cccc3c2CC(Br)=C3)cc1]

A solution of 36.0 g (104 mmol) of 2-bromo-4/7-(4-tert-butylphenyl)indan-1-ol and 0.1 g of p-toluenesulfonic acid in 100 ml of toluene was refluxed with a Dean-Stark head for 6 h. The resulting solution was cooled, passed through a pad of silica gel 60 (40-63 um), and then evaporated to dryness. The residue was purified by flash chromatography on silica gel 60 (40-63 um; eluent: hexanes-dichloromethane=5:1, vol.). Yield 16.0 g (47%) of yellow oil which crystallizes at room temperature. Calcd. for $C_{19}H_{19}Br$: C, 69.73; H, 5.85. Found: C, 69.99; H, 6.12. $^1H$ NMR ($CDCl_3$): δ 7.21-7.50 (m, 7H, 4,5,6-H in indane and 2,3,5,6-H in 4-$^tBuC_6H_4$), 7.14 (m, 1H, 3-H in indane), 3.70 (m, 2H, 1,1-H in indane), 1.38 (s, 9H, $^tBu$).

4/7-(4-tert-Butylphenyl)-2-cyclopropyl-1H-indene

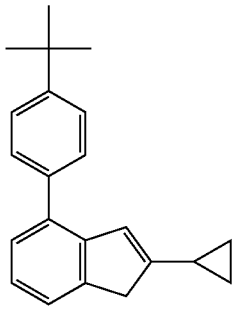 [SMILES: CC(C)(C)c1ccc(-c2cccc3c2C=C(C2CC2)C3)cc1]

To a solution of 18.0 g (55.0 mmol) of 2-bromo-4/7-(4-tert-butylphenyl)-1H-indene in 300 ml of THF, 0.23 g (0.30 mmol) of "iPrNi" was added. This mixture was stirred for 5 minutes at room temperature, and then 138 ml (82.5 mmol) of 0.60 M $^c$PrMgBr in THF was added dropwise for 10 minutes. The resulting mixture was stirred for 8 h at 60° C., then poured into a mixture of 600 ml of water and 400 ml of hexane. The organic layer was separated, and the aqueous layer was extracted with 2×150 ml of hexane. The combined organic extract was dried over $Na_2SO_4$ and evaporated to dryness. The residue was purified by flash chromatography on silica gel 60 (40-63 um; eluent: hexanes). Yield 6.00 g (38%) of colorless oil of a ca. 1 to 1 mixture of two isomers. Calcd. for $C_{22}H_{24}$: C, 91.61; H, 8.39. Found: C, 91.44; H, 8.32. $^1$H NMR (CDCl$_3$): δ 7.46-7.50 (m, 8H, 4-$^t$BuC$_6$H$_4$ of both isomers), 7.13-7.35 (m, 3H, C$_6$H$_3$ in indene of both isomers), 6.75 (s, 1H, 3-H in indene of isomer A), 6.68 (s, 1H, 3-H in indene of isomer B), 3.32 (s, 2H, 1,1-H in indene of isomer B), 3.28 (s, 2H, 1,1-H in indene of isomer A), 1.83 (m, 2H, 1-H in $^c$Pr of both isomers), 1.40 (s, 18H, $^t$Bu of both isomers), 0.89 (m, 4H, 2,3-H in $^c$Pr of both isomers), 0.66 (m, 4H, 2',3'-H in $^c$Pr of both isomers).

Bis[4-(4-tert-butylphenyl)-2-cyclopropyl-1H-inden-1-yl](dimethyl)silane

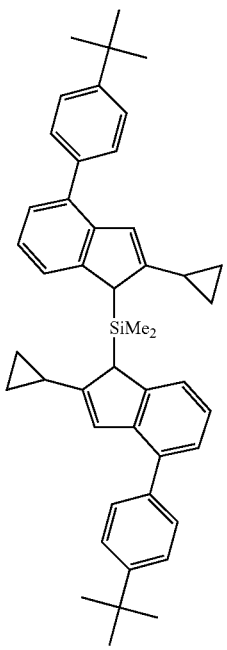

To a solution of 5.00 g (17.4 mmol) of 4/7-(4-tert-butylphenyl)-2-cyclopropyl-1H-indene in 30 ml of ether cooled to 0° C., 6.96 ml (17.4 mmol) of 2.5 M $^n$BuLi in hexanes was added. The resulting mixture was stirred for 3 h at room temperature. Further on, 5 ml of THF was added, the obtained mixture was cooled to −60° C., and 0.09 g (1.0 mmol) of CuCN was added. This mixture was allowed to warm to −30° C., stirred for 2 h at this temperature, then cooled to −60° C., and 1.05 ml (1.12 g, 8.70 mmol) of dichlorodimethylsilane was added. The resulting mixture was stirred for 12 h at room temperature, then 20 ml of water was added, and the organic phase was separated. The aqueous layer was extracted with 2×50 ml of ethyl acetate. The combined organic extract was dried over $MgSO_4$ and evaporated to dryness. The residue was purified by flash chromatography on silica gel 60 (40-63 um; eluent: hexanes and then hexanes-dichloromethane=50:1, vol.). Yield 4.50 g (82%) of yellow glassy solid of a ca. 2 to 1 mixture of meso- and rac-compounds. Calcd. for $C_{46}H_{52}Si$: C, 87.28; H, 8.28. Found: C, 87.44; H, 8.42. $^1$H NMR (CDCl$_3$): δ 7.41-7.49 (m), 7.24-7.27 (m), 7.13-7.18 (m), 6.57 (s), 6.58 (s), 4.21 (s), 4.19 (s), 1.66-1.76 (m), 1.39 (s), 0.91-1.00 (m), 0.73-0.79 (m), −0.21 (s), −0.27 (s), −0.31 (s).

Rac-dimethylsilylene-bis[4-(4-tert-butylphenyl)-2-cyclopropylinden-1-yl]dimethylzirconium (2)

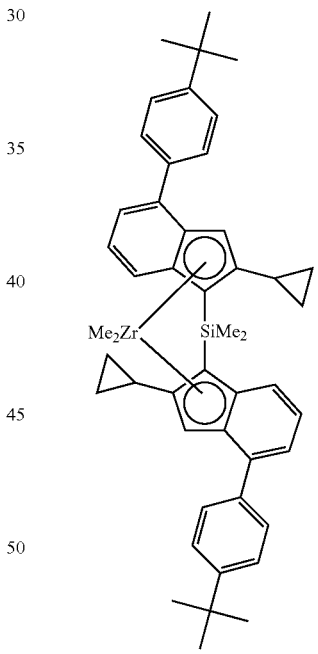

To a solution of 2.10 g (3.32 mmol) of bis[4-(4-tert-butylphenyl)-2-cyclopropyl-1H-inden-1-yl](dimethyl)silane in 70 ml of ether cooled to 0° C., 2.66 ml (6.64 mmol) of 2.5 M $^n$BuLi in hexanes was added. The resulting mixture was stirred for 12 h at room temperature, then cooled to −70° C., and 1.25 g (3.32 mmol) of ZrCl$_4$(THF)$_2$ was added. This mixture was stirred overnight at room temperature and then evaporated to dryness. The residue was dissolved in 60 ml of toluene, and the obtained suspension was refluxed for 3 h. Further on, 6.40 ml (19.9 mmol) of 3.1 M MeMgBr in ether was added, and the reaction mixture was stirred for 12 h at 75° C. in a glass pressure vessel. The obtained mixture was filtered through glass frit (G4), and the filtrate was evaporated to dryness. The residue was extracted with 3×100 ml of toluene. The combined toluene extract was evaporated to dryness. The residue was washed with 50 ml of toluene and then dried in vacuum. Yield 0.18 g (7%) of a ca. 92 to 8 mixture of rac- and meso-complexes as yellow crystalline solid. Calcd. for $C_{46}H_{50}Cl_2SiZr$: C, 76.64; H, 7.50. Found: C, 76.94; H, 7.72. $^1H$ NMR ($CD_2Cl_2$): δ 7.45-7.56 (m, 10H, 2,3,5,6-H in 4-$^tBuC_6H_4$ and 5-H in indenyl), 7.26-7.29 (m, 2H, 7-H in indenyl), 6.95-7.00 (m, 2H, 6-H in indenyl), 6.79 (s, 2H, 3-H in indenyl), 1.78 (m, 2H, 1-H in $^cPr$), 1.34 (s, 18H, $^tBu$), 1.23 (s, 6H, $SiMe_2$), 0.92 (m, 2H, 2/3-H in $^cPr$), 0.72 (m, 2H, 2/3-H in $^cPr$), 0.61 (m, 2H, 2/3-H in $^cPr$), 0.41 (m, 2H, 2/3-H in $^cPr$), −1.15 (s, 6H, $ZrMe_2$).

Example 3: Synthesis of rac-dimethylsilylene-bis[4-phenyl-2-cyclopropylinden-1-yl]zirconium dichloride (3)

7-Phenyl-1H-indene

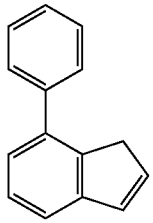 [SMILES: C1=Cc2cccc(-c3ccccc3)c2C1]

To a mixture of 51.0 g (320 mmol) of bromobenzene, 0.35 g (0.45 mmol) of "iPrNi", and 300 ml of THF, 290 ml (270 mmol) of 0.93 M (1-methoxy-2,3-dihydro-1H-inden-4-yl) magnesium bromide in THF was added by vigorous stirring for 3 minutes. After that, one more portion of 0.35 g (0.45 mmol) of "iPrNi" was added. The resulting mixture was refluxed for 1 h, then cooled to room temperature, and 300 ml of water was added. The obtained mixture was acidified with 10% HCl to pH~6. The organic layer was separated, washed by aqueous $NaHCO_3$ and water, then dried over $Na_2SO_4$, and evaporated to dryness. Crude 4-phenyl-1-methoxyindane was purified by flash chromatography on silica gel 60 (40-63 um; eluent: hexanes-dichloromethane=1:2, vol.). Further on, a mixture of this methoxyindane, 0.5 g of TsOH, and 500 ml of toluene was refluxed with a Dean-Stark head for 1 h. The resulting solution was cooled to room temperature, passed through a pad of silica gel 60 (40-63 um), and then evaporated to dryness. The residue was purified by flash chromatography on silica gel 60 (40-63 um; eluent: hexanes). Yield 44.0 g (86%) of yellow oil. Calcd. for $C_{15}H_{12}$: C, 93.71; H, 6.29. Found: C, 93.84; H, 6.41. $^1H$ NMR ($CDCl_3$): δ 7.38-7.63 (m, 7H, 5,6-H in indene and Ph), 7.30 (m, 1H, 4-H in indene), 7.01 (m, 1H, 3-H in indene), 6.64 (m, 1H, 2-H in indene), 3.54 (m, 2H, 1,1-H in indene).

2-Bromo-7-phenyl-1H-indene

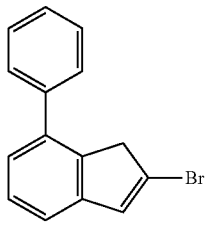 [SMILES: BrC1=Cc2cccc(-c3ccccc3)c2C1]

To a mixture of 45.1 g (234 mmol) of 7-phenyl-1H-indene, 9.00 ml (500 mmol) of water, 400 ml of DMSO, and 100 ml of THF cooled to 0° C., 41.0 g (234 mmol) of N-bromosuccinimide was added in small portions during 1 h. The obtained mixture was stirred for 12 h at room temperature and then diluted with 1500 ml of water. Crude product was extracted with 3×100 ml of dichloromethane. The combined organic extract was washed with 5×150 ml of water, dried over $Na_2SO_4$, and evaporated to dryness. A mixture of the residue, 0.8 g of TsOH, and 400 ml of toluene was refluxed with a Dean-Stark head for 7 h. The resulting solution was cooled to room temperature, passed through a pad of silica gel 60 (40-63 um), and then evaporated to dryness. The residue was purified by flash chromatography on silica gel 60 (40-63 um; eluent: hexanes). Yield 47.5 g (78%) of yellow oil crystallizes at room temperature. Calcd. for $C_{15}H_{11}Br$: C, 66.44; H, 4.09. Found: C, 66.56; H, 4.28. $^1H$ NMR ($CDCl_3$): δ 7.31-7.53 (m, 7H, 5,6-H in indene and Ph), 7.23 (m, 1H, 4-H in indenyl), 7.01 (s, 1H. 3-H in indenyl), 3.70 (s, 2H, 1,1-H in indenyl).

2-Cyclopropyl-4/7-phenyl-1H-indene

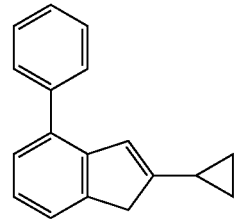 [SMILES: C1=C(C2CC2)Cc2cccc(-c3ccccc3)c21]

To a solution of 45.5 g (168 mmol) of 2-bromo-7-phenyl-1H-indene in 800 ml of THF, 1.31 g (1.70 mmol) of "iPrNi" was added. This mixture was stirred for 5 minutes at room temperature, and then 382 ml (252 mmol) of 0.66 M $^cPrMgBr$ in THF was added for 10 minutes. The obtained mixture was stirred for 36 h at 60° C., then cooled to room temperature and poured into 1000 ml of aqueous $NH_4Cl$. The organic layer was separated, and the aqueous layer was extracted with 3×200 ml of dichloromethane. The combined organic extract was washed by 3×100 ml of brine, dried over $Na_2SO_4$, and evaporated to dryness. The residue was purified by flash chromatography on silica gel 60 (40-63 um; eluent: hexanes). Yield 26.5 g (68%) of yellow oil of a mixture of two isomeric compounds. Calcd. for $C_{18}H_{16}$: C, 93.06; H, 6.94. Found: C, 93.30; H, 7.12. $^1H$ NMR ($CDCl_3$): δ 7.13-7.56 (m), 6.72 (s), 6.59 (s), 3.30 (s), 1.84 (m), 0.90 (m), 0.67 (m).

Bis(2-cyclopropyl-4-phenyl-1H-inden-1-yl)(dimethyl)silane

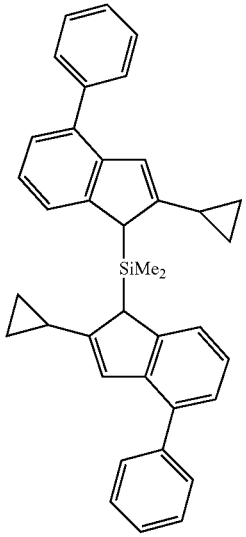

To a solution of 4.64 g (20.0 mmol) of 2-cyclopropyl-4/7-phenyl-1H-indene in 50 ml of ether cooled to 0° C., 8.00 ml (20.0 mmol) of 2.5 M "BuLi in hexanes was added. This mixture was stirred for 12 h at room temperature, then 10 ml of THF was added. To the obtained mixture cooled to −60° C., 0.179 g (2.00 mmol) of CuCN was added. This mixture was slowly warmed to −30° C., then cooled again to −60° C., and 1.22 ml (10.0 mmol) of dichlorodimethylsilane was added. The resulting mixture was stirred for 12 h at room temperature and then 40 ml of water was added. The organic layer was separated, the aqueous layer was extracted with 2×50 ml of ethyl acetate. The combined organic extract was dried over $Na_2SO_4$ and then evaporated to dryness. The residue was purified by flash chromatography on silica gel 60 (40-63 um; eluent: hexanes-dichloromethane=10:1, vol.). Yield 3.84 g (63%) of yellow oil of a ca. 1 to 1 mixture of rac- and meso-compounds. Calcd. for $C_{38}H_{36}Si$: C, 87.64; H, 6.97. Found: C, 87.61; H, 7.24. $^1H$ NMR ($CDCl_3$): δ 7.44-7.55 (m), 7.34-7.38 (m), 7.25-7.28 (m), 7.16-7.20 (m), 6.54 (s), 4.22 (s), 4.21 (s), 1.65-1.77 (m), 0.94-1.01 (m), 0.73-0.79 (m), −0.17 (s), −0.23 (s), −0.28 (s).

Rac-dimethylsilylene-bis[4-phenyl-2-cyclopropylinden-1-yl]zirconium dichloride (3)

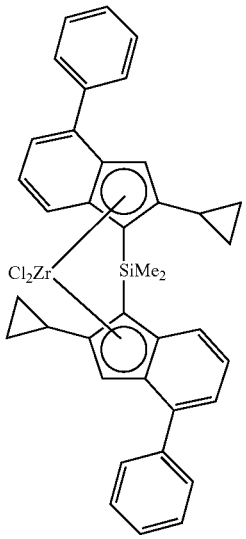

To a solution of 2.08 g (4.00 mmol) of bis(2-cyclopropyl-4-phenyl-1H-inden-1-yl)(dimethyl)silane in 50 ml of ether cooled to 0° C., 3.20 ml (8.00 mmol) of 2.5 M "BuLi in hexanes was added. The resulting mixture was stirred for 12 h at room temperature, then cooled to −70° C., and 1.51 g (4.00 mmol) of $ZrCl_4(THF)_2$ was added. The obtained mixture was stirred overnight at room temperature and then evaporated to dryness. The residue was dissolved in 50 ml of toluene, and the formed solution was stirred for 6 h at 60° C. and then 12 h at room temperature. Further on, the reaction mixture was heated to 80° C., and this hot mixture was filtered through a Celite pad. The filtrate was diluted by toluene to ca. 90 ml. Crystals precipitated at room temperature were collected and then re-crystallized again from 50 ml of toluene. This procedure gave 0.35 g (13%) of pure rac-complex as orange crystals. Calcd. for $C_{38}H_{34}Cl_2SiZr$: C, 67.03; H, 5.03. Found: C, 66.94; H, 5.12. $^1H$ NMR ($CD_2Cl_2$): δ 7.69 (m, 2H, 5-H in indenyl), 7.60-7.62 (m, 4H, 2,6-H in Ph), 7.42-7.45 (m, 4H, 3,5-H in Ph), 7.37 (m, 2H, 4-H in Ph), 7.35 (m, 2H, 7-H in indenyl), 7.07 (dd, J=8.8 Hz, J=6.9 Hz, 2H, 6,6'-H in indenyl), 6.61 (s, 2H, 3,3'-H in indenyl), 2.00 (m, 2H, 1,1-H in cyclopropyl), 1.44 (s, 6H, $SiMe_2$), 1.05 (m, 2H, 2/3-H in $^cPr$), 0.90 (m, 2H, 2/3-H in $^cPr$), 0.75 (m, 2H, 2/3-H in $^cPr$), 0.44 (m, 2H, 2/3-H in $^cPr$).

Example 4: Synthesis of dimethylsilylene-bis[4-(1-naphthyl)-2-cyclopropylinden-1-yl]zirconium dichloride (4)

1-(1H-Inden-7-yl)naphthalene

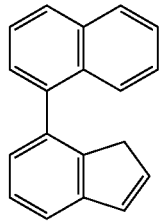 [SMILES: C1=Cc2cccc(-c3cccc4ccccc34)c2C1]

To a mixture of 50.0 g (240 mmol) of 1-bromonaphthalene, 0.37 g (0.47 mmol) of "iPrNi", and 250 ml of THF, 215 ml (200 mmol) of 0.93 M (1-methoxy-2,3-dihydro-1H-inden-4-yl)magnesium bromide in THF was added by vigorous stirring for 3 minutes. After that one more portion of 0.37 g (0.45 mmol) of "iPrNi" was added. The resulting mixture was refluxed for 1 h, then cooled to room temperature, and 300 ml of water was added. The obtained mixture was acidified with 10% HCl to pH~6. The organic layer was separated, washed by aqueous $NaHCO_3$ and water, then dried over $Na_2SO_4$, and evaporated to dryness. Crude 4-phenyl-1-methoxyindane was purified by flash chromatography on silica gel 60 (40-63 um; eluent: hexanes-dichloromethane=1:2, vol.). Further on, a mixture of this methoxyindane, 0.1 g of TsOH, and 500 ml of toluene was refluxed with a Dean-Stark head for 1 h. The resulting solution was cooled to room temperature, passed through a pad of silica gel 60 (40-63 um), and then evaporated to dryness. The residue was purified by flash chromatography on silica gel 60 (40-63 um; eluent: hexanes). Yield 16.9 g (36%) of yellow oil. Calcd. for $C_{19}H_{14}$: C, 94.18; H, 5.82. Found: C, 93.99; H, 5.95. $^1H$ NMR ($CDCl_3$): δ 7.94 (m, 1H, 4-H in naphthyl), 7.91 (m, 1H, 8-H in naphthyl), 7.63 (m, 1H, 6-H in indene), 7.56 (m, 1H, 7-H in naphthyl), 7.51 (m, 1H, 6-H in naphthyl), 7.50 (m, 1H, 5-H in naphthyl), 7.49 (m, 1H, 2-H in naphthyl), 7.43 (m, 1H, 3-H in naphthyl), 7.38 (m, 1H, 5-H in indene), 7.24 (m, 1H, 4-H in indene), 6.99 (m, 1H, 3-H in indene), 6.53 (m, 1H, 2-H in indene), 3.15 (m, 2H, 1,1-H in indene).

1-(2-Bromo-1H-inden-7-yl)naphthalene

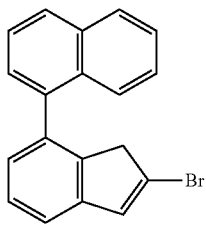 [SMILES: BrC1=Cc2cccc(-c3cccc4ccccc34)c2C1]

To a mixture of 16.9 g (70.0 mmol) of 1-(1H-inden-7-yl)naphthalene, 2.50 ml (140 mmol) of water, 150 ml of DMSO, and 75 ml of THF cooled to 0° C., 13.1 g (73.0 mmol) of N-bromosuccinimide was added in small portions for 1 h. This mixture was stirred for 12 h at room temperature and then 800 ml of water was added. The formed substituted bromohydrin was extracted with 3×100 ml of dichloromethane. The combined organic extract was washed with 5×100 ml of water, dried over $Na_2SO_4$, and evaporated to dryness. A mixture of the residue, 0.25 g of p-toluenesulfonic acid, and 150 ml of toluene was refluxed with a Dean-Stark head for 5 h. The resulting solution was cooled, passed through a pad of silica gel 60 (40-63 um), and evaporated to dryness. The residue was washed by 50 ml of hexanes and then dried in vacuum. Yield 15.2 g (68%) of beige powder. Calcd. for $C_{19}H_{13}Br$: C, 71.04; H, 4.08. Found: C, 71.36; H, 4.28. $^1H$ NMR ($CDCl_3$): δ 7.92 (m, 1H, 4-H in naphthyl), 7.89 (m, 1H, 8-H in naphthyl), 7.35-7.57 (m, 7H, 4,6-H in indene and 2,3,5,6,7-H in naphthyl), 7.19 (m, 1H, 5-H in indene), 7.01 (s, 1H, 3-H in indenyl), 3.33 (m, 2H, 1,1-H in indenyl).

1-(2-Cyclopropyl-1H-inden-4/7-yl)naphthalene

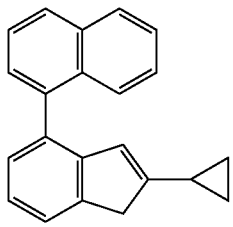 [SMILES: C1=C(C2CC2)Cc2cccc(-c3cccc4ccccc34)c21]

To a solution of 15.0 g (46.7 mmol) of 1-(2-bromo-1H-inden-7-yl)naphthalene in 300 ml of THF, 0.36 g (0.47 mmol) of "iPrNi" was added. This mixture was stirred for 5 minutes at room temperature, and then 106 ml (70.0 mmol) of 0.66 M $^cPrMgBr$ in THF was added dropwise for 10 minutes at this temperature. The obtained mixture was stirred for 12 h at 60° C., then cooled to room temperature, and poured into 200 ml of aqueous $NH_4Cl$. The organic layer was separated, and the aqueous layer was extracted with 3×100 ml of dichloromethane. The combined organic extract was washed with 50 ml of brine, dried over $Na_2SO_4$, and evaporated to dryness. Thus obtained crude product was purified by flash chromatography on silica gel 60 (40-63 um; eluent: hexanes). Yield 9.75 g (74%) of yellow oil of a mixture of two isomeric indenes. Calcd. for $C_{22}H_{18}$: C, 93.57; H, 6.43. Found: C, 93.44; H, 6.21. $^1H$ NMR ($CDCl_3$): δ 7.95 (m), 7.92 (m), 7.77 (m), 7.67 (m), 7.35-7.60 (m), 7.31 (m), 7.25 (m), 7.14 (m), 6.64 (s), 6.19 (s), 3.35 (m), 2.97 (m), 1.77 (m), 1.33 (m), 0.95 (m), 0.85 (m), 0.61 (m), 0.56 (m).

Bis[2-cyclopropyl-4-(1-naphthyl)-1H-inden-1-yl](dimethyl)silane

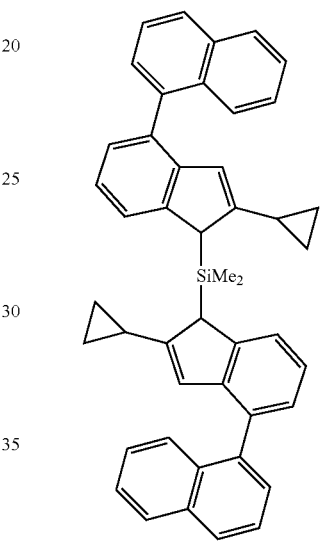

To a solution of 6.00 g (21.2 mmol) of 1-(2-cyclopropyl-1H-inden-4-yl)naphthalene in 50 ml of ether cooled to 0° C., 8.50 ml (21.2 mmol) of 2.5 M $^nBuLi$ in hexanes was added. This mixture was stirred for 12 h at room temperature, then 10 ml of THF was added. The reaction mixture was cooled to −60° C., and 0.190 g (2.12 mmol) of CuCN was added. Further on, this mixture was warmed to −30° C., stirred at this temperature for 30 minutes, then cooled to −60° C., and 1.29 ml (10.6 mmol) of dichlorodimethylsilane was added at this temperature. The obtained mixture was stirred for 24 h at room temperature, then 40 ml of water was added. The organic layer was separated, the aqueous layer was extracted with 2×50 ml of ethyl acetate. The combined organic extract was dried over $Na_2SO_4$ and then evaporated to dryness. Crude product was purified by flash chromatography on silica gel 60 (40-63 um; eluent: hexanes-ethyl acetate=20:1, vol.). Yield 4.20 g (64%) of yellow oil as a ca. 2 to 1 mixture of meso- and rac-compounds. Calcd. for $C_{46}H_{40}Si$: C, 88.98; H, 6.49. Found: C, 89.24; H, 6.71. $^1H$ NMR ($CDCl_3$): δ 7.89-7.95 (m), 7.62-7.67 (m), 7.35-7.60 (m), 7.24-7.29 (m), 6.04 (m), 5.95 (m), 4.33 (m), 4.29 (m), 1.60-1.79 (m), 0.83-0.97 (m), 0.54-0.67 (m), −0.08 (s), −0.13 (s), −0.16 (s), −0.21 (s).

Dimethylsilylene-bis[4-(1-naphthyl)-2-cyclopropyl-inden-1-yl]zirconium dichloride (4)

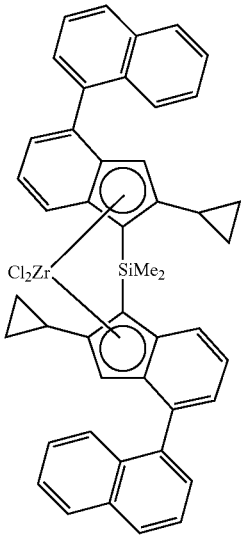

To a solution of 2.48 g (4.00 mmol) of bis[2-cyclopropyl-4-(1-naphthyl)-1H-inden-1-yl](dimethyl)silane in 50 ml of ether cooled to 0° C., 3.20 ml (8.00 mmol) of 2.5 M ″BuLi in hexanes was added. The resulting mixture was stirred for 12 h at room temperature, then cooled to −70° C., and 1.51 g (4.00 mmol) of ZrCl$_4$(THF)$_2$ was added. The reaction mixture was stirred overnight at room temperature and then evaporated to dryness. The residue was extracted with 100 ml of hot toluene, and this hot mixture was filtered through glass frit (G4). Crystals precipitated from this filtrate at room temperature were collected and then re-crystallized from 70 ml of toluene. This procedure gave 2.00 g (64%) of a ca. 4 to 3 mixture of rac- and meso-complexes as red crystalline powder. Calcd. for C$_{46}$H$_{38}$Cl$_2$SiZr: C, 70.74; H, 4.90. Found: C, 70.91; H, 4.80. $^1$H NMR (CD$_2$Cl$_2$): δ 7.89-7.92 (m), 7.83 (m), 7.74-7.79 (m), 7.58 (m), 7.56 (m), 7.43-7.51 (m), 7.36 (m), 7.30-7.33 (m), 7.09 (dd, J=8.6 Hz, J=6.9 Hz), 7.00 (dd, J=8.8 Hz, J=6.9 Hz), 6.11 (s), 6.03 (s), 2.08 (m), 2.02 (m), 1.60 (s), 1.47 (s), 1.38 (s), 1.00-1.07 (m), 0.66-0.83 (m), 0.32-0.39 (m).

Example 5: Synthesis of dimethylsilylene-bis[4-chloro-2-cyclopropylinden-1-yl]zirconium dichloride (5)

4-Chloroindan-1-one

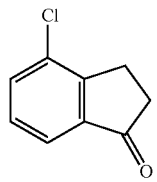 [SMILES: O=C1CCc2c(Cl)cccc21]

To the solution of sodium ethoxide obtained from 36.8 g (1.60 mol) of sodium lump and 1600 ml of anhydrous ethanol, 512 g (3.20 mol) of diethyl malonate was added. This mixture was stirred for 10 minutes, and then 258 g (1.60 mol) of 2-chlorobenzyl chloride was added for 20 minutes with gentle reflux. The resulting mixture was refluxed for 3 h, then cooled to room temperature and filtered through glass frit (G3). The filtrate was evaporated to dryness. An excess of diethyl malonate was distilled off in vacuum. The residue was dissolved in 1000 ml of 96% ethanol, and a solution of 358 g (6.4 mol) of KOH in 1000 ml of water was added. The resulting mixture was refluxed for 5 h, then ethanol was distilled off at atmospheric pressure. The residue was acidified with 12 M HCl to pH~5. The precipitate formed was filtered off, washed with water, and then dried on air. Decarboxilation of this solid at 180° C. gave the respective carbonic acid. A mixture of this acid and 666 g (5.60 mol) of thionyl chloride was stirred overnight at room temperature. An excess of thionyl chloride was distilled off at atmospheric pressure. Vacuum distillation of the residue afforded yellow oil, b.p. 98-101° C./1 mm Hg. To a suspension of 136 g (1.02 mol) of AlCl$_3$ in 600 ml of dichloromethane, a solution of 166 g (810 mmol) of the above-obtained 3-(2-chlorophenyl)propanoyl chloride in 200 ml of dichloromethane was added for 30 minutes at 0° C. This mixture was stirred for 18 h at room temperature and then poured on 2000 cm$^3$ of ice. Crude product was extracted with 3×300 ml of dichloromethane. The combined organic extract was washed with 200 ml of 1M HCl, 2×200 ml of water, dried over Na$_2$SO$_4$, and evaporated to dryness. Yield 130 g (50%) of beige solid. Calcd. for C$_9$H$_7$ClO: C, 64.88; H, 4.23. Found: C, 65.04; H, 4.56. $^1$H NMR (CDCl$_3$): δ 7.63 (m, 1H, 7-H), 7.55 (m, 1H, 5-H), 7.32 (m, 1H, 6-H), 3.10 (m, 2H, 3,3-H), 2.71 (m, 2H, 2,2-H).

7-Chloro-1H-indene

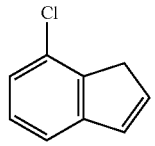

To a solution of 134 g (805 mmol) of 4-chloroindan-1-one in a mixture of 650 ml of THF and 320 ml of methanol, 45.7 g (1.20 mol) of NaBH$_4$ was added by small portions for 15 minutes at 0° C. This mixture was stirred overnight at room temperature and then evaporated to dryness. Further on, 1000 ml of hot water was added, and the formed mixture was cooled to room temperature. Crude 4-chloro-1-indanol was extracted with 3×200 ml of dichloromethane. The combined organic extract was dried over Na$_2$SO$_4$ and then evaporated to dryness. The residue was dissolved in 800 ml of toluene, and 0.5 g of TsOH was added at 80° C. This mixture was refluxed with Dean-Stark head for 2.5 h (HPLC control). The resulting mixture was cooled to room temperature, washed with aqueous K$_2$CO$_3$, water, then dried over Na$_2$SO$_4$, and finally passed through a pad of silica gel 60 (40-63 um). The elute was evaporated to dryness. Vacuum distillation of the residue gave 103 g (85%) of yellow oil which crystallizes at room temperature, b.p. 77° C./5 mm Hg. Calcd. for C$_9$H$_7$Cl: C, 71.77; H, 4.68. Found: C, 71.60; H, 4.70. $^1$H NMR (CDCl$_3$): δ 7.31 (m), 7.25 (m), 7.19 (m), 6.89 (m), 6.63 (m), 3.45 (s).

2-Bromo-7-chloro-1H-indene

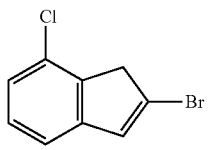 [SMILES: Clc1cccc2c1CC(Br)=C2]

To a mixture of 21.6 g (143 mmol) of 7-chloro-1H-indene, 5.00 ml (280 mmol) of water, and 200 ml of DMSO cooled to 0° C., 26.7 g (150 mmol) of N-bromosuccinimide was added in small portions for 1 h. This mixture was stirred for 12 h at room temperature, and then 400 ml of water was added. The formed substituted bromohydrine was extracted with 3×100 ml of dichloromethane. The combined organic extract was washed with 5×100 ml of water, dried over $Na_2SO_4$, and evaporated to dryness. A mixture of the residue, 1.20 g of TsOH, and 500 ml of toluene was refluxed with a Dean-Stark head for 12 h. The resulting solution was cooled, passed through a pad of silica gel 60 (40-63 um), and evaporated to dryness. Vacuum distillation of the residue gave 26.5 g (76%) of yellow oil which crystallizes at room temperature, b.p. 100-108° C./1 mm Hg. Calcd. for $C_9H_6BrCl$: C, 47.10; H, 2.64. Found: C, 46.96; H, 2.58. $^1H$ NMR ($CDCl_3$): δ 7.16-7.22 (m, 2H, 4,6-H), 7.13 (dd, J=6.3 Hz, J=2.8 Hz, 1H, 5-H), 6.91 (m, 1H, 3-H), 3.62 (d, J=1.5 Hz, 2H, 1,1'-H).

7-Chloro-2-cyclopropyl-1H-indene

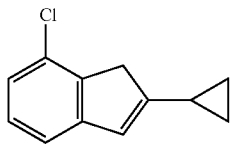 [SMILES: Clc1cccc2c1CC(C1CC1)=C2]

To a solution of 1.00 g (4.40 mmol) of 2-bromo-7-chloro-1H-indene in 15 ml of THF, 0.034 g (0.040 mmol) of "iPrNi" was added. This mixture was stirred for 5 minutes at room temperature, and then 6.70 ml (4.40 mmol) of 0.66 M $^cPrMgBr$ in THF was added in 10 minutes. The obtained mixture was stirred for 12 h at 60° C., then cooled to room temperature, and poured into 20 ml of aqueous $NH_4Cl$. The organic layer was separated, the aqueous layer was extracted with 3×10 ml of dichloromethane. The combined organic extract was washed with 20 ml of brine, dried over $Na_2SO_4$, and evaporated to dryness. Crude product was purified by flash chromatography on silica gel 60 (40-63 um; eluent: hexanes). Yield 0.60 g (72%) of colorless oil. Calcd. for $C_{12}H_{11}Cl$: C, 75.59; H, 5.81. Found: C, 75.84; H, 6.06. $^1H$ NMR ($CDCl_3$): δ 7.15 (t, J=7.6 Hz, 1H, 5-H in indenyl), 7.10 (dd, J=7.6 Hz, J=1.0 Hz, 1H, 4-H in indenyl), 7.04 (dd, J=7.6 Hz, J=1.0 Hz, 1H, 6-H in indenyl), 6.49 (s, 1H, 3-H in indenyl), 3.20 (s, 2H, 1,1-H in indenyl), 1.84 (m, 1H, 1-H in cyclopropyl), 0.92 (m, 2H, 2,3-H in cyclopropyl), 0.68 (m, 2H, 2',3'-H in cyclopropyl).

Bis(4-chloro-2-cyclopropyl-1H-inden-1-yl)(dimethyl)silane

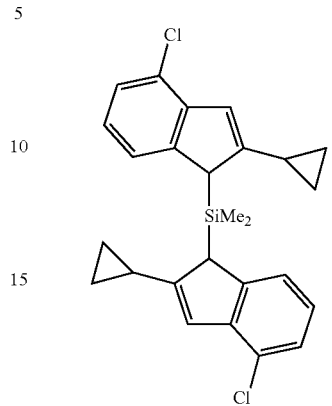

To a solution of 5.00 g (26.2 mmol) of 4-chloro-2-cyclopropyl-1H-indene in 60 ml of ether cooled to 0° C., 10.5 ml (26.2 mmol) of 2.5 M "BuLi in hexanes was added. This mixture was stirred for 12 h at room temperature, and then 10 ml of THF was added. The obtained mixture was cooled to −60° C., 0.236 g (2.60 mmol) of CuCN was added. Further on, this mixture was warmed to −30° C., stirred for 30 minutes at this temperature, then cooled to −60° C. and 1.58 ml (13.1 mmol) of dichlorodimethylsilane was added. The resulting mixture was stirred for 24 h at room temperature, and then 40 ml of water was added. The organic layer was separated, the aqueous layer was extracted with 2×50 ml of ethyl acetate. The combined organic extract was dried over $Na_2SO_4$ and then evaporated to dryness. Crude product was purified by flash chromatography on silica gel 60 (40-63 um; eluent: hexanes-ethyl acetate=20:1, vol.). Yield 3.50 g (61%) of yellow oil of a ca. 1 to 1 mixture of rac- and meso-compounds. Calcd. for $C_{26}H_{26}Cl_2Si$: C, 71.38; H, 5.99. Found: C, 71.44; H, 6.25. $^1H$ NMR ($CDCl_3$): δ 7.33 (m), 7.29 (m), 7.20 (m), 7.18 (m), 7.03 (m), 7.01 (m), 6.48 (s), 4.15 (m), 1.61-1.71 (m), 0.98-1.07 (m), 0.77-0.90 (m), −0.23 (s), −0.30 (s), −0.39 (s).

Dimethylsilylene-bis[4-chloro-2-cyclopropylinden-1-yl]zirconium dichloride (5)

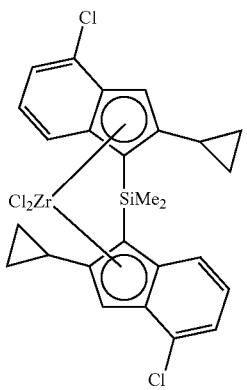

To a solution of 1.81 g (4.14 mmol) of bis(4-chloro-2-cyclopropyl-1H-inden-1-yl)(dimethyl)silane in 60 ml of ether cooled to 0° C., 3.31 ml (8.28 mmol) of 2.5 M "BuLi in hexanes was added. This mixture was stirred for 12 h at room temperature, cooled to −70° C., and 1.56 g (4.14 mmol) of ZrCl₄(THF)₂ was added. The obtained mixture was stirred overnight at room temperature and then evaporated to dryness. The residue was dissolved in 50 ml of toluene, and the formed mixture was stirred for 5 h at 70° C. and then for 12 h at room temperature. Further on, this mixture was filtered through glass frit (G4). Crystals precipitated from the filtrate at −30° C. were collected and dried in vacuum. Yield 0.82 g (33%) of a. ca 1 to 1 mixture of rac- and meso-complexes as red crystalline solid. Calcd. for C₂₆H₂₄Cl₄SiZr: C, 52.26; H, 4.05. Found: C, 52.12; H, 4.09. Meso-complex. ¹H NMR (CD₂Cl₂): δ 7.55 (m, 2H, 7-H in indenyl), 7.12 (m, 2H, 5-H in indenyl), 6.71 (dd, J=8.7 Hz, J=7.2 Hz, 2H, 6-H in indenyl), 6.56 (s, 2H, 3-H in indenyl), 2.12 (m, 2H, 1-H in cyclopropyl), 1.46 (s, 3H, SiMeMe'), 1.40 (m, 2H, 2-H, 2/3-H in ᶜPr), 1.36 (s, 3H, SiMeMe'), 1.16 (m, 2H, 2/3-H in ᶜPr), 1.00 (m, 2H, 2/3-H in ᶜPr), 0.59 (m, 2H, 2/3-H in ᶜPr). Rac-complex. ¹H NMR (CD₂Cl₂): δ 7.59 (m, 2H, 7-H in indenyl), 7.35 (m, 2H, 5-H in indenyl), 6.92 (dd, J=8.6 Hz, J=7.6 Hz, 2H, 6-H in indenyl), 6.59 (s, 2H, 3-H in indenyl), 1.91 (m, 2H, 1-H in ᶜPr), 1.38 (s, 6H, SiMe₂), 1.09 (m, 2H, 2/3-H in ᶜPr), 0.97 (m, 2H, 2/3-H in ᶜPr), 0.77 (m, 2H, 2/3-H in ᶜPr), 0.52 (m, 2H, 2/3-H in ᶜPr).

Example 6: Synthesis of dimethylsilylene-bis[4-(1-naphthyl)-2-cyclopropylinden-1-yl]zirconium dichloride (6)

9-(2-Cyclopropyl-1H-inden-4/7-yl)-9H-carbazole

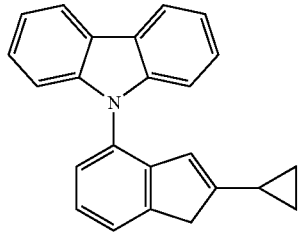 [SMILES: C1=C(C2CC2)Cc2cccc(-n3c4ccccc4c4ccccc43)c21]

A mixture of 5.00 g (26.0 mmol) of 4/7-chloro-2-cyclopropyl-1H-indene, 4.38 g (26.0 mmol) of 9H-carbazole, 6.30 g (79.0 mmol) of lithium tert-butoxide, 0.30 g (0.52 mmol) of Pd(dba)₂, 0.21 g (1.04 mmol) of ᵗBu₃P, and 50 ml of toluene was stirred in a glass pressure vessel for 12 h at 110° C. The obtained mixture was poured into 100 ml of cold water. The organic layer was separated, the aqueous layer was extracted with 2×50 ml of dichloromethane. The combined organic extract was dried over Na₂SO₄ and then evaporated to dryness. Crude product was purified by flash chromatography on silica gel 60 (40-63 um; eluent: hexanes). Yield 7.50 g (59%) of a ca. 1 to 1 mixture of two isomeric indenes. Calcd. for C₂₄H₁₉N: C, 89.68; H, 5.96; N, 4.36. Found: C, 89.84; H, 6.32; N, 4.59. ¹H NMR (CDCl₃): δ 8.17 (m), 7.18-7.47 (m), 7.13 (m), 6.60 (s), 6.05 (s), 3.35 (s), 2.90 (s), 1.73 (m), 0.82 (m), 0.58 (m), 0.52 (m).

9-{2-Cyclopropyl-1-[dimethyl(2-methyl-4-phenyl-1H-inden-1-yl)silyl]-1H-inden-4-yl}-9H-carbazole

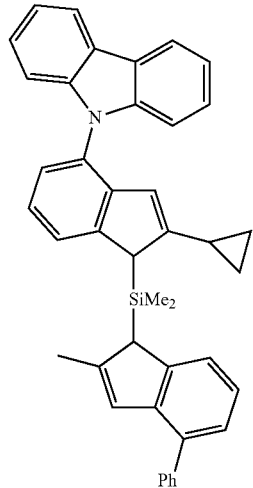

To a solution of 3.50 g (10.9 mmol) of 9-(2-cyclopropyl-1H-inden-4/7-yl)-9H-carbazole in 50 ml of ether cooled to 0° C., 4.36 ml (10.9 mmol) of 2.5 M "BuLi in hexanes was added. This mixture was stirred for 12 h at room temperature, and then 10 ml of THF was added. The obtained mixture was cooled to −50° C., 0.19 g (2.12 mmol) of CuCN was added. Further on, this mixture was warmed to −30° C., stirred for 30 minutes at this temperature, then cooled to −60° C., and 3.26 ml (10.9 mmol) of chloro(2-methyl-4-phenyl-1H-inden-1-yl)dimethylsilane was added. The resulting mixture was stirred for 12 h at room temperature, and then 40 ml of water was added. The organic layer was separated, the aqueous layer was extracted with 2×50 ml of ethyl acetate. The combined organic extract was dried over Na₂SO₄ and then evaporated to dryness. Thus obtained crude product was purified by flash chromatography on silica gel 60 (40-63 um; eluent: hexanes-dichloromethane=10:1 and then 4:1, vol.). Yield 4.45 g (70%) of yellow oil of a ca. 1 to 1 mixture of two isomeric compounds. Calcd. for C₄₂H₃₇NSi: C, 86.40; H, 6.39; N, 2.40. Found: C, 86.72; H, 6.47; N, 2.25. ¹H NMR (CDCl₃): δ 8.18 (m), 7.55-7.60 (m), 7.45-7.50 (m), 7.21-7.41 (m), 7.10 (m), 6.86 (s), 5.86 (s), 5.29 (s), 4.18 (s), 4.16 (s), 4.01 (m), 2.33 (s), 2.29 (s), 1.65 (m), 1.56 (m), 0.85-0.90 (m), 0.52-0.59 (m), −0.14 (s), −0.16 (s), −0.18 (s), −0.19 (s).

Dimethylsilylene-bis[4-(1-naphthyl)-2-cyclopropyl-inden-1-yl]zirconium dichloride (6)

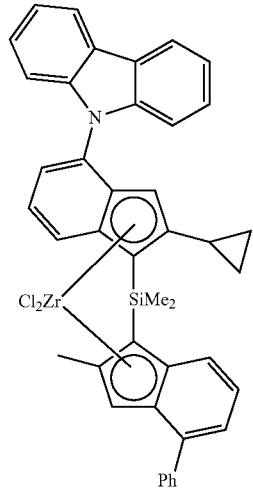

To a solution of 2.04 g (3.50 mmol) of (9-{2-cyclopropyl-1-[dimethyl(2-methyl-4-phenyl-1H-inden-1-yl)silyl]-1H-inden-4-yl}-9H-carbazole in 80 ml of ether cooled to 0° C., 2.80 ml (7.00 mmol) of 2.5 M ⁿBuLi in hexanes was added. The resulting mixture was stirred for 12 h at room temperature, cooled to −70° C., and 1.32 g (3.50 mmol) of ZrCl$_4$(THF)$_2$ was added. The obtained mixture was stirred overnight at room temperature and then evaporated to dryness. The residue was poured into a mixture of 50 ml of hexane and 10 ml of toluene, and the obtained suspension was filtered through glass frit (G4). The filtrate was evaporated to dryness, the residue was washed by a 40 ml of a mixture of hexane and DME (3:1, vol.) and then re-crystallized from 30 ml of toluene. Crystals precipitated at −30° C. were collected and dried in vacuum. Yield 0.18 g (7%) of pure anti-complex as yellow crystalline solid. Calcd. for C$_{42}$H$_{35}$Cl$_2$NSiZr: C, 67.81; H, 4.74; N, 1.88. Found: C, 68.00; H, 4.82; N, 1.60. $^1$H NMR (CD$_2$Cl$_2$): δ 8.12 (m, 1H, 5-H in indenyl bearing Ph), 8.09 (m, 1H, 5-H in indenyl bearing carbazolyl), 7.90 (m, 1H, 7-H in indenyl bearing carbazolyl), 7.82 (m, 2H, 4,5-H in carbazolyl), 7.56-7.59 (m, 2H, 2,6-H in Ph), 7.43 (m, 1H, 6-H in indenyl bearing Ph), 7.41 (m, 2H, 1,8-H in carbazolyl), 7.36 (m, 1H, 7-H in indenyl bearing Ph), 7.31 (m, 1H, 4-H in Ph), 7.20-7.27 (m, 4H, 3,6-H in carbazolyl and 3,5-H in Ph), 7.01 (ddd, J=8.6 Hz, J=7.1 Hz, J=3.3 Hz, 2H, 2,7-H in carbazolyl), 6.86 (s, 1H, 3-H in indenyl bearing Ph), 6.68 (m, 1H, 6-H in indenyl bearing carbazolyl), 6.11 (s, 1H, 3-H in indenyl bearing carbazolyl), 2.45 (s, 3H, 2-Me in indenyl), 2.10 (m, 1H, 1-H in $^c$Pr), 1.57 (s, 3H, SiMeMe'), 1.35 (s, 3H, SiMeMe'), 1.16-1.27 (m, 2H, 2/3-cPr), 0.95 (m, 1H, 2/3-cPr), 0.65 (m, 1H, 2/3-cPr).

Example 7: Synthesis of Dimethylsilylene(4-(4-tert-butylphenyl)-2-cyclopropylinden-1-yl)(4-phenyl-2-methylinden-1-yl)zirconium dichloride (7)

[4-(4-tert-Butylphenyl)-2-cyclopropyl-1H-inden-1-yl]-(2-methyl-4-phenyl-1H-inden-1-yl)dimethylsilane

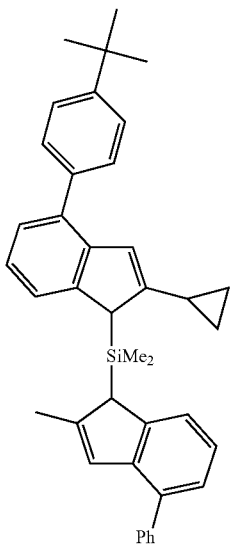

To a solution of 2.88 g (10.0 mmol) of 4-(4-tert-butylphenyl)-2-cyclopropyl-1H-indene in 80 ml of ether cooled to 0° C., 4.00 ml (10.0 mmol) of 2.5 M ⁿBuLi in hexanes was added. This mixture was stirred for 12 h at room temperature, and then 20 ml of THF was added. The obtained mixture was cooled to −50° C., and 0.09 g (1.00 mmol) of CuCN was added. Further on, this mixture was warmed to −30° C., stirred for 30 minutes at this temperature, then cooled to −60° C., and 2.99 g (10.0 mmol) of chloro(2-methyl-4-phenyl-1H-inden-1-yl)dimethylsilane was added. The resulting mixture was stirred for 12 h at room temperature, and then 100 ml of water was added. The organic layer was separated, the aqueous layer was extracted with 2×50 ml of ethyl acetate. The combined organic extract was dried over Na$_2$SO$_4$ and then evaporated to dryness. Crude product was purified by flash chromatography on silica gel 60 (40-63 um; eluent: hexanes-dichloromethane=10:1 and then 4:1, vol.). Yield 2.44 g (44%) of yellow oil of a mixture of two isomeric compounds. Calcd. for C$_{40}$H$_{42}$Si: C, 87.22; H, 7.69. Found: C, 87.46; H, 7.95. $^1$H NMR (CDCl$_3$): δ 7.54-7.58 (m), 7.44-7.52 (m), 7.33-7.39 (m), 7.24-7.31 (m), 7.14-7.22 (m), 6.83 (s), 6.59 (s), 4.07-4.06 (m), 3.98 (m), 2.27 (s), 2.25 (s), 1.72 (m), 1.62 (m), 1.41 (s), 1.40 (s), 0.92-0.99 (m), 0.73-0.80 (m), −0.18 (s), −0.19 (s), −0.22 (s), −0.23 (s).

Dimethylsilylene(4-(4-tert-butylphenyl)-2-cyclopropylinden-1-yl)(4-phenyl-2-methylinden-1-yl)zirconium dichloride (7)

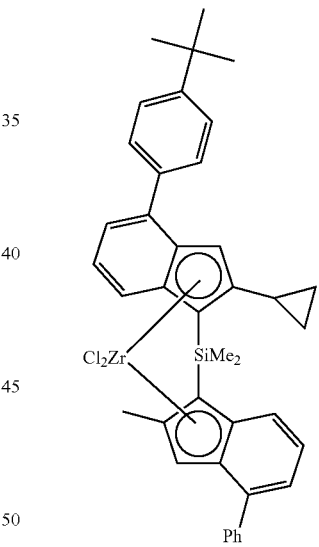

To a solution of 2.20 g (4.00 mmol) of [4-(4-tert-butylphenyl)-2-cyclopropyl-1H-inden-1-yl](2-methyl-4-phenyl-1H-inden-1-yl)dimethylsilane in 70 ml of ether cooled to 0° C., 3.20 ml (8.00 mmol) of 2.5 M ⁿBuLi in hexanes was added. This mixture was stirred for 12 h at room temperature, then cooled to −70° C., and 1.51 g (4.00 mmol) of ZrCl$_4$(THF)$_2$ was added. The obtained mixture was stirred overnight at room temperature and then evaporated to dryness. The residue was poured into 50 ml of hot toluene, and the formed hot suspension was filtered through a Celite pad. The filtrate was concentrated in vacuum to ca. 7 ml. Crystals precipitated from this solution at −30° C. were collected and dried in vacuum. This procedure gave 0.34 g (12%) of a ca. 2 to 9 mixture of anti- and syn-complexes as orange crystals (7a). The filtrate was diluted with 10 ml of hexane resulting in formation of some precipitate which was collected and dried in vacuum. This procedure gave 0.26 g (9%) of yellow powder of a ca. 1 to 3 mixture of anti- and syn-complexes (7b). Calcd. for $C_{40}H_{40}Cl_2SiZr$: C, 67.57; H, 5.67. Found: C, 67.62; H, 5.82. $^1$H NMR (CD$_2$Cl$_2$): δ 7.63-7.71 (m), 7.53-7.59 (m), 7.41-7.49 (m), 7.33-7.39 (m), 7.07-7.26 (m), 6.85-6.92 (m), 6.61 (s), 6.52 (s), 2.48 (m), 2.26 (m), 2.11 (m), 2.03 (m), 1.52 (s), 1.41 (s), 1.38 (s), 1.36 (m), 1.34 (s), 1.33 (s), 1.32 (s), 1.15 (m), 1.06 (m), 1.00 (m), 0.89 (m), 0.76 (m), 0.52 (m), 0.44 (m).

Example 8: Synthesis of rac-dimethylsilylene-bis[2-cyclopropyl-4,7-dimethylinden-1-yl]hafnium dichloride (8)

2-Cyclopropyl-4,7-dimethyl-1H-indene

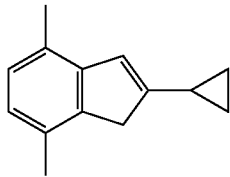

To a solution of 15.0 g (67.3 mmol) of 2-bromo-4,7-dimethyl-1H-indene in 230 ml of THF, 0.53 g (0.67 mmol) of "iPrNi" was added. This mixture was stirred for 5 minutes at room temperature, and then 130 ml (101 mmol) of 0.66 M $^c$PrMgBr in THF was added for 10 minutes. The obtained mixture was stirred for 12 h at 60° C., then cooled to room temperature and poured into 200 ml of aqueous NH$_4$Cl. The organic layer was separated, and the aqueous layer was extracted with 3×20 ml of ethyl acetate. The combined organic extract was washed with 100 ml of brine, dried over Na$_2$SO$_4$, and evaporated to dryness. Crude product was purified by flash chromatography on silica gel 60 (40-63 um; eluent: hexanes). Yield 3.01 g (25%) of white crystalline powder. Calcd. for $C_{14}H_{16}$: C, 91.25; H, 8.75. Found: C, 91.07; H, 8.58. $^1$H NMR (CDCl$_3$): δ 6.94 (d, J=7.6 Hz, 1H, 6H in indenyl), 6.81 (d, J=7.6 Hz, 1H, 5H in indenyl), 6.60 (s, 1H, 3-H in indenyl), 3.08 (s, 2H, 1,1-H in indenyl), 2.35 (s, 3H, 4-Me), 2.27 (s, 3H, 7-Me), 1.85 (m, 1H, 1-H in $^c$Pr), 0.89 (m, 2H, 2,3-H in $^c$Pr), 0.66 (m, 2H, 2',3'-H in $^c$Pr).

Bis(2-cyclopropyl-4,7-dimethyl-1H-inden-1-yl)dimethylsilane

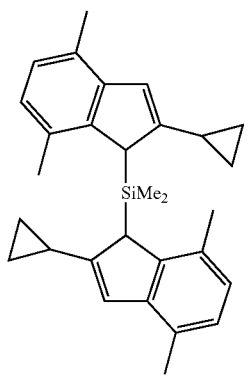

To a solution of 3.00 g (16.3 mmol) of 2-cyclopropyl-4,7-dimethyl-1H-indene in 100 ml of ether cooled to 0° C., 6.52 ml (16.3 mmol) of 2.5 M "BuLi in hexanes was added. This mixture was stirred for 12 h at room temperature, and then 15 ml of THF was added. The obtained mixture was cooled to −60° C., and then 0.073 g (0.82 mmol) of CuCN was added. Further on, this mixture was warmed to −30° C., stirred for 30 minutes at this temperature, then cooled to −60° C., and 0.98 ml (8.15 mmol) of dichlorodimethylsilane was added. The resulting mixture was stirred for 24 h at room temperature, and then 100 ml of water was added. The organic layer was separated, the aqueous layer was extracted with 2×50 ml of ethyl acetate. The combined organic extract was dried over Na$_2$SO$_4$ and then evaporated to dryness. Crude product was washed with 2×20 ml of hexanes and dried in vacuum. Yield 2.00 g (58%) of white powder of pure rac-compound. Calcd. for $C_{30}H_{36}Si$: C, 84.84; H, 8.54. Found: C, 85.11; H, 8.73. $^1$H NMR (CDCl$_3$): δ 6.87 (d, J=7.6 Hz, 2H, 6-H in indenyl), 6.76 (d, J=7.6 Hz, 2H, 5-H in indenyl), 6.38 (s, 2H, 3-H in indenyl), 4.37 (s, 2H, 1-H in indenyl), 2.34 (s, 6H, 4-Me), 2.29 (s, 6H, 7-Me), 1.95 (m, 2H, 1-H in $^c$Pr), 1.13 (m, 2H, 2/3-H in $^c$Pr), 1.10 (m, 2H, 2/3-H in $^c$Pr), 0.96 (m, 2H, 2/3-H in $^c$Pr), 0.80 (m, 2H, 2/3-H in $^c$Pr), −0.53 (s, 6H, SiMe$_2$).

rac-Dimethylsilylene-bis[2-cyclopropyl-4,7-dimethylinden-1-yl]hafnium dichloride (8)

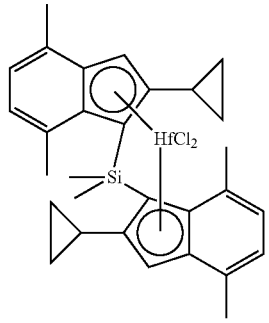

To a solution of 1.00 g (23.5 mmol) of bis(2-cyclopropyl-4,7-dimethyl-1H-inden-1-yl)dimethylsilane in 30 ml of ether cooled to 0° C., 1.90 ml (4.70 mmol) of 2.5 M "BuLi in hexanes was added. The obtained mixture was stirred for 12 h at room temperature, then cooled to −70° C., and 1.09 g (23.5 mmol) of HfCl$_4$(THF)$_2$ was added. This mixture was stirred overnight at room temperature and then filtered through glass frit (G4). The precipitate was dissolved in 50 ml of hot toluene, and the formed hot suspension was filtered through a Celite pad. The filtrate was concentrated in vacuum to 20 ml. Crystals precipitated from this solution at room temperature were collected and dried in vacuum. This procedure gave 0.35 g (22%) of pure rac-complex as yellow crystalline solid. Calcd. for $C_{30}H_{34}Cl_2HfSi$: C, 53.61; H, 5.10. Found: C, 53.71; H, 5.32. $^1$H NMR (CD$_2$Cl$_2$): δ 6.95 (d, J=6.8 Hz, 2H, 6-H in indenyl), 6.77 (d, J=6.8 Hz, 2H, 5-H in indenyl), 6.64 (s, 2H, 3-H in indenyl), 2.50 (s, 6H, 7-Me), 2.27 (s, 6H, 4-Me), 1.85 (m, 2H, 1-H in $^c$Pr), 1.41 (s, 6H, SiMe$_2$), 1.00 (m, 2H, 2/3-H in $^c$Pr), 0.90 (m, 2H, 2/3-H in $^c$Pr), 0.71 (m, 2H, 2/3-H in $^c$Pr), 0.40 (m, 2H, 2/3-H in $^c$Pr).

Example 9: Synthesis of rac-dimethylsilylene-bis[4-cyclopropyl-2-methylinden-1-yl]zirconium dichloride (9)

7-Cyclopropyl-2-methyl-1H-indene

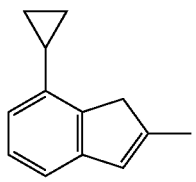

A mixture of 2.00 g (9.57 mmol) of 7-bromo-2-methyl-1H-indene, 0.11 g (0.19 mmol) of Pd(dba)$_2$, 0.077 g (0.38 mmol) of $^t$Bu$_3$P, and 15 ml of THF was stirred for 5 minutes at room temperature, and then 21.7 ml (14.4 mmol) of 0.66 M $^c$PrMgBr in THF was added for 5 minutes. The obtained mixture was stirred for 12 h at 60° C. and then poured into 50 ml of aqueous NH$_4$Cl. The organic layer was separated, and the aqueous layer was extracted with 3×20 ml of ethyl acetate. The combined organic extract was washed with 30 ml of brine, dried over Na$_2$SO$_4$, and evaporated to dryness. Crude product was purified by flash chromatography on silica gel 60 (40-63 um; eluent: hexanes). Yield 1.55 g (95%) of colorless oil. Calcd. for C$_{13}$H$_{14}$: C, 91.71; H, 8.29. Found: C, 91.60; H, 8.43. $^1$H NMR (CDCl$_3$): δ 7.14 (m, 1H, 5-H in indenyl), 7.07 (m, 1H, 4-H in indenyl), 6.64 (m, 1H, 7-H in indenyl), 6.49 (m, 1H, 3-H in indenyl), 3.35 (s, 2H, 1,1-H in indenyl), 2.18 (m, 3H, Me), 1.94 (m, 1H, 1-H in $^c$Pr), 0.94 (m, 2H, 2,3-H in $^c$Pr), 0.73 (m, 2H, 2',3'-H in $^c$Pr).

Bis(4-cyclopropyl-2-methyl-1H-inden-1-yl)(dimethyl)silane

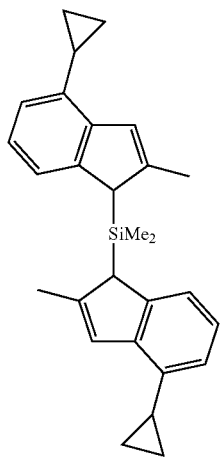

To a solution of 5.69 g (33.0 mmol) of 7-cyclopropyl-2-methyl-1H-indene in 100 ml of ether cooled to 0° C., 13.4 ml (33.0 mmol) of 2.5 M $^n$BuLi in hexanes was added. This mixture was stirred for 12 h at room temperature and then 20 ml of THF was added. The obtained mixture was cooled to −60° C., and 0.15 g (1.65 mmol) of CuCN was added. This mixture was warmed to −30° C., stirred for 30 minutes at this temperature, then cooled to −60° C., and 1.98 ml (16.5 mmol) of dichlorodimethylsilane was added. The resulting mixture was stirred for 24 h at room temperature, and then 40 ml of water was added. The organic layer was separated, the aqueous layer was extracted with 2×50 ml of ethyl acetate. The combined organic extract was dried over Na$_2$SO$_4$ and then evaporated to dryness. Crude product was purified by flash chromatography on silica gel 60 (40-63 um; eluent: hexanes-dichloromethane=10:1, vol.). Yield 4.17 g (63%) of yellow oil of a mixture of rac- and meso-compounds. Calcd. for C$_{28}$H$_{32}$Si: C, 84.79; H, 8.13. Found: C, 84.99; H, 8.39. $^1$H NMR (CDCl$_3$): δ 7.31 (m), 7.18 (m), 6.97-7.03 (m), 6.88 (m), 6.81 (m), 3.73 (s), 3.71 (s), 2.26 (s), 2.20 (s), 2.07-2.15 (m), 0.91-0.99 (m), 0.64-0.78 (m), −0.28 (s), −0.33 (s), −0.34 (s).

Rac-Dimethylsilylene-bis[4-cyclopropyl-2-methylinden-1-yl]zirconium dichloride (9)

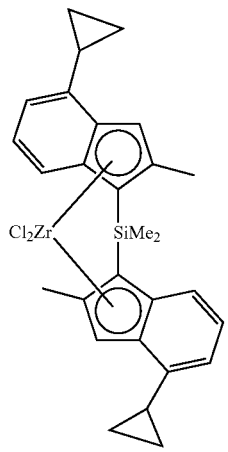

To a solution of 2.00 g (5.00 mmol) of bis-(4-cyclopropyl-2-methylinden-1-yl)dimethylsilane in 50 ml of ether cooled to 0° C., 4.00 ml (10.0 mmol) of 2.5 M $^n$BuLi in hexanes was added. This mixture was stirred for 12 h at room temperature, then cooled to −50° C., and 1.89 g (5.00 mmol) of ZrCl$_4$(THF)$_2$ was added. The obtained mixture was stirred overnight at room temperature and then filtered through glass frit (G4). The precipitate was poured into 50 ml of hot toluene, and the formed hot suspension was filtered through a Celite pad. The filtrate was concentrated in vacuum to 15 ml. Crystals precipitated from this solution at room temperature were collected and dried in vacuum. The obtained crystalline powder (in fact, a ca. 6.5 to 1 mixture of rac- and meso-complexes) was re-crystallized from 50 ml of toluene-methylcyclohexane (1:1, vol.) to give 0.36 g (13%) of pure rac-complex as red crystalline material. Calcd. for C$_{28}$H$_{30}$Cl$_2$SiZr: C, 60.40; H, 5.43. Found: C, 60.64; H, 5.69. $^1$H NMR (CD$_2$Cl$_2$): δ 7.51 (m, 2H, 7-H in indenyl), 6.92-6.98 (m, 6H, 3,5,6-H in indenyl), 2.23 (s, 6H, 2-Me), 1.94 (m, 2H, 1-H in $^c$Pr), 1.29 (s, 6H, SiMe$_2$), 0.83-0.96 (m, 6H, 2/3-H in $^c$Pr), 0.73 (m, 2H, 2/3-H in $^c$Pr).

Example 10: Synthesis of rac-cyclotetramethylen-esilylene-bis[4-cyclopropyl-2-methylinden-1-yl]hafnium dichloride (10)

1,1-Bis(4-cyclopropyl-2-methyl-1H-inden-1-yl)silolane

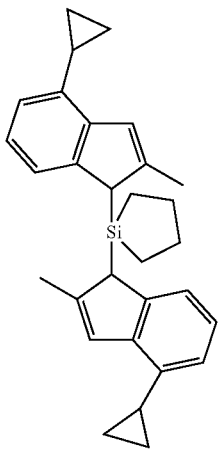 [SMILES: CC1=Cc2c(C3CC3)cccc2C1[Si]1(C2C(C)=Cc3c(C4CC4)cccc32)CCCC1]

To a solution of 5.40 g (32.0 mmol) of 7-cyclopropyl-2-methyl-1H-indene in 100 ml of ether cooled to 0° C., 12.8 ml (32.0 mmol) of 2.5 M $^n$BuLi in hexanes was added. This mixture was stirred for 12 h at room temperature, and then 11 ml of THF was added. The obtained mixture was cooled to −60° C., and 0.14 g (1.60 mmol) of CuCN was added. Then, this mixture was warmed to −30° C., stirred for 30 minutes at this temperature, cooled to −60° C., and 2.10 ml (16.0 mmol) of 1,1-dichlorosilolane was added. The resulting mixture was stirred for 24 h at room temperature, and then 40 ml of water was added. The organic layer was separated, the aqueous layer was extracted with 2×50 ml of ethyl acetate. The combined organic extract was dried over $Na_2SO_4$ and then evaporated to dryness. Crude product was purified by flash chromatography on silica gel 60 (40-63 um; eluent: hexanes-dichloromethane=10:1, vol.). Yield 4.73 g (70%) of yellow oil of a mixture of rac- and meso-compounds. Calcd. for $C_{30}H_{34}Si$: C, 85.25; H, 8.11. Found: C, 85.39; H, 8.27. $^1$H NMR (CDCl$_3$): δ 7.19 (m), 6.93-7.03 (m), 6.83 (m), 6.75-6.78 (m), 3.37 (s), 3.35 (s), 2.16 (s), 2.04-2.10 (m), 1.30-1.35 (m), 1.12-1.19 (m), 1.04-1.10 (m), 0.86-0.95 (m), 0.70-0.77 (m), 0.62-0.68 (m), 0.48-0.58 (m), 0.38 (m).

rac-Cyclotetramethylenesilylene-bis[4-cyclopropyl-2-methylinden-1-yl]hafnium dichloride (10)

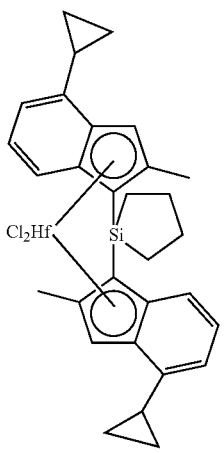

To a solution of 1.60 g (3.78 mmol) of 1,1-bis(4-cyclopropyl-2-methyl-1H-inden-1-yl)silolane in 50 ml of ether cooled to 0° C., 3.05 ml (7.56 mmol) of 2.5 M $^n$BuLi in hexanes was added. This mixture was stirred for 12 h at room temperature, then cooled to −50° C., and 1.75 g (3.78 mmol) of HfCl$_4$(THF)$_2$ was added. The obtained mixture was stirred overnight at room temperature and then filtered through glass frit (G4). The precipitate was poured into 100 ml of hot toluene, and the formed hot suspension was filtered through a Celite pad. The filtrate was concentrated in vacuum to 70 ml. Crystals precipitated from this solution at room temperature were collected and dried in vacuum. The obtained crystalline powder (in fact, a ca. 1 to 1 mixture of rac- and meso-complexes) was re-crystallized from 180 ml of toluene-ether (2:1, vol.) to give 0.51 g (20%) of pure rac-complex as yellow crystalline material. Calcd. for $C_{30}H_{32}Cl_2HfSi$: C, 53.77; H, 4.81. Found: C, 53.54; H, 4.69. $^1$H NMR (CD$_2$Cl$_2$): δ 7.46 (m, 2H, 7-H in indenyl), 6.87-6.94 (m, 4H, 5,6-H in indenyl), 6.83 (m, 2H, 3-H in indenyl), 2.28 (s, 6H, 2-Me), 2.11 (m, 2H, 3/3'-H in silolane), 1.87-2.01 (m, 8H, 1-H in $^c$Pr, 2,2'-H and 3/3'-H in silolane), 0.81-0.93 (m, 6H, 2/3-H in $^c$Pr), 0.67-0.73 (m, 2H, 2/3-H in cPr).

Example 11: Synthesis of dimethylsilylene-[2-cyclopropylinden-1-yl]-N-t-butylamidotitanium Dichloride (11)

Chloro(2-cyclopropyl-1H-inden-1-yl)dimethylsilane

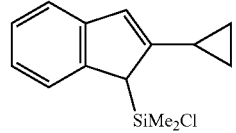

To a solution of 20.4 g (131 mmol) of 2-cyclopropyl-1H-indene in 225 ml of THF cooled to −80° C., 52.3 ml (131 mmol) of 2.5 M $^n$BuLi in hexanes was added. This mixture was stirred for 24 h at room temperature and then added to a solution of 47.0 ml (393 mmol) of dichlorodimethylsilane in 75 ml of THF by vigorous stirring for 3 h at room temperature. The obtained mixture was stirred for 48 h at room temperature and then evaporated to dryness. Vacuum distillation of the residue gave 20.2 g (62%) of yellow oil, b.p. 118-122° C./1 mm Hg. Calcd. for $C_{19}H_{27}ClSi$: C, 67.58; H, 6.89. Found: C, 67.75; H, 6.48. $^1$H NMR (CDCl$_3$): δ 7.52 (m, 1H, 7-H in indenyl), 7.31 (m, 1H, 4-H in indenyl), 7.23 (m, 1H, 5-H in indenyl), 7.12 (m, 1H, 6-H in indenyl), 6.36 (s, 1H, 3-H in indenyl), 3.78 (s, 1H, 1-H in indenyl), 1.77 (m, 1H, 1-H in $^c$Pr), 1.00 (m, 2H, 2,3-H in $^c$Pr), 0.74 (m, 2H, 2',3'-H in $^c$Pr), 0.34 (s, 3H, SiMeMe'), 0.28 (s, 3H, SiMeMe').

tert-Butyl[(2-cyclopropyl-1H-inden-1-yl)dimethylsilyl]amine

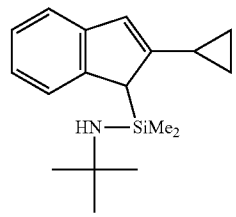

To a solution of 20.0 g (80.0 mmol) of chloro(2-cyclopropyl-1H-inden-1-yl)dimethylsilane in 150 ml of THF, 25.0 ml (240 mmol) of t-butylamine was added at room temperature. This mixture was stirred for 12 h at room temperature and then evaporated to dryness. Vacuum distillation of the residue gave 18.0 g (79%) of colorless oil, b.p. 138-142° C./1 mm Hg. Calcd. for $C_{23}H_{37}NSi$: C, 75.72; H, 9.53; N, 4.91. Found: C, 75.54; H, 9.42; N, 5.12. $^1$H NMR ($CDCl_3$): δ 7.46 (m, 1H, 7-H in indenyl), 7.29 (m, 1H, 4-H in indenyl), 7.18 (m, 1H, 5-H in indenyl), 7.07 (m, 1H, 6-H in indenyl), 6.30 (s, 1H, 3-H in indenyl), 3.61 (s, 1H, 1-H in indenyl), 1.81 (m, 1H, 1-H in $^c$Pr), 1.21 (s, 9H, $^t$Bu), 0.95 (m, 2H, 2,3-H in $^c$Pr), 0.73 (m, 2H, 2',3'-H in $^c$Pr), 0.06 (s, 3H, SiMeMe'), 0.05 (s, 3H, SiMeMe').

Dimethylsilylene-[2-cyclopropylinden-1-yl]-N-t-butylamidotitanium dichloride (11)

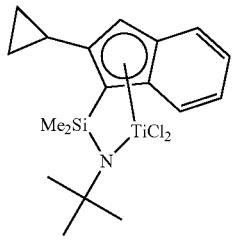

To a solution of 5.00 g (17.5 mmol) of tert-butyl[(2-cyclopropyl-1H-inden-1-yl)dimethylsilyl]amine in 100 ml of ether cooled to 0° C., 14.0 ml (35.0 mmol) of 2.5 M $^n$BuLi in hexanes was added. The resulting mixture was stirred for 12 h at room temperature, then cooled to −80° C., and 1.93 ml (3.33 g, 17.5 mmol) of $TiCl_4$ was added. The obtained mixture was stirred overnight at room temperature and then evaporated to dryness. The residue was poured into 100 ml of toluene, and the formed suspension was filtered through a Celite pad. The filtrate was concentrated in vacuum to 10 ml, and 50 ml of hexane was added. This mixture was heated to dissolve the precipitate and then was left at room temperature. Crystals precipitated from this solution were collected and dried in vacuum. Yield 3.31 g (47%) of dark red crystalline powder. Calcd. for $C_{23}H_{35}Cl_2NSiTi$: C, 53.75; H, 6.26; N, 3.48. Found: C, 53.64; H, 6.46; N, 3.30. $^1$H NMR ($CD_2Cl_2$): δ 7.75 (m, 1H, 7-H in indenyl), 7.62 (m, 1H, 4-H in indenyl), 7.35 (m, 1H, 5-H in indenyl), 7.23 (m, 1H, 6-H in indenyl), 6.91 (s, 1H, 3-H in indenyl), 1.97 (m, 1H, 1-H in $^c$Pr), 1.38 (s, 9H, $^t$Bu), 1.19 (m, 1H, 2/3-H in $^c$Pr), 1.07 (m, 1H, 2/3-H in $^c$Pr), 1.00 (m, 1H, 2/3-H in $^c$Pr), 0.93 (s, 3H, SiMeMe'), 0.87 (s, 3H, SiMeMe'), 0.65 (m, 1H, 2/3-H in $^c$Pr).

Example 12: Synthesis of dimethylsilylene-[2-cyclopropylinden-1-yl]-N-t-butylamidozirconium Dichloride (12)

Dimethylsilylene-[2-cyclopropylinden-1-yl]-N-t-butylamidozirconium Dichloride (12)

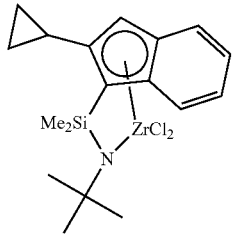

To a solution of 2.50 g (8.75 mmol) of tert-butyl[(2-cyclopropyl-1H-inden-1-yl)dimethylsilyl]amine in 50 ml of ether cooled to 0° C., 7.00 ml (17.5 mmol) of 2.5 M $^n$BuLi in hexanes was added. The obtained mixture was stirred for 12 h at room temperature, then cooled to −70° C., and 3.30 g (8.75 mmol) of $ZrCl_4(THF)_2$ was added. The resulting mixture was stirred overnight at room temperature and then evaporated to dryness. The residue was poured into 50 ml of toluene, and the formed suspension was filtered through a Celite pad. The filtrate was concentrated in vacuum to 5 ml, and then 25 ml of hexane was added. This mixture was heated to dissolve the precipitate and then left at room temperature. Crystals precipitated from this solution were collected and dried in vacuum. Yield 1.35 g (35%) of yellow crystalline powder. Calcd. for $C_{23}H_{35}Cl_2NSiZr$: C, 48.52; H, 5.65; N, 3.14. Found: C, 48.51; H, 5.89; N, 3.02. $^1$H NMR ($CD_2Cl_2$): δ 7.76 (m, 1H, 7-H in indenyl), 7.67 (m, 1H, 4-H in indenyl), 7.29 (m, 1H, 5-H in indenyl), 7.21 (m, 1H, 6-H in indenyl), 6.69 (s, 1H, 3-H in indenyl), 1.99 (m, 1H, 1-H in $^c$Pr), 1.36 (s, 9H, $^t$Bu), 1.16 (m, 1H, 2/3-H in $^c$Pr), 1.08 (m, 1H, 2/3-H in $^c$Pr), 1.01 (m, 1H, 2/3-H in $^c$Pr), 0.90 (s, 3H, SiMeMe'), 0.81 (s, 3H, SiMeMe'), 0.65 (m, 1H, 2/3-H in $^c$Pr).

Comparative compounds used in the following polymerization examples include:
rac-$Me_2Si(2-Me-4-EtInd)_2ZrCl_2$ (Catalyst ID in tables, CB)
rac-$(CH_2)_4Si(2-Me-4-iPrInd)_2HfCl_2$ (Catalyst ID in tables, CC),
wherein Ind=indenyl, Me=methyl, Et—ethyl, iPr=isopropyl.

Polymerization Examples

Solutions of the pre-catalysts (Compound 1 to 12, prepared above) were made using toluene (ExxonMobil Chemical—anhydrous, stored under $N_2$) (98%). Pre-catalyst solutions were typically 0.5 mmol/L. When noted, some pre-catalysts were pre-alkylated using triisobutyl aluminum (TiBAl, neat, AkzoNobel); prealkylation was preformed by first dissolving the pre-catalyst in the appropriate amount of toluene, and then adding 20 equivalents of TiBAl such that the final pre-catalyst solution was 0.5 mmol precatalyst/L and 10 mmol TiBAl/L.

Solvents, polymerization grade toluene and/or isohexanes were supplied by ExxonMobil Chemical Co. and are purified by passing through a series of columns: two 500 cc Oxyclear cylinders in series from Labclear (Oakland, Calif.), followed by two 500 cc columns in series packed with dried 3 Å mole sieves (8-12 mesh; Aldrich Chemical Company), and two 500 cc columns in series packed with dried 5 Å mole sieves (8-12 mesh; Aldrich Chemical Company).

1-octene (98%) (Aldrich Chemical Company) was dried by stirring over NaK overnight followed by filtration through basic alumina (Aldrich Chemical Company, Brockman Basic 1).

Polymerization grade ethylene was used and further purified by passing it through a series of columns: 500 cc Oxyclear cylinder from Labclear (Oakland, Calif.) followed by a 500 cc column packed with dried 3 Å mole sieves (8-12 mesh; Aldrich Chemical Company), and a 500 cc column packed with dried 5 Å mole sieves (8-12 mesh; Aldrich Chemical Company).

Polymerization grade propylene was used and further purified by passing it through a series of columns: 2250cc Oxiclear cylinder from Labclear followed by a 2250cc column packed with 3 Å mole sieves (8-12 mesh; Aldrich Chemical Company), then two 500cc columns in series packed with 5 Å mole sieves (8-12 mesh; Aldrich Chemical Company), the a 500cc column packed with Selexsorb CD (BASF), and finally a 500cc column packed with Selexsorb COS (BASF).

Activation of the pre-catalysts was either by methylalumoxane (MAO, 10 wt % in toluene, Albemarle Corp.) or dimethylanilinium tetrakisperfluorophenylborate (Boulder Scientific and Albemarle Corp). MAO was used as a 0.5 wt % or 1.0 wt % in toluene solution. Micromoles of MAO reported in the experimental section are based on the micromoles of aluminum in MAO. The formula weight of MAO is 58.0 grams/mole. Dimethylanilinium tetrakisperfluorophenylborate was typically used as a 5 mmol/L solution in toluene.

For polymerization runs using dimethylanilinium tetrakisperfluorophenylborate, tri-n-octylaluminum (TnOAl, Neat, AkzoNobel) was also used as a scavenger prior to introduction of the activator and pre-catalyst into the reactor. TnOAl was typically used as a 5 mmol/L solution in toluene.

Reactor Description and Preparation:

Polymerizations were conducted in an inert atmosphere ($N_2$) drybox using autoclaves equipped with an external heater for temperature control, glass inserts (internal volume of reactor=23.5 mL for $C_2$ and $C_2/C_8$ runs; 22.5 mL for $C_3$ and $C_2/C_3$ runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours.

Ethylene Polymerization (PE) or Ethylene/1-octene Copolymerization (EO):

The reactor was prepared as described above, and then purged with ethylene. For MAO activated runs, toluene, 1-octene (100 µL when used), and activator (MAO) were added via syringe at room temperature and atmospheric pressure. The reactor was then brought to process temperature (80° C.) and charged with ethylene to process pressure (75 psig=618.5 kPa or 200 psig=1480.3 kPa) while stirring at 800 RPM. The pre-catalyst solution was then added via syringe to the reactor at process conditions. For dimethylanilinium tetrakisperfluorophenylborate activated runs, toluene, 1-octene (100 µL when used) and scavenger (TnOAl, 0.5 µmol) were added via syringe at room temperature and atmospheric pressure. The reactor was then brought to process temperature (80° C.) and charged with ethylene to process pressure (75 psig=618.5 kPa or 200 psig=1480.3 kPa) while stirring at 800 RPM. The activator solution, followed by the pre-catalyst solution, were injected via syringe to the reactor at process conditions. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psi $O_2$/Ar (5 mole % O2) gas mixture to the autoclaves for approximately 30 seconds. The polymerizations were quenched after a predetermined cumulative amount of ethylene had been added or for a maximum of 30 minutes polymerization time. The reactors were cooled and vented. The polymer was isolated after the solvent was removed in-vacuo. The final conversion (quench value in psi) of ethylene added/consumed is reported in the Tables 1 (PE) and 2a (EO), in addition to the quench time for each run. Yields reported include total weight of polymer and residual catalyst. Catalyst activity is reported as grams of polymer per mmol transition metal compound per hour of reaction time (g/mmol*hr).

Propylene Polymerization:

The reactor was prepared as described above, then heated to 40° C. and then purged with propylene gas at atmospheric pressure. For MAO activated runs, toluene, MAO, and liquid propylene (1.0 mL) were added via syringe. The reactor was then heated to process temperature (70° C. or 100° C.) while stirring at 800 RPM. The pre-catalyst solution was added via syringe with the reactor at process conditions. For dimethylanilinium tetrakisperfluorophenylborate activated runs, isohexanes, liquid propylene (1.0 mL) and scavenger (TnOAl, 0.5 µmol) were added via syringe. The reactor was then brought to process temperature (70° C. or 100° C.) while stirring at 800 RPM. The activator solution, followed by the pre-catalyst solution, were injected via syringe to the reactor at process conditions. Reactor temperature was monitored and typically maintained within +/−1° C. Polymerizations were halted by addition of approximately 50 psi $O_2$/Ar (5 mole % O2) gas mixture to the autoclaves for approximately 30 seconds. The polymerizations were quenched based on a predetermined pressure loss of approximately 8-15 psi or for a maximum of 30 minutes polymerization time. The reactors were cooled and vented. The polymer was isolated after the solvent was removed in-vacuo. The quench time (s) and quench value (psi) are reported in Table 3a for each run. Yields reported include total weight of polymer and residual catalyst. Catalyst activity is reported as grams of polymer per mmol transition metal compound per hour of reaction time (g/mmol*hr).

Polymer Characterization

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB. Samples were cooled to 135° C. for testing.

High temperature size exclusion chromatography was performed using an automated "Rapid GPC" system as described in U.S. Pat. Nos. 6,491,816; 6,491,823; 6,475,391; 6,461,515; 6,436,292; 6,406,632; 6,175,409; 6,454,947; 6,260,407; and 6,294,388; each of which is incorporated herein by reference. Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). Samples (250 µL of a polymer solution in TCB were injected into the system) were run at an eluent flow rate of 2.0 mL/minute (135° C. sample temperatures, 165° C. oven/columns) using three Polymer Laboratories: PLgel 10 µm Mixed-B 300×7.5 mm columns in series. No column spreading corrections were employed. Numerical analyses were performed using Epoch® software available from Symyx Technologies. The molecular weights obtained are relative to linear polystyrene standards. Molecular weight data is reported in Tables 1, 2b and 3b.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minute and then cooled at a rate of 50° C./minute. Melting points were collected during the heating period. The results are reported in the tables 1, 2b and 3b as $T_m$ (° C.).

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes' MappIR specular reflectance sample accessory. Spectra, covering a spectral range of 5000 cm$^{-1}$ to 500 cm$^{-1}$, were collected at a 2 cm$^{-1}$ resolution with 32 scans.

For ethylene-1-octene copolymers, the wt % copolymer was determined via measurement of the methyl deformation band at ~1375 cm$^{-1}$. The peak height of this band was normalized by the combination and overtone band at ~4321 cm$^{-1}$, which corrects for path length differences. The normalized peak height was correlated to individual calibration curves from $^1$H NMR data to predict the wt % copolymer content within a concentration range of ~2 to 35 wt % for octene. Typically, $R^2$ correlations of 0.98 or greater are achieved. These numbers are reported in Table 2a under the heading C8 wt %).

$^{13}$C NMR spectroscopy was used to characterize some polymer samples. Unless otherwise indicated the Polymer samples for $^{13}$C NMR spectroscopy were dissolved in d$_2$-1,1,2,2-tetrachloroethane and the samples were recorded at 125° C. using a NMR spectrometer with a $^{13}$C NMR frequency of 100 or 175 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J. Randall in "Polymer Sequence Determination, Carbon-13 NMR Method", Academic Press, New York, 1977.

The stereodefects measured as "stereo defects/10,000 monomer units" is calculated from the sum of the intensities of mmrr, mmrm+rrmr, and rmrm resonance peaks times 5000. The intensities used in the calculations are normalized to the total number of monomers in the sample.

Polymerization results are collected in Tables 1, 2a, 2b, 3a, and 3b below. "Ex#" stands for example number. Examples starting with a "C" are comparative examples. "Cat ID" indentifies the pre-catalyst used in the experiment. Corresponding numbers identifying the pre-catalyst are located in the synthetic experimental section. An asterisk next to the Cat ID number indicates that the pre-catalyst was pre-alkylated with 20 equivalents of TiBAl. "Act ID" indentifies the activator used. "A" corresponds to MAO and "B" corresponds to dimethylanilinium tetrakisperfluorophenylborate. "Cat (µmol)" is the amount of pre-catalyst added to the reactor. "Act/Cat (µmol) is the molar ratio of activator/pre-catalyst used in the experiment. "Yield" is polymer yield, and is not corrected for catalyst residue. "Quench time (s)" is the actual duration of the polymerization run in seconds. "Quench Value (psi)" for ethylene based polymerization runs is the set maximum amount of ethylene uptake (conversion) for the experiment. If a polymerization quench time is 30 minutes or less, then the polymerization ran until the set maximum value of ethylene uptake was reached. For propylene based polymerization runs, quench value indicates the pressure loss (conversion) of propylene during the polymerization.

$^{13}$C NMR spectroscopy is used to characterize some polymer samples. The polymer samples for $^{13}$C NMR spectroscopy are dissolved in a mixture of 1,2,4-trichlorobenzene and deuterobenzene and the samples are recorded at 125° C. using a NMR spectrometer with a $^{13}$C NMR frequency of 150 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J. Randall in "Polymer Sequence Determination, Carbon-13 NMR Method", Academic Press, New York, 1977. The stereodefects measured as "stereo defects/10,000 monomer units" are calculated from the sum of the intensities of mmrr, mmrm+rrmr, and rmrm resonance peaks times 5000. The intensities used in the calculations are normalized to the total number of monomers in the sample.

TABLE 1

Ethylene polymerization examples

| Ex # | Cat ID | Act ID | Cat (µmol) | Act/Cat (molar) | yield (g) | quench time (s) | Catalyst Activity (g/mmol · hr) | Mn | Mw | Mw/Mn | $T_m$ (° C.) |
|---|---|---|---|---|---|---|---|---|---|---|---|
| PE-1 | 1* | B | 0.030 | 1.1 | 0.0385 | 173 | 31,991 | 268,541 | 755,333 | 2.81 | 137.0 |
| PE-2 | 1* | B | 0.030 | 1.1 | 0.0446 | 179 | 35,799 | 289,569 | 774,273 | 2.67 | 136.8 |
| PE-3 | 1* | B | 0.030 | 1.1 | 0.0425 | 195 | 31,320 | 355,803 | 894,928 | 2.52 | 136.9 |
| PE-4 | 1 | A | 0.030 | 500 | 0.0632 | 95 | 95,597 | 197,092 | 860,897 | 4.37 | 136.6 |
| PE-5 | 1 | A | 0.030 | 500 | 0.0707 | 329 | 30,916 | 170,492 | 867,942 | 5.09 | 137.0 |
| PE-6 | 1 | A | 0.030 | 500 | 0.0746 | 306 | 35,106 | 181,152 | 816,227 | 4.51 | 136.8 |
| PE-7 | 2 | B | 0.025 | 1.1 | 0.0865 | 117 | 106,371 | 676,155 | 1,169,206 | 1.73 | 133.6 |
| PE-8 | 2 | B | 0.025 | 1.1 | 0.0864 | 128 | 97,124 | 586,884 | 929,135 | 1.58 | 132.3 |
| PE-9 | 2 | B | 0.025 | 1.1 | 0.0833 | 105 | 114,458 | 698,667 | 1,248,328 | 1.79 | 133.8 |
| PE-10 | 2 | A | 0.025 | 500 | 0.1147 | 124 | 133,415 | 603,418 | 1,043,613 | 1.73 | 134.0 |
| PE-11 | 2 | A | 0.025 | 500 | 0.0995 | 114 | 126,238 | 649,456 | 1,088,906 | 1.68 | 133.1 |
| PE-12 | 2 | A | 0.025 | 500 | 0.0990 | 112 | 127,286 | 663,902 | 1,056,953 | 1.59 | 133.9 |
| PE-13 | 2 | A | 0.020 | 500 | 0.1082 | 173 | 112,318 | 741,735 | 1,088,791 | 1.47 | 134.3 |
| PE-14 | 2 | A | 0.020 | 500 | 0.0936 | 139 | 121,034 | 745,028 | 1,085,903 | 1.46 | 133.6 |
| PE-15 | 2 | A | 0.020 | 500 | 0.0937 | 143 | 117,697 | 764,229 | 1,105,205 | 1.45 | 134.1 |
| PE-16 | 3* | B | 0.030 | 1.1 | 0.0860 | 159 | 77,789 | 924,972 | 1,326,065 | 1.43 | 133.5 |
| PE-17 | 3* | B | 0.030 | 1.1 | 0.0877 | 162 | 77,764 | 761,289 | 1,055,337 | 1.39 | 132.7 |
| PE-18 | 3* | B | 0.030 | 1.1 | 0.0852 | 155 | 79,001 | 890,742 | 1,249,632 | 1.40 | 133.8 |
| PE-19 | 3 | A | 0.030 | 500 | 0.0989 | 114 | 124,817 | 697,371 | 1,457,395 | 2.09 | 133.0 |
| PE-20 | 3 | A | 0.030 | 500 | 0.0963 | 114 | 121,217 | na | na | na | 132.8 |
| PE-21 | 3 | A | 0.030 | 500 | 0.0994 | 75 | 192,129 | 831,991 | 2,868,998 | 3.45 | 133.0 |
| PE-22 | 3 | A | 0.020 | 500 | 0.0879 | 142 | 111,658 | 723,929 | 1,053,935 | 1.46 | 133.1 |

TABLE 1-continued

Ethylene polymerization examples

| Ex # | Cat ID | Act ID | Cat (μmol) | Act/Cat (molar) | yield (g) | quench time (s) | Catalyst Activity (g/mmol · hr) | Mn | Mw | Mw/Mn | $T_m$ (° C.) |
|---|---|---|---|---|---|---|---|---|---|---|---|
| PE-23 | 3 | A | 0.020 | 500 | 0.0903 | 144 | 112,797 | 759,751 | 1,103,007 | 1.45 | 134.4 |
| PE-24 | 3 | A | 0.020 | 500 | 0.0898 | 124 | 130,883 | 757,727 | 1,089,829 | 1.44 | 133.9 |
| PE-25 | 4* | B | 0.030 | 1.1 | 0.0990 | 115 | 124,398 | 454,543 | 715,779 | 1.57 | 134.0 |
| PE-26 | 4* | B | 0.030 | 1.1 | 0.0647 | 72 | 128,863 | 348,169 | 526,955 | 1.51 | 134.3 |
| PE-27 | 4* | B | 0.030 | 1.1 | 0.0756 | 77 | 141,566 | 381,029 | 592,805 | 1.56 | 134.6 |
| PE-28 | 4 | A | 0.030 | 500 | 0.1028 | 135 | 109,653 | 585,116 | 1,129,749 | 1.93 | 133.6 |
| PE-29 | 4 | A | 0.030 | 500 | 0.0968 | 136 | 102,494 | 577,491 | 1,777,986 | 3.08 | 132.9 |
| PE-30 | 4 | A | 0.030 | 500 | 0.1019 | 142 | 103,045 | 589,451 | 1,452,783 | 2.46 | na |
| PE-31 | 4 | A | 0.020 | 500 | 0.0906 | 174 | 93,724 | 751,890 | 1,162,390 | 1.55 | 134.5 |
| PE-32 | 4 | A | 0.020 | 500 | 0.0892 | 134 | 119,732 | 690,403 | 1,041,126 | 1.51 | 133.9 |
| PE-33 | 4 | A | 0.020 | 500 | 0.0907 | 181 | 90,000 | 734,845 | 1,103,120 | 1.50 | 134.3 |
| PE-34 | 5* | B | 0.030 | 1.1 | 0.0828 | 49 | 245,839 | 290,448 | 470,500 | 1.62 | 134.3 |
| PE-35 | 5* | B | 0.030 | 1.1 | 0.0817 | 47 | 248,727 | 269,006 | 437,134 | 1.62 | 132.8 |
| PE-36 | 5* | B | 0.030 | 1.1 | 0.0800 | 50 | 229,482 | 298,913 | 478,743 | 1.60 | 134.0 |
| PE-37 | 5 | A | 0.030 | 500 | 0.0995 | 123 | 116,963 | 286,130 | 701,637 | 2.45 | 132.9 |
| PE-38 | 5 | A | 0.030 | 500 | 0.0974 | 124 | 113,384 | 347,541 | 740,226 | 2.13 | 132.1 |
| PE-39 | 5 | A | 0.030 | 500 | 0.1008 | 126 | 115,567 | 393,998 | 917,888 | 2.33 | 132.9 |
| PE-40 | 5 | A | 0.020 | 500 | 0.0880 | 55 | 286,957 | 291,293 | 440,363 | 1.51 | 132.9 |
| PE-41 | 5 | A | 0.020 | 500 | 0.0822 | 52 | 283,448 | 274,677 | 403,133 | 1.47 | 133.3 |
| PE-42 | 5 | A | 0.020 | 500 | 0.0874 | 49 | 322,377 | 278,900 | 417,133 | 1.50 | 133.2 |
| PE-43 | 6* | B | 0.030 | 1.1 | 0.0705 | 172 | 59,092 | 254,921 | 392,596 | 1.54 | 133.7 |
| PE-44 | 6* | B | 0.030 | 1.1 | 0.0704 | 193 | 52,581 | 262,988 | 401,265 | 1.53 | 134.5 |
| PE-45 | 6* | B | 0.030 | 1.1 | 0.0667 | 188 | 51,198 | 248,950 | 381,672 | 1.53 | 133.5 |
| PE-46 | 6 | A | 0.030 | 500 | 0.0933 | 104 | 129,434 | 250,896 | 640,664 | 2.55 | 132.3 |
| PE-47 | 6 | A | 0.030 | 500 | 0.0992 | 107 | 134,004 | 255,047 | 731,330 | 2.87 | 133.7 |
| PE-48 | 6 | A | 0.030 | 500 | 0.0929 | 65 | 206,764 | 280,509 | 581,506 | 2.07 | 132.7 |
| PE-49 | 6 | A | 0.020 | 500 | 0.0750 | 146 | 92,402 | 263,314 | 399,908 | 1.52 | 133.4 |
| PE-50 | 6 | A | 0.020 | 500 | 0.0788 | 127 | 111,861 | 271,860 | 422,174 | 1.55 | 132.8 |
| PE-51 | 6 | A | 0.020 | 500 | 0.0781 | 128 | 109,828 | 263,472 | 413,927 | 1.57 | 131.3 |
| PE-52 | 7a | A | 0.030 | 500 | 0.0924 | 185 | 71,883 | 556,440 | 1,098,199 | 1.97 | 132.9 |
| PE-53 | 7a | A | 0.030 | 500 | 0.1003 | 163 | 88,881 | 590,450 | 1,249,503 | 2.12 | 133.5 |
| PE-54 | 7a | A | 0.030 | 500 | 0.0991 | 167 | 85,708 | 442,335 | 1,171,124 | 2.65 | 132.2 |
| PE-55 | 7a | A | 0.020 | 500 | 0.0862 | 151 | 102,755 | 562,082 | 881,828 | 1.57 | 134.0 |
| PE-56 | 7a | A | 0.020 | 500 | 0.0889 | 214 | 74,706 | 582,653 | 924,700 | 1.59 | 133.7 |
| PE-57 | 7b | A | 0.030 | 500 | 0.1018 | 92 | 159,166 | 479,594 | 2,957,847 | 6.17 | 133.9 |
| PE-58 | 7b | A | 0.030 | 500 | 0.0974 | 107 | 131,696 | 678,171 | 1,470,081 | 2.17 | 137.8 |
| PE-59 | 7b | A | 0.030 | 500 | 0.1014 | 119 | 123,013 | 693,059 | 1,543,023 | 2.23 | 133.1 |
| PE-60 | 7b | A | 0.020 | 500 | 0.0891 | 110 | 145,272 | 797,778 | 1,176,402 | 1.47 | 133.9 |
| PE-61 | 7b | A | 0.020 | 500 | 0.0881 | 116 | 136,589 | 731,860 | 1,078,382 | 1.47 | 132.6 |
| PE-62 | 7b | A | 0.020 | 500 | 0.0888 | 128 | 125,168 | 874,166 | 1,473,321 | 1.69 | 134.0 |
| PE-63 | 8* | B | 0.030 | 1.1 | 0.0738 | 101 | 105,220 | 359,857 | 772,471 | 2.15 | 135.5 |
| PE-64 | 8* | B | 0.030 | 1.1 | 0.0692 | 76 | 131,116 | 321,643 | 683,859 | 2.13 | 134.9 |
| PE-65 | 8* | B | 0.030 | 1.1 | 0.0728 | 105 | 100,126 | 380,334 | 799,836 | 2.10 | 135.4 |
| PE-66 | 8 | A | 0.030 | 500 | 0.0931 | 146 | 91,574 | 471,568 | 804,304 | 1.71 | 135.4 |
| PE-67 | 8 | A | 0.030 | 500 | 0.0910 | 179 | 73,125 | 476,429 | 773,626 | 1.62 | 134.4 |
| PE-68 | 8 | A | 0.030 | 500 | 0.0885 | 144 | 88,623 | 436,397 | 802,643 | 1.84 | 135.7 |
| PE-69 | 9* | B | 0.030 | 1.1 | 0.0871 | 70 | 179,948 | 364,619 | 584,825 | 1.60 | 133.9 |
| PE-70 | 9* | B | 0.030 | 1.1 | 0.0852 | 88 | 139,102 | 390,529 | 620,479 | 1.59 | 134.8 |
| PE-71 | 9* | B | 0.030 | 1.1 | 0.0894 | 75 | 171,877 | 362,666 | 581,291 | 1.60 | 134.2 |
| PE-72 | 9 | A | 0.030 | 500 | 0.0945 | 111 | 122,927 | 513,510 | 763,998 | 1.49 | 133.3 |
| PE-73 | 9 | A | 0.030 | 500 | 0.0926 | 140 | 94,974 | 546,689 | 815,685 | 1.49 | 135.1 |
| PE-74 | 9 | A | 0.030 | 500 | 0.0971 | 125 | 111,591 | 517,524 | 775,904 | 1.50 | 134.4 |
| PE-75 | 10* | B | 0.025 | 1.1 | 0.0812 | 375 | 31,189 | 811,715 | 1,462,489 | 1.80 | 135.5 |
| PE-76 | 10* | B | 0.025 | 1.1 | 0.0740 | 235 | 45,306 | 609,737 | 1,189,969 | 1.95 | 136.7 |
| PE-77 | 10* | B | 0.025 | 1.1 | 0.0825 | 232 | 51,295 | 947,685 | 1,734,465 | 1.83 | 135.0 |
| PE-78 | 10 | A | 0.030 | 500 | 0.0881 | 306 | 41,418 | 695,123 | 1,437,092 | 2.07 | 133.4 |
| PE-79 | 10 | A | 0.030 | 500 | 0.0839 | 296 | 40,871 | 679,857 | 1,459,137 | 2.15 | 134.7 |
| PE-80 | 10 | A | 0.030 | 500 | 0.0855 | 277 | 44,512 | 668,907 | 1,322,131 | 1.98 | 133.9 |
| PE-81 | 11* | B | 0.030 | 1.1 | 0.0347 | 1366 | 3,658 | 2,042,476 | 3,175,009 | 1.55 | 133.1 |
| PE-82 | 11* | B | 0.030 | 1.1 | 0.0333 | 1801 | 2,663 | 1,893,528 | 3,012,620 | 1.59 | 134.7 |
| PE-83 | 11* | B | 0.030 | 1.1 | 0.0323 | 1796 | 2,590 | 2,019,975 | 3,107,622 | 1.54 | 133.3 |
| PE-84 | 11 | A | 0.030 | 500 | 0.0709 | 476 | 21,444 | 164,713 | 1,098,553 | 6.67 | 134.3 |
| PE-85 | 11 | A | 0.030 | 500 | 0.0719 | 351 | 29,522 | 417,102 | 947,608 | 2.27 | 134.2 |
| PE-86 | 11 | A | 0.030 | 500 | 0.0692 | 427 | 23,337 | 294,231 | 954,790 | 3.25 | na |
| PE-87 | 12* | B | 0.030 | 1.1 | 0.0287 | 664 | 6,225 | 1,614 | 1,753 | 1.09 | 124.6 |
| PE-88 | 12* | B | 0.030 | 1.1 | 0.0316 | 631 | 7,210 | 1,670 | 1,799 | 1.08 | 124.9 |
| PE-89 | 12* | B | 0.030 | 1.1 | 0.0270 | 604 | 6,437 | 1,613 | 1,767 | 1.10 | 124.7 |
| PE-90 | 12 | A | 0.030 | 500 | 0.0397 | 1235 | 4,629 | 13,952 | 1,714,249 | 122.9 | 133.8 |
| PE-91 | 12 | A | 0.030 | 500 | 0.0404 | 1406 | 4,138 | 7,492 | 1,342,242 | 179.2 | 133.4 |
| PE-92 | 12 | A | 0.030 | 500 | 0.0343 | 648 | 7,625 | 19,861 | 1,758,458 | 88.5 | 134.4 |
| C-1 | CB | A | 0.030 | 500 | 0.0882 | 82 | 154,699 | 428,464 | 608,210 | 1.42 | 135.7 |
| C-2 | CB | A | 0.030 | 500 | 0.0893 | 96 | 133,394 | 461,497 | 668,352 | 1.45 | 135.7 |
| C-3 | CB | A | 0.030 | 500 | 0.0889 | 80 | 160,421 | 441,209 | 627,877 | 1.42 | 135.5 |

TABLE 1-continued

Ethylene polymerization examples

| Ex # | Cat ID | Act ID | Cat (μmol) | Act/Cat (molar) | yield (g) | quench time (s) | Catalyst Activity (g/mmol · hr) | Mn | Mw | Mw/Mn | $T_m$ (° C.) |
|---|---|---|---|---|---|---|---|---|---|---|---|
| C-4 | CC* | B | 0.025 | 1.1 | 0.0846 | 191 | 63,883 | 538,250 | 1,025,989 | 1.91 | 136.6 |
| C-5 | CC* | B | 0.025 | 1.1 | 0.0826 | 262 | 45,347 | 547,733 | 1,012,506 | 1.85 | 136.2 |
| C-6 | CC* | B | 0.025 | 1.1 | 0.0801 | 230 | 50,215 | 505,738 | 937,411 | 1.85 | 99.6 |
| C-7 | CC | A | 0.030 | 500 | 0.0926 | 194 | 68,699 | 674,417 | 948,245 | 1.41 | 134.4 |
| C-8 | CC | A | 0.030 | 500 | 0.0884 | 109 | 117,000 | 655,584 | 929,683 | 1.42 | 136.2 |
| C-9 | CC | A | 0.030 | 500 | 0.0930 | 226 | 59,204 | 710,923 | 1,013,839 | 1.43 | 134.0 |

For all runs, the total amount of toluene added to the reactor was 5 ml, the ethylene pressure was maintained at 75 psig of ethylene, and the quench value was set to 20 psi. "na" indicates that the data was not available.

TABLE 2a

Ethylene-Octene copolymerization examples - Part 1

| Ex # | Cat ID | Act ID | Cat (μmol) | Act/Cat (molar) | $C2^=$ (psig) | Quench value (psi) | yield (g) | quench time (s) | Catalyst Activity (g/mmol · hr) |
|---|---|---|---|---|---|---|---|---|---|
| EO-1 | 1* | B | 0.030 | 1.1 | 75 | 20 | 0.0366 | 365 | 14,435 |
| EO-2 | 1* | B | 0.030 | 1.1 | 75 | 20 | 0.0329 | 273 | 17,386 |
| EO-3 | 1* | B | 0.030 | 1.1 | 75 | 20 | 0.0344 | 276 | 17,961 |
| EO-4 | 1* | B | 0.030 | 1.1 | 200 | 15 | 0.0814 | 97 | 121,091 |
| EO-5 | 1* | B | 0.030 | 1.1 | 200 | 15 | 0.0759 | 106 | 103,304 |
| EO-6 | 1 | A | 0.030 | 500 | 75 | 20 | 0.0387 | 144 | 38,593 |
| EO-7 | 1 | A | 0.030 | 500 | 75 | 20 | 0.0437 | 85 | 73,773 |
| EO-8 | 1 | A | 0.030 | 500 | 75 | 20 | 0.0494 | 96 | 73,793 |
| EO-9 | 1 | A | 0.030 | 500 | 200 | 15 | 0.1162 | 88 | 189,930 |
| EO-10 | 1 | A | 0.030 | 500 | 200 | 15 | 0.1343 | 175 | 110,258 |
| EO-11 | 1 | A | 0.030 | 500 | 200 | 15 | 0.1318 | 184 | 103,260 |
| EO-12 | 2 | B | 0.025 | 1.1 | 75 | 20 | 0.1239 | 46 | 388,706 |
| EO-13 | 2 | B | 0.025 | 1.1 | 75 | 20 | 0.1185 | 42 | 408,230 |
| EO-14 | 2 | B | 0.025 | 1.1 | 75 | 20 | 0.1209 | 44 | 394,776 |
| EO-15 | 2 | B | 0.025 | 1.1 | 200 | 15 | 0.1988 | 54 | 528,177 |
| EO-16 | 2 | B | 0.025 | 1.1 | 200 | 15 | 0.1946 | 56 | 502,194 |
| EO-17 | 2 | B | 0.025 | 1.1 | 200 | 15 | 0.1854 | 26 | 1,011,273 |
| EO-18 | 2 | A | 0.025 | 500 | 75 | 20 | 0.1286 | 50 | 369,629 |
| EO-19 | 2 | A | 0.025 | 500 | 75 | 20 | 0.1282 | 53 | 347,008 |
| EO-20 | 2 | A | 0.025 | 500 | 75 | 20 | 0.1351 | 53 | 369,154 |
| EO-21 | 2 | A | 0.020 | 500 | 75 | 20 | 0.1137 | 56 | 362,872 |
| EO-22 | 2 | A | 0.020 | 500 | 75 | 20 | 0.1112 | 55 | 362,609 |
| EO-23 | 2 | A | 0.020 | 500 | 75 | 20 | 0.1163 | 56 | 376,511 |
| EO-24 | 2 | A | 0.025 | 500 | 200 | 15 | 0.2203 | 42 | 751,735 |
| EO-25 | 2 | A | 0.025 | 500 | 200 | 15 | 0.2148 | 50 | 619,864 |
| EO-26 | 2 | A | 0.025 | 500 | 200 | 15 | 0.2082 | 50 | 602,024 |
| EO-27 | 2 | A | 0.020 | 500 | 200 | 15 | 0.208 | 61 | 615,789 |
| EO-28 | 2 | A | 0.020 | 500 | 200 | 15 | 0.2071 | 82 | 457,399 |
| EO-29 | 2 | A | 0.020 | 500 | 200 | 15 | 0.2089 | 71 | 530,353 |
| EO-30 | 3* | B | 0.030 | 1.1 | 75 | 20 | 0.0981 | 52 | 269,588 |
| EO-31 | 3* | B | 0.030 | 1.1 | 75 | 20 | 0.0995 | 55 | 259,096 |
| EO-32 | 3* | B | 0.030 | 1.1 | 75 | 20 | 0.1013 | 58 | 251,503 |
| EO-33 | 3* | B | 0.030 | 1.1 | 200 | 15 | 0.1699 | 119 | 205,593 |
| EO-34 | 3* | B | 0.030 | 1.1 | 200 | 15 | 0.1968 | 112 | 252,578 |
| EO-35 | 3* | B | 0.030 | 1.1 | 200 | 15 | 0.1658 | 122 | 195,059 |
| EO-36 | 3 | A | 0.030 | 500 | 75 | 20 | 0.131 | 56 | 335,062 |
| EO-37 | 3 | A | 0.030 | 500 | 75 | 20 | 0.1286 | 51 | 360,280 |
| EO-38 | 3 | A | 0.030 | 500 | 75 | 20 | 0.1259 | 51 | 357,586 |
| EO-39 | 3 | A | 0.020 | 500 | 75 | 20 | 0.1062 | 49 | 391,721 |
| EO-40 | 3 | A | 0.020 | 500 | 75 | 20 | 0.1094 | 53 | 373,662 |
| EO-41 | 3 | A | 0.020 | 500 | 75 | 20 | 0.1134 | 54 | 376,605 |
| EO-42 | 3 | A | 0.030 | 500 | 200 | 15 | 0.2166 | 59 | 526,865 |
| EO-43 | 3 | A | 0.030 | 500 | 200 | 15 | 0.2074 | 51 | 582,175 |
| EO-44 | 3 | A | 0.030 | 500 | 200 | 15 | 0.2171 | 53 | 593,214 |
| EO-45 | 3 | A | 0.020 | 500 | 200 | 15 | 0.2061 | 69 | 538,433 |
| EO-46 | 3 | A | 0.020 | 500 | 200 | 15 | 0.2034 | 62 | 593,387 |
| EO-47 | 3 | A | 0.020 | 500 | 200 | 15 | 0.2022 | 61 | 594,706 |
| EO-48 | 4* | B | 0.030 | 1.1 | 75 | 20 | 0.0719 | 66 | 158,070 |
| EO-49 | 4* | B | 0.030 | 1.1 | 75 | 20 | 0.0697 | 73 | 138,058 |
| EO-50 | 4* | B | 0.030 | 1.1 | 75 | 20 | 0.0723 | 69 | 150,017 |
| EO-51 | 4* | B | 0.030 | 1.1 | 200 | 15 | 0.1802 | 81 | 320,356 |
| EO-52 | 4* | B | 0.030 | 1.1 | 200 | 15 | 0.1743 | 73 | 345,243 |

TABLE 2a-continued

Ethylene-Octene copolymerization examples - Part 1

| Ex # | Cat ID | Act ID | Cat (μmol) | Act/Cat (molar) | C2⁼ (psig) | Quench value (psi) | yield (g) | quench time (s) | Catalyst Activity (g/mmol · hr) |
|---|---|---|---|---|---|---|---|---|---|
| EO-53 | 4* | B | 0.030 | 1.1 | 200 | 15 | 0.1731 | 84 | 297,451 |
| EO-54 | 4 | A | 0.030 | 500 | 75 | 20 | 0.1231 | 43 | 412,242 |
| EO-55 | 4 | A | 0.030 | 500 | 75 | 20 | 0.1216 | 44 | 396,163 |
| EO-56 | 4 | A | 0.030 | 500 | 75 | 20 | 0.1247 | 43 | 418,573 |
| EO-57 | 4 | A | 0.020 | 500 | 75 | 20 | 0.1062 | 44 | 430,541 |
| EO-58 | 4 | A | 0.020 | 500 | 75 | 20 | 0.101 | 50 | 366,532 |
| EO-59 | 4 | A | 0.020 | 500 | 75 | 20 | 0.1048 | 43 | 435,658 |
| EO-60 | 4 | A | 0.030 | 500 | 200 | 15 | 0.2089 | 58 | 518,648 |
| EO-61 | 4 | A | 0.030 | 500 | 200 | 15 | 0.1924 | 67 | 412,900 |
| EO-62 | 4 | A | 0.030 | 500 | 200 | 15 | 0.2052 | 56 | 532,411 |
| EO-63 | 4 | A | 0.020 | 500 | 200 | 15 | 0.1985 | 77 | 462,824 |
| EO-64 | 4 | A | 0.020 | 500 | 200 | 15 | 0.1709 | 83 | 371,522 |
| EO-65 | 4 | A | 0.020 | 500 | 200 | 15 | 0.2001 | 82 | 437,112 |
| EO-66 | 5* | B | 0.030 | 1.1 | 75 | 20 | 0.0987 | 48 | 295,484 |
| EO-67 | 5* | B | 0.030 | 1.1 | 75 | 20 | 0.0949 | 42 | 324,599 |
| EO-68 | 5* | B | 0.030 | 1.1 | 75 | 20 | 0.095 | 46 | 296,746 |
| EO-69 | 5* | B | 0.030 | 1.1 | 200 | 15 | 0.1763 | 43 | 590,400 |
| EO-70 | 5* | B | 0.030 | 1.1 | 200 | 15 | 0.177 | 37 | 685,161 |
| EO-71 | 5* | B | 0.030 | 1.1 | 200 | 15 | 0.099 | 32 | 441,362 |
| EO-72 | 5 | A | 0.030 | 500 | 75 | 20 | 0.1064 | 42 | 366,545 |
| EO-73 | 5 | A | 0.030 | 500 | 75 | 20 | 0.1045 | 39 | 390,756 |
| EO-74 | 5 | A | 0.030 | 500 | 75 | 20 | 0.1073 | 38 | 403,426 |
| EO-75 | 5 | A | 0.020 | 500 | 75 | 20 | 0.0892 | 46 | 347,532 |
| EO-76 | 5 | A | 0.020 | 500 | 75 | 20 | 0.0718 | 67 | 194,054 |
| EO-77 | 5 | A | 0.020 | 500 | 75 | 20 | 0.0873 | 46 | 343,851 |
| EO-78 | 5 | A | 0.030 | 500 | 200 | 15 | 0.1974 | 89 | 320,469 |
| EO-79 | 5 | A | 0.030 | 500 | 200 | 15 | 0.1962 | 89 | 319,241 |
| EO-80 | 5 | A | 0.030 | 500 | 200 | 15 | 0.1905 | 81 | 337,002 |
| EO-81 | 5 | A | 0.020 | 500 | 200 | 15 | 0.1434 | 50 | 518,313 |
| EO-82 | 5 | A | 0.020 | 500 | 200 | 15 | 0.1228 | 48 | 460,500 |
| EO-83 | 5 | A | 0.020 | 500 | 200 | 15 | 0.1798 | 77 | 421,406 |
| EO-84 | 6* | B | 0.030 | 1.1 | 75 | 20 | 0.1693 | 1801 | 13,534 |
| EO-85 | 6* | B | 0.030 | 1.1 | 75 | 20 | 0.0645 | 309 | 30,058 |
| EO-86 | 6* | B | 0.030 | 1.1 | 75 | 20 | 0.0572 | 284 | 28,993 |
| EO-87 | 6* | B | 0.030 | 1.1 | 200 | 15 | 0.0986 | 154 | 92,018 |
| EO-88 | 6* | B | 0.030 | 1.1 | 200 | 15 | 0.1048 | 165 | 91,406 |
| EO-89 | 6* | B | 0.030 | 1.1 | 200 | 15 | 0.0691 | 167 | 59,690 |
| EO-90 | 6 | A | 0.030 | 500 | 75 | 20 | 0.0737 | 96 | 111,129 |
| EO-91 | 6 | A | 0.030 | 500 | 75 | 20 | 0.0762 | 108 | 101,506 |
| EO-92 | 6 | A | 0.030 | 500 | 75 | 20 | 0.0841 | 103 | 117,235 |
| EO-93 | 6 | A | 0.020 | 500 | 75 | 20 | 0.0597 | 200 | 53,650 |
| EO-94 | 6 | A | 0.020 | 500 | 75 | 20 | 0.0516 | 203 | 45,686 |
| EO-95 | 6 | A | 0.020 | 500 | 75 | 20 | 0.0583 | 217 | 48,270 |
| EO-96 | 6 | A | 0.030 | 500 | 200 | 15 | 0.1729 | 59 | 419,152 |
| EO-97 | 6 | A | 0.030 | 500 | 200 | 15 | 0.1746 | 62 | 402,923 |
| EO-98 | 6 | A | 0.030 | 500 | 200 | 15 | 0.1664 | 67 | 358,707 |
| EO-99 | 6 | A | 0.020 | 500 | 200 | 15 | 0.1144 | 96 | 214,277 |
| EO-100 | 6 | A | 0.020 | 500 | 200 | 15 | 0.0993 | 104 | 171,371 |
| EO-101 | 6 | A | 0.020 | 500 | 200 | 15 | 0.1146 | 96 | 215,549 |
| EO-102 | 7a | A | 0.030 | 500 | 75 | 20 | 0.1053 | 47 | 324,694 |
| EO-103 | 7a | A | 0.030 | 500 | 75 | 20 | 0.1031 | 44 | 335,891 |
| EO-104 | 7a | A | 0.030 | 500 | 75 | 20 | 0.1092 | 46 | 338,897 |
| EO-105 | 7a | A | 0.020 | 500 | 75 | 20 | 0.0908 | 63 | 261,504 |
| EO-106 | 7a | A | 0.020 | 500 | 75 | 20 | 0.0871 | 57 | 276,508 |
| EO-107 | 7a | A | 0.030 | 500 | 200 | 15 | 0.2383 | 93 | 370,175 |
| EO-108 | 7a | A | 0.030 | 500 | 200 | 15 | 0.2041 | 95 | 309,699 |
| EO-109 | 7a | A | 0.030 | 500 | 200 | 15 | 0.1779 | 102 | 250,416 |
| EO-110 | 7a | A | 0.020 | 500 | 200 | 15 | 0.2222 | 86 | 463,991 |
| EO-111 | 7a | A | 0.020 | 500 | 200 | 15 | 0.1882 | 87 | 388,932 |
| EO-112 | 7a | A | 0.020 | 500 | 200 | 15 | 0.1856 | 81 | 413,978 |
| EO-113 | 7b | A | 0.030 | 500 | 75 | 20 | 0.1275 | 46 | 399,130 |
| EO-114 | 7b | A | 0.030 | 500 | 75 | 20 | 0.1283 | 43 | 427,667 |
| EO-115 | 7b | A | 0.020 | 500 | 75 | 20 | 0.1143 | 54 | 380,296 |
| EO-116 | 7b | A | 0.020 | 500 | 75 | 20 | 0.1044 | 48 | 390,686 |
| EO-117 | 7b | A | 0.020 | 500 | 75 | 20 | 0.1122 | 51 | 398,343 |
| EO-118 | 7b | A | 0.030 | 500 | 200 | 15 | 0.2128 | 48 | 637,073 |
| EO-119 | 7b | A | 0.030 | 500 | 200 | 15 | 0.215 | 53 | 587,476 |
| EO-120 | 7b | A | 0.030 | 500 | 200 | 15 | 0.2134 | 58 | 534,428 |
| EO-121 | 7b | A | 0.020 | 500 | 200 | 15 | 0.202 | 65 | 556,815 |
| EO-122 | 7b | A | 0.020 | 500 | 200 | 15 | 0.197 | 58 | 615,625 |
| EO-123 | 7b | A | 0.020 | 500 | 200 | 15 | 0.194 | 60 | 586,891 |
| EO-124 | 8* | B | 0.030 | 1.1 | 75 | 20 | 0.0822 | 57 | 209,131 |
| EO-125 | 8* | B | 0.030 | 1.1 | 75 | 20 | 0.0777 | 56 | 200,157 |
| EO-126 | 8* | B | 0.030 | 1.1 | 200 | 15 | 0.0337 | 64 | 76,182 |

TABLE 2a-continued

Ethylene-Octene copolymerization examples - Part 1

| Ex # | Cat ID | Act ID | Cat (μmol) | Act/Cat (molar) | C2⁼ (psig) | Quench value (psi) | yield (g) | quench time (s) | Catalyst Activity (g/mmol · hr) |
|---|---|---|---|---|---|---|---|---|---|
| EO-127 | 8* | B | 0.030 | 1.1 | 200 | 15 | 0.1645 | 161 | 146,766 |
| EO-128 | 8* | B | 0.030 | 1.1 | 200 | 15 | 0.1647 | 39 | 616,021 |
| EO-129 | 8 | A | 0.030 | 500 | 75 | 20 | 0.0728 | 58 | 181,057 |
| EO-130 | 8 | A | 0.030 | 500 | 75 | 20 | 0.0701 | 56 | 179,616 |
| EO-131 | 8 | A | 0.030 | 500 | 75 | 20 | 0.07 | 55 | 183,607 |
| EO-132 | 8 | A | 0.030 | 500 | 200 | 15 | 0.1626 | 137 | 170,535 |
| EO-133 | 8 | A | 0.030 | 500 | 200 | 15 | 0.1745 | 125 | 200,863 |
| EO-134 | 8 | A | 0.030 | 500 | 200 | 15 | 0.1385 | 41 | 487,628 |
| EO-135 | 9* | B | 0.030 | 1.1 | 75 | 20 | 0.0876 | 55 | 230,611 |
| EO-136 | 9* | B | 0.030 | 1.1 | 75 | 20 | 0.0889 | 52 | 245,241 |
| EO-137 | 9* | B | 0.030 | 1.1 | 75 | 20 | 0.0898 | 52 | 250,120 |
| EO-138 | 9* | B | 0.030 | 1.1 | 200 | 15 | 0.1787 | 85 | 304,530 |
| EO-139 | 9* | B | 0.030 | 1.1 | 200 | 15 | 0.1772 | 85 | 301,617 |
| EO-140 | 9* | B | 0.030 | 1.1 | 200 | 15 | 0.1701 | 71 | 343,540 |
| EO-141 | 9 | A | 0.030 | 500 | 75 | 20 | 0.1064 | 53 | 289,087 |
| EO-142 | 9 | A | 0.030 | 500 | 75 | 20 | 0.1059 | 56 | 271,345 |
| EO-143 | 9 | A | 0.030 | 500 | 75 | 20 | 0.112 | 60 | 270,604 |
| EO-144 | 9 | A | 0.030 | 500 | 200 | 15 | 0.1949 | 43 | 652,688 |
| EO-145 | 9 | A | 0.030 | 500 | 200 | 15 | 0.1577 | 35 | 654,432 |
| EO-146 | 9 | A | 0.030 | 500 | 200 | 15 | 0.1822 | 50 | 521,606 |
| EO-147 | 10* | B | 0.025 | 1.1 | 75 | 20 | 0.1073 | 172 | 89,885 |
| EO-148 | 10* | B | 0.025 | 1.1 | 75 | 20 | 0.0995 | 166 | 86,209 |
| EO-149 | 10* | B | 0.025 | 1.1 | 75 | 20 | 0.106 | 118 | 129,028 |
| EO-150 | 10* | B | 0.025 | 1.1 | 200 | 15 | 0.1695 | 129 | 188,770 |
| EO-151 | 10* | B | 0.025 | 1.1 | 200 | 15 | 0.1811 | 99 | 262,358 |
| EO-152 | 10* | B | 0.025 | 1.1 | 200 | 15 | 0.18 | 108 | 240,669 |
| EO-153 | 10 | A | 0.030 | 500 | 75 | 20 | 0.0687 | 113 | 87,780 |
| EO-154 | 10 | A | 0.030 | 500 | 75 | 20 | 0.0651 | 130 | 72,166 |
| EO-155 | 10 | A | 0.030 | 500 | 75 | 20 | 0.0668 | 128 | 75,033 |
| EO-156 | 10 | A | 0.030 | 500 | 200 | 15 | 0.1667 | 153 | 156,485 |
| EO-157 | 10 | A | 0.030 | 500 | 200 | 15 | 0.1728 | 145 | 171,727 |
| EO-158 | 10 | A | 0.030 | 500 | 200 | 15 | 0.1662 | 133 | 179,946 |
| EO-159 | 11* | B | 0.030 | 1.1 | 75 | 20 | 0.0485 | 1553 | 4,498 |
| EO-160 | 11* | B | 0.030 | 1.1 | 75 | 20 | 0.0481 | 1173 | 5,903 |
| EO-161 | 11* | B | 0.030 | 1.1 | 75 | 20 | 0.0426 | 1617 | 3,794 |
| EO-162 | 11* | B | 0.030 | 1.1 | 200 | 15 | 0.0684 | 294 | 33,468 |
| EO-163 | 11* | B | 0.030 | 1.1 | 200 | 15 | 0.0799 | 295 | 39,002 |
| EO-164 | 11* | B | 0.030 | 1.1 | 200 | 15 | 0.0685 | 379 | 26,020 |
| EO-165 | 11 | A | 0.030 | 500 | 75 | 20 | 0.049 | 147 | 47,964 |
| EO-166 | 11 | A | 0.030 | 500 | 75 | 20 | 0.0612 | 129 | 68,369 |
| EO-167 | 11 | A | 0.030 | 500 | 75 | 20 | 0.0556 | 141 | 56,622 |
| EO-168 | 11 | A | 0.030 | 500 | 200 | 15 | 0.1531 | 144 | 153,100 |
| EO-169 | 11 | A | 0.030 | 500 | 200 | 15 | 0.1359 | 181 | 108,239 |
| EO-170 | 11 | A | 0.030 | 500 | 200 | 15 | 0.1444 | 157 | 132,443 |
| EO-171 | 12* | B | 0.030 | 1.1 | 75 | 20 | 0.0258 | 518 | 7,167 |
| EO-172 | 12* | B | 0.030 | 1.1 | 75 | 20 | 0.0249 | 589 | 6,093 |
| EO-173 | 12* | B | 0.030 | 1.1 | 75 | 20 | 0.1489 | 1800 | 11,912 |
| EO-174 | 12* | B | 0.030 | 1.1 | 200 | 15 | 0.0222 | 405 | 7,895 |
| EO-175 | 12* | B | 0.030 | 1.1 | 200 | 15 | 0.0373 | 493 | 10,906 |
| EO-176 | 12* | B | 0.030 | 1.1 | 200 | 15 | 0.0206 | 471 | 6,305 |
| EO-177 | 12 | A | 0.030 | 500 | 75 | 20 | 0.0304 | 1708 | 2,563 |
| EO-178 | 12 | A | 0.030 | 500 | 75 | 20 | 0.0313 | 1663 | 2,711 |
| EO-179 | 12 | A | 0.030 | 500 | 200 | 15 | 0.0443 | 470 | 13,564 |
| EO-180 | 12 | A | 0.030 | 500 | 200 | 15 | 0.0481 | 490 | 14,136 |
| EO-181 | 12 | A | 0.030 | 500 | 200 | 15 | 0.0502 | 511 | 14,155 |
| C-10 | CB | A | 0.030 | 500 | 75 | 20 | 0.1016 | 54 | 269,436 |
| C-11 | CB | A | 0.030 | 500 | 75 | 20 | 0.1039 | 61 | 246,079 |
| C-12 | CB | A | 0.030 | 500 | 75 | 20 | 0.1067 | 54 | 282,441 |
| C-13 | CB | A | 0.030 | 500 | 200 | 15 | 0.1951 | 47 | 595,220 |
| C-14 | CB | A | 0.030 | 500 | 200 | 15 | 0.1836 | 36 | 726,330 |
| C-15 | CB | A | 0.030 | 500 | 200 | 15 | 0.1926 | 46 | 600,312 |
| C-16 | CC* | B | 0.025 | 1.1 | 75 | 20 | 0.101 | 210 | 69,422 |
| C-17 | CC* | B | 0.025 | 1.1 | 75 | 20 | 0.0636 | 134 | 68,551 |
| C-18 | CC* | B | 0.025 | 1.1 | 75 | 20 | 0.0861 | 142 | 87,067 |
| C-19 | CC* | B | 0.025 | 1.1 | 200 | 15 | 0.1817 | 139 | 188,643 |
| C-20 | CC* | B | 0.025 | 1.1 | 200 | 15 | 0.1779 | 133 | 192,180 |
| C-21 | CC* | B | 0.025 | 1.1 | 200 | 15 | 0.1802 | 142 | 182,609 |
| C-22 | CC | A | 0.030 | 500 | 75 | 20 | 0.0621 | 138 | 64,613 |
| C-23 | CC | A | 0.030 | 500 | 75 | 20 | 0.0583 | 136 | 61,684 |
| C-24 | CC | A | 0.030 | 500 | 75 | 20 | 0.0572 | 129 | 64,050 |
| C-25 | CC | A | 0.030 | 500 | 200 | 15 | 0.1471 | 141 | 150,017 |
| C-26 | CC | A | 0.030 | 500 | 200 | 15 | 0.1675 | 143 | 169,144 |
| C-27 | CC | A | 0.030 | 500 | 200 | 15 | 0.169 | 147 | 165,890 |

For all runs, the total amount of toluene added to the reactor was 4.9 ml, 100 ul of 1-octene was added, and the ethylene pressure was maintained at 75 psig or 200 psig of ethylene as indicated.

TABLE 2b

Ethylene-Octene copolymerization examples - Part 2

| Ex# | Cat ID | Act ID | Mn | Mw | Mw/Mn | C8 wt % | $T_m$ (° C.) |
|---|---|---|---|---|---|---|---|
| EO-1 | 1* | B | 28,282 | 102,163 | 3.61 | 5.1 | 123.1 |
| EO-2 | 1* | B | 60,402 | 296,676 | 4.91 | 4.4 | 124.2 |
| EO-3 | 1* | B | 50,832 | 239,028 | 4.7 | 3.8** | 124.0 |
| EO-4 | 1* | B | 142,743 | 539,956 | 3.78 | 2.4** | 127.7 |
| EO-5 | 1* | B | 183,795 | 641,482 | 3.49 | 2.1** | 127.8 |
| EO-6 | 1 | A | 26,987 | 194,194 | 7.2 | 5.4 | 126.7 |
| EO-7 | 1 | A | 46,178 | 366,345 | 7.93 | 4.6 | 124.8 |
| EO-8 | 1 | A | 36,892 | 394,178 | 10.68 | 4.7 | 125.5 |
| EO-9 | 1 | A | 111,264 | 701,045 | 6.3 | 2.7** | 128.0 |
| EO-10 | 1 | A | 80,912 | 584,483 | 7.22 | 3.2** | 129.1 |
| EO-11 | 1 | A | 113,935 | 681,394 | 5.98 | 3.0** | 128.9 |
| EO-12 | 2 | B | 122,718 | 232,963 | 1.90 | 30.5 | 91.0 |
| EO-13 | 2 | B | 143,297 | 253,080 | 1.77 | 32.1 | 90.9 |
| EO-14 | 2 | B | 118,965 | 212,318 | 1.78 | 31.7 | 90.5 |
| EO-15 | 2 | B | 186,220 | 401,284 | 2.15 | 14.1 | 109.1 |
| EO-16 | 2 | B | 215,331 | 446,599 | 2.07 | 17.9 | 108.9 |
| EO-17 | 2 | B | 207,458 | 409,241 | 1.97 | 14.5 | 109.6 |
| EO-18 | 2 | A | 129,908 | 276,356 | 2.13 | 30.4 | 88.5 |
| EO-19 | 2 | A | 149,148 | 315,580 | 2.12 | 31.9 | 90.2 |
| EO-20 | 2 | A | 121,546 | 269,266 | 2.22 | 35.3 | 87.2 |
| EO-21 | 2 | A | 201,364 | 333,364 | 1.66 | 29.7 | 85.2 |
| EO-22 | 2 | A | 154,543 | 258,128 | 1.67 | 29.6 | 87.8 |
| EO-23 | 2 | A | 217,002 | 357,012 | 1.65 | 27.5 | 86.5 |
| EO-24 | 2 | A | 73,844 | 358,447 | 4.85 | 21.7 | 106.6 |
| EO-25 | 2 | A | 102,402 | 348,245 | 3.40 | 22.9 | 104.6 |
| EO-26 | 2 | A | 172,920 | 436,569 | 2.52 | 20.0 | 109.2 |
| EO-27 | 2 | A | 165,328 | 450,967 | 2.73 | 16.7 | 107.4 |
| EO-28 | 2 | A | 133,205 | 390,530 | 2.93 | 19.1 | 104.8 |
| EO-29 | 2 | A | 139,995 | 412,082 | 2.94 | 19.3 | 105.9 |
| EO-30 | 3* | B | 212,086 | 335,082 | 1.58 | 24.5 | 87.4 |
| EO-31 | 3* | B | 216,320 | 337,422 | 1.56 | 24.8 | 87.7 |
| EO-32 | 3* | B | 206,669 | 329,670 | 1.6 | 29.7 | 87.9 |
| EO-33 | 3* | B | 181,222 | 367,160 | 2.03 | 19.5 | 106.8 |
| EO-34 | 3* | B | 229,565 | 413,970 | 1.8 | 15.6 | 108.5 |
| EO-35 | 3* | B | 207,251 | 390,765 | 1.89 | 17.6 | 108.5 |
| EO-36 | 3 | A | 135,518 | 310,786 | 2.29 | 30.8 | 93.3 |
| EO-37 | 3 | A | 142,708 | 303,204 | 2.12 | 32.5 | 90.3 |
| EO-38 | 3 | A | 138,581 | 311,049 | 2.24 | 32.9 | 90.9 |
| EO-39 | 3 | A | 202,123 | 331,653 | 1.64 | 28.3 | 88.5 |
| EO-40 | 3 | A | 207,178 | 328,872 | 1.59 | 27.9 | 85.7 |
| EO-41 | 3 | A | 171,274 | 291,700 | 1.7 | 30.7 | 90.0 |
| EO-42 | 3 | A | 100,373 | 336,197 | 3.35 | 21.2 | 102.6 |
| EO-43 | 3 | A | 117,913 | 431,127 | 3.66 | 15.6 | 110.1 |
| EO-44 | 3 | A | 190,889 | 469,091 | 2.46 | 12.8 | 110.4 |
| EO-45 | 3 | A | 136,944 | 489,739 | 3.58 | 18.9 | 108.6 |
| EO-46 | 3 | A | 163,176 | 506,020 | 3.1 | 18.5 | 110.2 |
| EO-47 | 3 | A | 153,724 | 433,466 | 2.82 | 18.4 | 107.2 |
| EO-48 | 4* | B | 223,982 | 330,914 | 1.48 | 21.0 | 88.2 |
| EO-49 | 4* | B | 234,021 | 346,049 | 1.48 | 21.5 | 90.0 |
| EO-50 | 4* | B | 230,352 | 341,306 | 1.48 | 19.6 | 89.1 |
| EO-51 | 4* | B | 222,927 | 358,385 | 1.61 | 10.5 | 108.6 |
| EO-52 | 4* | B | 210,794 | 348,124 | 1.65 | 13.2 | 107.4 |
| EO-53 | 4* | B | 182,051 | 326,443 | 1.79 | 15.7 | 107.9 |
| EO-54 | 4 | A | 115,351 | 234,520 | 2.03 | 31.0 | 90.1 |
| EO-55 | 4 | A | 111,143 | 241,882 | 2.18 | 28.6 | 91.9 |
| EO-56 | 4 | A | 109,502 | 235,180 | 2.15 | 32.2 | 90.6 |
| EO-57 | 4 | A | 166,221 | 257,643 | 1.55 | 25.0 | 86.0 |
| EO-58 | 4 | A | 176,837 | 273,670 | 1.55 | 26.4 | 86.4 |
| EO-59 | 4 | A | 175,524 | 267,364 | 1.52 | 24.7 | 85.8 |
| EO-60 | 4 | A | 117,780 | 311,122 | 2.64 | 18.5 | 105.7 |
| EO-61 | 4 | A | 96,811 | 291,842 | 3.01 | 18.9 | 108.4 |
| EO-62 | 4 | A | 115,349 | 331,367 | 2.87 | 17.0 | 110.2 |
| EO-63 | 4 | A | 175,974 | 405,456 | 2.3 | 16.3 | 109.7 |
| EO-64 | 4 | A | 268,379 | 419,935 | 1.56 | 15.1 | 107.2 |
| EO-65 | 4 | A | 190,280 | 373,196 | 1.96 | 15.2 | 108.5 |
| EO-66 | 5* | B | 152,169 | 241,372 | 1.59 | 17.1 | 100.8 |
| EO-67 | 5* | B | 131,277 | 241,099 | 1.84 | 17.5 | 101.4 |
| EO-68 | 5* | B | 156,066 | 234,394 | 1.5 | 18.2 | 100.4 |
| EO-69 | 5* | B | 154,395 | 252,572 | 1.64 | 9.4 | 114.9 |
| EO-70 | 5* | B | 151,531 | 243,136 | 1.6 | 9.4 | 115.9 |
| EO-71 | 5* | B | 173,025 | 260,631 | 1.51 | 13.6 | 104.7 |
| EO-72 | 5 | A | 126,163 | 245,636 | 1.95 | 20.7 | 97.9 |
| EO-73 | 5 | A | 125,912 | 248,147 | 1.97 | 21.8 | 102.0 |
| EO-74 | 5 | A | 130,545 | 251,485 | 1.93 | 21.1 | 100.7 |
| EO-75 | 5 | A | 181,296 | 267,943 | 1.48 | 15.4 | 96.0 |
| EO-76 | 5 | A | 198,530 | 282,727 | 1.42 | 16.2 | 99.0 |
| EO-77 | 5 | A | na | na | na | na | na |
| EO-78 | 5 | A | 143,661 | 303,141 | 2.11 | 11.5 | 114.2 |
| EO-79 | 5 | A | 142,509 | 305,020 | 2.14 | 11.9 | 114.5 |
| EO-80 | 5 | A | 148,109 | 317,634 | 2.14 | 12.7 | 115.8 |
| EO-81 | 5 | A | 208,332 | 302,848 | 1.45 | 6.6 | 114.3 |
| EO-82 | 5 | A | 211,994 | 305,510 | 1.44 | 6.9 | 114.6 |
| EO-83 | 5 | A | 196,541 | 296,832 | 1.51 | 9.4 | 113.5 |
| EO-84 | 6* | B | 98,145 | 218,127 | 2.22 | 19.4 | 101.8 |
| EO-85 | 6* | B | 147,934 | 252,794 | 1.71 | 21.1 | 89.7 |
| EO-86 | 6* | B | 149,258 | 251,129 | 1.68 | 21.6 | 87.7 |
| EO-87 | 6* | B | 180,178 | 288,782 | 1.6 | 11.2 | 106.5 |
| EO-88 | 6* | B | 176,297 | 288,891 | 1.64 | 13.3 | 104.7 |
| EO-89 | 6* | B | 176,961 | 281,069 | 1.59 | 9.9 | 107.3 |
| EO-90 | 6 | A | 49,343 | 178,242 | 3.61 | 20.6 | 98.9 |
| EO-91 | 6 | A | 51,932 | 176,464 | 3.4 | 23.2 | 84.5 |
| EO-92 | 6 | A | 52,351 | 176,007 | 3.36 | 20.7 | 97.9 |
| EO-93 | 6 | A | 79,280 | 176,839 | 2.23 | 22.0 | 100.7 |
| EO-94 | 6 | A | 81,060 | 176,837 | 2.18 | 23.6 | 100.1 |
| EO-95 | 6 | A | 79,188 | 173,579 | 2.19 | 23.2 | 97.9 |
| EO-96 | 6 | A | 75,747 | 231,119 | 3.05 | 13.6 | 105.8 |
| EO-97 | 6 | A | 82,708 | 224,294 | 2.71 | 13.4 | 105.9 |
| EO-98 | 6 | A | 91,408 | 224,141 | 2.45 | 13.2 | 105.9 |
| EO-99 | 6 | A | 146,993 | 248,292 | 1.69 | 12.9 | 105.4 |
| EO-100 | 6 | A | 155,249 | 252,651 | 1.63 | 10.9 | 105.4 |
| EO-101 | 6 | A | 159,231 | 258,488 | 1.62 | 12.6 | 104.4 |
| EO-102 | 7a | A | 109,316 | 246,915 | 2.26 | 23.9 | 95.7 |
| EO-103 | 7a | A | 101,242 | 227,106 | 2.24 | 24.7 | 92.5 |
| EO-104 | 7a | A | 95,062 | 342,778 | 3.61 | 23.3 | 97.0 |
| EO-105 | 7a | A | 143,802 | 244,932 | 1.7 | 21.6 | 91.6 |
| EO-106 | 7a | A | 156,334 | 254,284 | 1.63 | 22.5 | 89.8 |
| EO-107 | 7a | A | 103,940 | 328,621 | 3.16 | 16.9 | 109.3 |
| EO-108 | 7a | A | 95,788 | 299,762 | 3.13 | 17.2 | 108.1 |
| EO-109 | 7a | A | 70,742 | 352,170 | 4.98 | 20.3 | 109.2 |
| EO-110 | 7a | A | 122,644 | 280,074 | 2.28 | 18.5 | 106.9 |
| EO-111 | 7a | A | 204,875 | 353,806 | 1.73 | 15.6 | 107.1 |
| EO-112 | 7a | A | 171,855 | 334,803 | 1.95 | 11.7 | 107.2 |
| EO-113 | 7b | A | 140,145 | 329,098 | 2.35 | 29.6 | 76.5 |
| EO-114 | 7b | A | 127,614 | 290,113 | 2.27 | 33.3 | 90.6 |
| EO-115 | 7b | A | 182,556 | 296,007 | 1.62 | 27.7 | 86.6 |
| EO-116 | 7b | A | 200,031 | 315,313 | 1.58 | 24.1 | 88.1 |
| EO-117 | 7b | A | 192,050 | 304,793 | 1.59 | 31.8 | 86.1 |
| EO-118 | 7b | A | 74,745 | 404,885 | 5.42 | 20.8 | 109.3 |
| EO-119 | 7b | A | 198,842 | 545,019 | 2.74 | 16.7 | 113.1 |
| EO-120 | 7b | A | 149,515 | 418,779 | 2.8 | 18.4 | 109.7 |
| EO-121 | 7b | A | 207,669 | 469,879 | 2.26 | 16.1 | 109.9 |
| EO-122 | 7b | A | 218,432 | 513,046 | 2.35 | 14.3 | 110.4 |
| EO-123 | 7b | A | 245,708 | 497,282 | 2.02 | 14.0 | 109.9 |
| EO-124 | 8* | B | 192,728 | 353,492 | 1.83 | 16.6 | 117.9 |
| EO-125 | 8* | B | 195,082 | 350,616 | 1.8 | 17.4 | 116.7 |
| EO-126 | 8* | B | 346,660 | 773,121 | 2.23 | 4.2 | 124.2 |
| EO-127 | 8* | B | 216,025 | 503,579 | 2.33 | 11.6 | 122.1 |
| EO-128 | 8* | B | 249,923 | 537,191 | 2.15 | 8.2 | 121.5 |
| EO-129 | 8 | A | 272,012 | 403,191 | 1.48 | 9.1 | 121.0 |
| EO-130 | 8 | A | 291,493 | 435,954 | 1.5 | 9.2 | 120.8 |
| EO-131 | 8 | A | 285,114 | 410,660 | 1.44 | 8.3 | 120.5 |
| EO-132 | 8 | A | 281,431 | 471,224 | 1.67 | 8.6 | 125.1 |
| EO-133 | 8 | A | 278,075 | 441,145 | 1.59 | 8.0 | 124.8 |
| EO-134 | 8 | A | 280,310 | 441,595 | 1.58 | 4.0** | 125.9 |
| EO-135 | 9* | B | 240,377 | 359,379 | 1.5 | 11.8 | 109.2 |
| EO-136 | 9* | B | 234,708 | 349,009 | 1.49 | 13.5 | 107.6 |
| EO-137 | 9* | B | 240,113 | 359,917 | 1.5 | 10.9 | 109.4 |
| EO-138 | 9* | B | 227,754 | 353,654 | 1.55 | 8.2 | 121.1 |
| EO-139 | 9* | B | 229,756 | 357,530 | 1.56 | 8.7 | 120.3 |
| EO-140 | 9* | B | 231,920 | 356,895 | 1.54 | 7.3 | 121.1 |
| EO-141 | 9 | A | 233,122 | 392,566 | 1.68 | 19.6 | 110.5 |
| EO-142 | 9 | A | 261,858 | 412,980 | 1.58 | 24.9 | 110.2 |
| EO-143 | 9 | A | 250,450 | 426,123 | 1.7 | 17.9 | 111.7 |
| EO-144 | 9 | A | 319,136 | 463,189 | 1.45 | 8.7 | 121.6 |

TABLE 2b-continued

Ethylene-Octene copolymerization examples - Part 2

| Ex# | Cat ID | Act ID | Mn | Mw | Mw/Mn | C8 wt % | T$_m$ (° C.) |
|---|---|---|---|---|---|---|---|
| EO-145 | 9 | A | 324,772 | 463,846 | 1.43 | 7.1 | 122.0 |
| EO-146 | 9 | A | 326,092 | 476,817 | 1.46 | 9.1 | 121.6 |
| EO-147 | 10* | B | 294,144 | 538,357 | 1.83 | 28.9 | 105.5 |
| EO-148 | 10* | B | 330,361 | 560,766 | 1.7 | 26.6 | 104.7 |
| EO-149 | 10* | B | 249,553 | 461,756 | 1.85 | 29.2 | 104.7 |
| EO-150 | 10* | B | 446,334 | 882,748 | 1.98 | 14.9 | 114.5 |
| EO-151 | 10* | B | 389,621 | 818,467 | 2.1 | 15.6 | 114.9 |
| EO-152 | 10* | B | 439,269 | 896,318 | 2.04 | 14.9 | 115.4 |
| EO-153 | 10 | A | 430,429 | 834,308 | 1.94 | 16.5 | 111.7 |
| EO-154 | 10 | A | 518,100 | 897,380 | 1.73 | 16.0 | 110.9 |
| EO-155 | 10 | A | 464,677 | 838,650 | 1.8 | 14.7 | 111.4 |
| EO-156 | 10 | A | 420,200 | 850,821 | 2.02 | 9.6 | 116.8 |
| EO-157 | 10 | A | 404,822 | 835,989 | 2.07 | 9.2 | 117.6 |
| EO-158 | 10 | A | 450,789 | 910,358 | 2.02 | 10.5 | 117.3 |
| EO-159 | 11* | B | 1,029,779 | 1,474,449 | 1.43 | 17.1 | 90.2 |
| EO-160 | 11* | B | 1,039,453 | 1,514,308 | 1.46 | 16.9 | 116.2 |
| EO-161 | 11* | B | 1,048,147 | 1,566,177 | 1.49 | 17.7 | 115.1 |
| EO-162 | 11* | B | 1,640,818 | 2,383,016 | 1.45 | 9.2 | 108.3 |
| EO-163 | 11* | B | 1,627,563 | 2,359,002 | 1.45 | 8.4 | 108.6 |
| EO-164 | 11* | B | 1,663,405 | 2,471,032 | 1.49 | 9.5 | 107.5 |
| EO-165 | 11 | A | 220,879 | 455,957 | 2.06 | 18.1 | 90.1 |
| EO-166 | 11 | A | 323,904 | 572,832 | 1.77 | 19.3 | 88.2 |
| EO-167 | 11 | A | 274,569 | 486,918 | 1.77 | 17.7 | 90.1 |
| EO-168 | 11 | A | 331,957 | 885,455 | 2.67 | 12.7 | 115.9 |
| EO-169 | 11 | A | 358,697 | 758,280 | 2.11 | 10.5 | 107.4 |
| EO-170 | 11 | A | 228,838 | 627,565 | 2.74 | 40.6** | 106.9 |
| EO-171 | 12* | B | 1,628 | 1,775 | 1.09 | 17.5 | 121.9 |
| EO-172 | 12* | B | 1,662 | 1,796 | 1.08 | 17.2 | 121.0 |
| EO-173 | 12* | B | 1,621 | 1,807 | 1.11 | 35.7 | 119.5 |
| EO-174 | 12* | B | 1,595 | 1,719 | 1.08 | 10.1 | 124.4 |
| EO-175 | 12* | B | 1,651 | 1,800 | 1.09 | 10.5 | 123.7 |
| EO-176 | 12* | B | 1,587 | 1,723 | 1.09 | 9.0 | 123.6 |
| EO-177 | 12 | A | 4,044 | 697,036 | 172.35 | 14.3 | 124.8 |
| EO-178 | 12 | A | 4,385 | 771,950 | 176.03 | 11.7 | 125.6 |
| EO-179 | 12 | A | 18,912 | 1,664,665 | 88.02 | 5.5 | 128.9 |
| EO-180 | 12 | A | 8,460 | 1,561,753 | 184.61 | 8.2 | 129.4 |
| EO-181 | 12 | A | 10,117 | 1,488,987 | 147.18 | 6.9 | 127.9 |
| C-10 | CB | A | 204,239 | 376,199 | 1.84 | 14.0 | 115.1 |
| C-11 | CB | A | 223,744 | 379,934 | 1.7 | 15.0 | 115.6 |
| C-12 | CB | A | 220,206 | 390,628 | 1.77 | 13.8 | 115.7 |
| C-13 | CB | A | 267,833 | 419,011 | 1.56 | 6.9 | 124.1 |
| C-14 | CB | A | 323,934 | 453,770 | 1.4 | 5.8 | 124.7 |
| C-15 | CB | A | 316,093 | 448,692 | 1.42 | 6.7 | 124.5 |
| C-16 | CC* | B | 333,264 | 546,078 | 1.64 | 24.6 | 110.0 |
| C-17 | CC* | B | 448,326 | 725,367 | 1.62 | 15.3 | 109.9 |
| C-18 | CC* | B | 402,885 | 647,137 | 1.61 | 19.8 | 109.2 |
| C-19 | CC* | B | 327,944 | 750,502 | 2.29 | 14.4 | 117.4 |
| C-20 | CC* | B | 351,576 | 773,003 | 2.2 | 15.0 | 116.9 |
| C-21 | CC* | B | 306,621 | 749,511 | 2.44 | 14.3 | 116.9 |
| C-22 | CC | A | 599,869 | 818,132 | 1.36 | 9.7 | 115.0 |
| C-23 | CC | A | 590,501 | 805,692 | 1.36 | 9.6 | 115.1 |
| C-24 | CC | A | 606,220 | 836,493 | 1.38 | 9.4 | 115.6 |
| C-25 | CC | A | 553,115 | 799,283 | 1.45 | 6.6 | 120.7 |
| C-26 | CC | A | 546,822 | 776,511 | 1.42 | 7.2 | 120.0 |
| C-27 | CC | A | 548,297 | 799,462 | 1.46 | 6.7 | 120.5 |

"na" indicates that the data was not available.
**Values outside of the calibration range

TABLE 3a

Propylene polymerization examples - Part 1

| Ex# | Cat ID | Act ID | Cat (µmol) | Act/Cat (molar) | Iso-hexane (µL) | Toluene (µL) | T (° C.) | Quench value (psi) | yield (g) | quench time (s) | Catalyst Activity (g/mmol · hr) |
|---|---|---|---|---|---|---|---|---|---|---|---|
| PP-1 | 1 | A | 0.080 | 500 | 0 | 4098 | 70 | 15 | 0.0208 | 1800 | 520 |
| PP-2 | 1 | A | 0.080 | 500 | 0 | 4098 | 70 | 15 | 0.0250 | 1801 | 625 |
| PP-3 | 1 | A | 0.080 | 500 | 0 | 4098 | 70 | 15 | 0.0279 | 1803 | 696 |
| PP-4 | 1 | A | 0.080 | 500 | 0 | 4098 | 100 | 15 | 0.0265 | 1802 | 662 |
| PP-5 | 1 | A | 0.080 | 500 | 0 | 4098 | 100 | 15 | 0.0324 | 1803 | 809 |
| PP-6 | 1 | A | 0.080 | 500 | 0 | 4098 | 100 | 15 | 0.0303 | 1801 | 757 |
| PP-7 | 2 | B | 0.025 | 1.1 | 3881 | 218 | 70 | 8 | 0.3328 | 32 | 1,483,690 |
| PP-8 | 2 | B | 0.025 | 1.1 | 3881 | 218 | 70 | 8 | 0.3375 | 32 | 1,504,644 |
| PP-9 | 2 | B | 0.025 | 1.1 | 3881 | 218 | 70 | 8 | 0.3244 | 29 | 1,594,321 |
| PP-10 | 2 | B | 0.025 | 1.1 | 3881 | 218 | 100 | 8 | 0.2274 | 32 | 1,020,112 |
| PP-11 | 2 | B | 0.025 | 1.1 | 3881 | 218 | 100 | 8 | 0.2303 | 32 | 1,033,121 |
| PP-12 | 2 | B | 0.025 | 1.1 | 3881 | 218 | 100 | 8 | 0.2229 | 32 | 1,006,194 |
| PP-13 | 2 | A | 0.025 | 500 | 0 | 4099 | 70 | 8 | 0.2262 | 60 | 544,696 |
| PP-14 | 2 | A | 0.025 | 500 | 0 | 4099 | 70 | 8 | 0.2106 | 67 | 453,309 |
| PP-15 | 2 | A | 0.025 | 500 | 0 | 4099 | 70 | 8 | 0.2332 | 70 | 482,483 |
| PP-16 | 2 | A | 0.025 | 500 | 0 | 4099 | 100 | 8 | 0.1672 | 51 | 469,333 |
| PP-17 | 2 | A | 0.025 | 500 | 0 | 4099 | 100 | 8 | 0.1647 | 55 | 432,000 |
| PP-18 | 2 | A | 0.025 | 500 | 0 | 4099 | 100 | 8 | 0.1624 | 56 | 421,362 |
| PP-19 | 3* | B | 0.030 | 1.1 | 3895 | 205 | 70 | 8 | 0.1427 | 79 | 261,103 |
| PP-20 | 3* | B | 0.030 | 1.1 | 3895 | 205 | 70 | 8 | 0.1365 | 75 | 263,485 |
| PP-21 | 3* | B | 0.030 | 1.1 | 3895 | 205 | 70 | 8 | 0.1346 | 82 | 236,083 |
| PP-22 | 3* | B | 0.030 | 1.1 | 3895 | 205 | 100 | 8 | 0.0682 | 864 | 11,369 |
| PP-23 | 3* | B | 0.030 | 1.1 | 3895 | 205 | 100 | 8 | 0.0514 | 1801 | 4,110 |
| PP-24 | 3* | B | 0.030 | 1.1 | 3895 | 205 | 100 | 8 | 0.0487 | 1800 | 3,896 |
| PP-25 | 3 | A | 0.030 | 500 | 0 | 4099 | 70 | 8 | 0.2150 | 83 | 374,365 |
| PP-26 | 3 | A | 0.030 | 500 | 0 | 4099 | 70 | 8 | 0.2081 | 78 | 383,693 |
| PP-27 | 3 | A | 0.030 | 500 | 0 | 4099 | 70 | 8 | 0.2016 | 77 | 375,555 |
| PP-28 | 3 | A | 0.030 | 500 | 0 | 4099 | 100 | 8 | 0.1413 | 80 | 255,618 |
| PP-29 | 3 | A | 0.030 | 500 | 0 | 4099 | 100 | 8 | 0.1378 | 72 | 274,837 |
| PP-30 | 3 | A | 0.030 | 500 | 0 | 4099 | 100 | 8 | 0.1375 | 78 | 254,826 |
| PP-31 | 4 | A | 0.030 | 500 | 0 | 4099 | 70 | 8 | 0.1650 | 138 | 172,174 |
| PP-32 | 4 | A | 0.030 | 500 | 0 | 4099 | 70 | 8 | 0.1718 | 124 | 200,317 |
| PP-33 | 4 | A | 0.030 | 500 | 0 | 4099 | 70 | 8 | 0.1685 | 129 | 187,802 |
| PP-34 | 4 | A | 0.030 | 500 | 0 | 4099 | 100 | 8 | 0.1174 | 111 | 152,992 |
| PP-35 | 4 | A | 0.030 | 500 | 0 | 4099 | 100 | 8 | 0.1270 | 104 | 176,185 |

TABLE 3a-continued

Propylene polymerization examples - Part 1

| Ex# | Cat ID | Act ID | Cat (μmol) | Act/Cat (molar) | Iso-hexane (μL) | Toluene (μL) | T (° C.) | Quench value (psi) | yield (g) | quench time (s) | Catalyst Activity (g/mmol · hr) |
|---|---|---|---|---|---|---|---|---|---|---|---|
| PP-36 | 4 | A | 0.030 | 500 | 0 | 4099 | 100 | 8 | 0.1231 | 102 | 173,618 |
| PP-37 | 5* | B | 0.040 | 1.1 | 3832 | 268 | 70 | 8 | 0.0541 | 1138 | 4,277 |
| PP-38 | 5* | B | 0.040 | 1.1 | 3832 | 268 | 70 | 8 | 0.0598 | 1801 | 2,988 |
| PP-39 | 5* | B | 0.040 | 1.1 | 3832 | 268 | 70 | 8 | 0.0664 | 1295 | 4,616 |
| PP-40 | 5* | B | 0.040 | 1.1 | 3832 | 268 | 100 | 8 | 0.0058 | 1801 | 290 |
| PP-41 | 5* | B | 0.040 | 1.1 | 3832 | 268 | 100 | 8 | 0.0068 | 1802 | 340 |
| PP-42 | 5* | B | 0.040 | 1.1 | 3832 | 268 | 100 | 8 | 0.0085 | 1802 | 425 |
| PP-43 | 5 | A | 0.030 | 500 | 0 | 4099 | 70 | 8 | 0.0649 | 887 | 10,534 |
| PP-44 | 5 | A | 0.030 | 500 | 0 | 4099 | 70 | 8 | 0.0657 | 1338 | 7,070 |
| PP-45 | 5 | A | 0.030 | 500 | 0 | 4099 | 70 | 8 | 0.0659 | 972 | 9,765 |
| PP-46 | 5 | A | 0.030 | 500 | 0 | 4099 | 100 | 8 | 0.0506 | 1228 | 5,933 |
| PP-47 | 5 | A | 0.030 | 500 | 0 | 4099 | 100 | 8 | 0.0507 | 892 | 8,183 |
| PP-48 | 5 | A | 0.030 | 500 | 0 | 4099 | 100 | 8 | 0.0506 | 956 | 7,620 |
| PP-49 | 6* | B | 0.040 | 1.1 | 3832 | 268 | 70 | 8 | 0.0066 | 1800 | 330 |
| PP-50 | 6* | B | 0.040 | 1.1 | 3832 | 268 | 70 | 8 | 0.0085 | 1801 | 425 |
| PP-51 | 6* | B | 0.040 | 1.1 | 3832 | 268 | 70 | 8 | 0.0081 | 1800 | 405 |
| PP-52 | 6* | B | 0.040 | 1.1 | 3832 | 268 | 100 | 8 | 0.0144 | 1800 | 720 |
| PP-53 | 6* | B | 0.040 | 1.1 | 3832 | 268 | 100 | 8 | 0.0090 | 1565 | 517 |
| PP-54 | 6* | B | 0.040 | 1.1 | 3832 | 268 | 100 | 8 | 0.0169 | 1800 | 845 |
| PP-55 | 6 | A | 0.040 | 500 | 0 | 4099 | 70 | 8 | 0.0726 | 679 | 9,624 |
| PP-56 | 6 | A | 0.040 | 500 | 0 | 4099 | 70 | 8 | 0.0668 | 659 | 9,130 |
| PP-57 | 6 | A | 0.040 | 500 | 0 | 4099 | 70 | 8 | 0.0700 | 693 | 9,091 |
| PP-58 | 6 | A | 0.040 | 500 | 0 | 4099 | 100 | 8 | 0.0588 | 468 | 11,320 |
| PP-59 | 6 | A | 0.040 | 500 | 0 | 4099 | 100 | 8 | 0.0571 | 435 | 11,822 |
| PP-60 | 6 | A | 0.040 | 500 | 0 | 4099 | 100 | 8 | 0.0557 | 434 | 11,551 |
| PP-61 | 7a | A | 0.030 | 500 | 0 | 4099 | 70 | 8 | 0.1090 | 222 | 70,766 |
| PP-62 | 7a | A | 0.030 | 500 | 0 | 4099 | 70 | 8 | 0.1153 | 224 | 74,121 |
| PP-63 | 7a | A | 0.030 | 500 | 0 | 4099 | 70 | 8 | 0.0981 | 184 | 76,732 |
| PP-64 | 7a | A | 0.030 | 500 | 0 | 4099 | 100 | 8 | 0.0917 | 174 | 75,716 |
| PP-65 | 7a | A | 0.030 | 500 | 0 | 4099 | 100 | 8 | 0.0931 | 147 | 90,953 |
| PP-66 | 7a | A | 0.030 | 500 | 0 | 4099 | 100 | 8 | 0.0836 | 181 | 66,400 |
| PP-67 | 7b | A | 0.030 | 500 | 0 | 4099 | 70 | 8 | 0.2236 | 84 | 381,498 |
| PP-68 | 7b | A | 0.030 | 500 | 0 | 4099 | 70 | 8 | 0.1945 | 83 | 339,080 |
| PP-69 | 7b | A | 0.030 | 500 | 0 | 4099 | 70 | 8 | 0.2047 | 75 | 391,458 |
| PP-70 | 7b | A | 0.030 | 500 | 0 | 4099 | 100 | 8 | 0.1409 | 56 | 361,025 |
| PP-71 | 7b | A | 0.030 | 500 | 0 | 4099 | 100 | 8 | 0.1333 | 57 | 334,995 |
| PP-72 | 7b | A | 0.030 | 500 | 0 | 4099 | 100 | 8 | 0.1201 | 55 | 312,738 |
| PP-73 | 8 | A | 0.030 | 500 | 0 | 4099 | 70 | 8 | 0.0578 | 1208 | 6,889 |
| PP-74 | 8 | A | 0.030 | 500 | 0 | 4099 | 70 | 8 | 0.0543 | 1249 | 6,262 |
| PP-75 | 8 | A | 0.030 | 500 | 0 | 4099 | 70 | 8 | 0.0548 | 1285 | 6,140 |
| PP-76 | 8 | A | 0.030 | 500 | 0 | 4099 | 100 | 8 | 0.0499 | 1170 | 6,142 |
| PP-77 | 8 | A | 0.030 | 500 | 0 | 4099 | 100 | 8 | 0.0463 | 888 | 7,505 |
| PP-78 | 8 | A | 0.030 | 500 | 0 | 4099 | 100 | 8 | 0.0466 | 992 | 6,768 |
| PP-79 | 8 | A | 0.040 | 500 | 0 | 4099 | 70 | 8 | 0.0689 | 594 | 10,441 |
| PP-80 | 8 | A | 0.040 | 500 | 0 | 4099 | 70 | 8 | 0.0721 | 693 | 9,359 |
| PP-81 | 8 | A | 0.040 | 500 | 0 | 4099 | 70 | 8 | 0.0713 | 539 | 11,901 |
| PP-82 | 8 | A | 0.040 | 500 | 0 | 4099 | 100 | 8 | 0.0610 | 378 | 14,539 |
| PP-83 | 8 | A | 0.040 | 500 | 0 | 4099 | 100 | 8 | 0.0583 | 363 | 14,447 |
| PP-84 | 8 | A | 0.040 | 500 | 0 | 4099 | 100 | 8 | 0.0541 | 370 | 13,170 |
| PP-85 | 9 | A | 0.030 | 500 | 0 | 4099 | 70 | 8 | 0.1105 | 107 | 149,268 |
| PP-86 | 9 | A | 0.030 | 500 | 0 | 4099 | 70 | 8 | 0.1194 | 120 | 143,042 |
| PP-87 | 9 | A | 0.030 | 500 | 0 | 4099 | 70 | 8 | 0.1016 | 114 | 128,112 |
| PP-88 | 9 | A | 0.030 | 500 | 0 | 4099 | 100 | 8 | 0.1235 | 129 | 138,182 |
| PP-89 | 9 | A | 0.030 | 500 | 0 | 4099 | 100 | 8 | 0.1047 | 115 | 131,560 |
| PP-90 | 9 | A | 0.030 | 500 | 0 | 4099 | 100 | 8 | 0.1300 | 114 | 164,644 |
| PP-91 | 10* | B | 0.030 | 1.1 | 3874 | 226 | 70 | 8 | 0.0091 | 1800 | 607 |
| PP-92 | 10* | B | 0.030 | 1.1 | 3874 | 226 | 70 | 8 | 0.0246 | 1802 | 1,638 |
| PP-93 | 10* | B | 0.030 | 1.1 | 3874 | 226 | 70 | 8 | 0.0119 | 1800 | 793 |
| PP-94 | 10* | B | 0.030 | 1.1 | 3874 | 226 | 100 | 8 | 0.0000 | 1802 | 0 |
| PP-95 | 10* | B | 0.030 | 1.1 | 3874 | 226 | 100 | 8 | 0.0000 | 1800 | 0 |
| PP-96 | 10* | B | 0.030 | 1.1 | 3874 | 226 | 100 | 8 | 0.0000 | 1801 | 0 |
| PP-97 | 10 | A | 0.030 | 500 | 0 | 4099 | 70 | 8 | 0.0474 | 1802 | 3,787 |
| PP-98 | 10 | A | 0.030 | 500 | 0 | 4099 | 70 | 8 | 0.0428 | 1802 | 3,421 |
| PP-99 | 10 | A | 0.030 | 500 | 0 | 4099 | 70 | 8 | 0.0398 | 1800 | 3,183 |
| PP-100 | 10 | A | 0.050 | 500 | 0 | 4099 | 70 | 8 | 0.0660 | 599 | 7,936 |
| PP-101 | 10 | A | 0.050 | 500 | 0 | 4099 | 70 | 8 | 0.0702 | 668 | 7,568 |
| PP-102 | 10 | A | 0.050 | 500 | 0 | 4099 | 70 | 8 | 0.0680 | 604 | 8,102 |
| PP-103 | 10 | A | 0.030 | 500 | 0 | 4099 | 100 | 8 | 0.0362 | 1801 | 2,894 |
| PP-104 | 10 | A | 0.030 | 500 | 0 | 4099 | 100 | 8 | 0.0441 | 1801 | 3,527 |
| PP-105 | 10 | A | 0.030 | 500 | 0 | 4099 | 100 | 8 | 0.0410 | 1800 | 3,279 |
| PP-106 | 10 | A | 0.050 | 500 | 0 | 4099 | 100 | 8 | 0.0652 | 443 | 10,592 |
| PP-107 | 10 | A | 0.050 | 500 | 0 | 4099 | 100 | 8 | 0.0622 | 475 | 9,428 |
| PP-108 | 10 | A | 0.050 | 500 | 0 | 4099 | 100 | 8 | 0.0644 | 464 | 10,000 |
| PP-109 | 11 | A | 0.080 | 500 | 0 | 4098 | 70 | 15 | 0.1263 | 789 | 7,201 |

TABLE 3a-continued

Propylene polymerization examples - Part 1

| Ex# | Cat ID | Act ID | Cat (μmol) | Act/Cat (molar) | Iso-hexane (μL) | Toluene (μL) | T (° C.) | Quench value (psi) | yield (g) | quench time (s) | Catalyst Activity (g/mmol · hr) |
|---|---|---|---|---|---|---|---|---|---|---|---|
| PP-110 | 11 | A | 0.080 | 500 | 0 | 4098 | 70 | 15 | 0.1276 | 708 | 8,113 |
| PP-111 | 11 | A | 0.080 | 500 | 0 | 4098 | 70 | 15 | 0.1349 | 841 | 7,222 |
| PP-112 | 11 | A | 0.080 | 500 | 0 | 4098 | 100 | 15 | 0.1055 | 1273 | 3,729 |
| PP-113 | 11 | A | 0.080 | 500 | 0 | 4098 | 100 | 15 | 0.0961 | 1301 | 3,323 |
| PP-114 | 11 | A | 0.080 | 500 | 0 | 4098 | 100 | 15 | 0.0956 | 1294 | 3,324 |
| PP-115 | 12* | B | 0.080 | 1.1 | 3776 | 323 | 70 | 8 | 0.0006 | 1801 | 15 |
| PP-116 | 12* | B | 0.080 | 1.1 | 3776 | 323 | 70 | 8 | 0.0010 | 1801 | 25 |
| PP-117 | 12* | B | 0.080 | 1.1 | 3776 | 323 | 70 | 8 | 0.0005 | 1802 | 12 |
| PP-118 | 12* | B | 0.080 | 1.1 | 3776 | 323 | 100 | 8 | 0.0029 | 1802 | 72 |
| PP-119 | 12* | B | 0.080 | 1.1 | 3776 | 323 | 100 | 8 | 0.0018 | 1800 | 45 |
| PP-120 | 12* | B | 0.080 | 1.1 | 3776 | 323 | 100 | 8 | 0.0006 | 1802 | 15 |
| PP-121 | 12 | A | 0.040 | 500 | 0 | 4099 | 70 | 8 | 0.0044 | 1800 | 220 |
| PP-122 | 12 | A | 0.040 | 500 | 0 | 4099 | 70 | 8 | 0.0033 | 1801 | 165 |
| PP-123 | 12 | A | 0.040 | 500 | 0 | 4099 | 70 | 8 | 0.0038 | 1800 | 190 |
| PP-124 | 12 | A | 0.040 | 500 | 0 | 4099 | 100 | 8 | 0.0130 | 1802 | 649 |
| PP-125 | 12 | A | 0.040 | 500 | 0 | 4099 | 100 | 8 | 0.0105 | 1801 | 525 |
| PP-126 | 12 | A | 0.040 | 500 | 0 | 4099 | 100 | 8 | 0.0155 | 1803 | 774 |
| PP-126 | 12 | A | 0.040 | 500 | 0 | 4099 | 100 | 8 | 0.0155 | 1803 | 774 |
| C-28 | CB | A | 0.030 | 500 | 0 | 4099 | 70 | 8 | 0.0831 | 162 | 74,095 |
| C-29 | CB | A | 0.030 | 500 | 0 | 4099 | 70 | 8 | 0.1075 | 176 | 88,205 |
| C-30 | CB | A | 0.030 | 500 | 0 | 4099 | 70 | 8 | 0.0871 | 154 | 81,233 |
| C-31 | CB | A | 0.030 | 500 | 0 | 4099 | 100 | 8 | 0.0716 | 125 | 82,814 |
| C-32 | CB | A | 0.030 | 500 | 0 | 4099 | 100 | 8 | 0.0712 | 134 | 76,743 |
| C-33 | CB | A | 0.030 | 500 | 0 | 4099 | 100 | 8 | 0.0757 | 139 | 78,310 |
| C-34 | CC | A | 0.030 | 500 | 0 | 4099 | 70 | 8 | 0.0408 | 1801 | 3,263 |
| C-35 | CC | A | 0.030 | 500 | 0 | 4099 | 70 | 8 | 0.0409 | 1801 | 3,271 |
| C-36 | CC | A | 0.030 | 500 | 0 | 4099 | 70 | 8 | 0.0379 | 1801 | 3,031 |
| C-37 | CC | A | 0.040 | 500 | 0 | 4099 | 70 | 8 | 0.0513 | 1121 | 4,117 |
| C-38 | CC | A | 0.040 | 500 | 0 | 4099 | 70 | 8 | 0.0533 | 1396 | 3,436 |
| C-39 | CC | A | 0.040 | 500 | 0 | 4099 | 70 | 8 | 0.0582 | 1366 | 3,835 |
| C-40 | CC | A | 0.030 | 500 | 0 | 4099 | 100 | 8 | 0.0233 | 1800 | 1,864 |
| C-41 | CC | A | 0.030 | 500 | 0 | 4099 | 100 | 8 | 0.0329 | 1801 | 2,631 |
| C-42 | CC | A | 0.030 | 500 | 0 | 4099 | 100 | 8 | 0.0341 | 1801 | 2,727 |
| C-43 | CC | A | 0.040 | 500 | 0 | 4099 | 100 | 8 | 0.0538 | 1067 | 4,539 |
| C-44 | CC | A | 0.040 | 500 | 0 | 4099 | 100 | 8 | 0.0532 | 968 | 4,947 |
| C-45 | CC | A | 0.040 | 500 | 0 | 4099 | 100 | 8 | 0.0548 | 1026 | 4,808 |

T is the polymerization temperature in ° C.

TABLE 3b

Propylene polymerization examples - Part 2

| Exp# | Cat ID | Act ID | Mn | Mw | Mw/Mn | $T_m$ (° C.) |
|---|---|---|---|---|---|---|
| PP-1 | 1 | A | 2,369 | 3,417 | 1.44 | — |
| PP-2 | 1 | A | 2,376 | 3,470 | 1.46 | — |
| PP-3 | 1 | A | 2,434 | 3,541 | 1.45 | — |
| PP-4 | 1 | A | 1,659 | 1,981 | 1.19 | — |
| PP-5 | 1 | A | 1,691 | 2,011 | 1.19 | — |
| PP-6 | 1 | A | 1,640 | 1,935 | 1.18 | — |
| PP-7 | 2 | B | 23,401 | 54,985 | 2.35 | 149.8 |
| PP-8 | 2 | B | 19,354 | 50,984 | 2.63 | 148.4 |
| PP-9 | 2 | B | 23,683 | 55,186 | 2.33 | 149.6 |
| PP-10 | 2 | B | 8,953 | 19,107 | 2.13 | 141.5 |
| PP-11 | 2 | B | 8,041 | 17,982 | 2.24 | 141.5 |
| PP-12 | 2 | B | 7,713 | 16,692 | 2.16 | 139.3 |
| PP-13 | 2 | A | 42,131 | 67,261 | 1.60 | 146.5 |
| PP-14 | 2 | A | 51,899 | 80,507 | 1.55 | 147.3 |
| PP-15 | 2 | A | 48,460 | 76,365 | 1.58 | 147.0 |
| PP-16 | 2 | A | 16,854 | 25,200 | 1.50 | 132.5 |
| PP-17 | 2 | A | 16,379 | 24,499 | 1.50 | 140.4 |
| PP-18 | 2 | A | 18,187 | 26,723 | 1.47 | 142.2 |
| PP-19 | 3* | B | 98,344 | 146,415 | 1.49 | 156.3 |
| PP-20 | 3* | B | 104,521 | 157,164 | 1.5 | 156.0 |
| PP-21 | 3* | B | 108,375 | 161,653 | 1.49 | 156.3 |
| PP-22 | 3* | B | 35,254 | 49,453 | 1.4 | 147.2 |
| PP-23 | 3* | B | 37,173 | 52,225 | 1.4 | 147.3 |
| PP-24 | 3* | B | 35,869 | 50,396 | 1.4 | 147.5 |
| PP-25 | 3 | A | 60,925 | 93,818 | 1.54 | 153.0 |
| PP-26 | 3 | A | 65,097 | 99,138 | 1.52 | 148.2 |
| PP-27 | 3 | A | 62,795 | 96,529 | 1.54 | 147.5 |
| PP-28 | 3 | A | 23,713 | 34,204 | 1.44 | 143.5 |
| PP-29 | 3 | A | 24,558 | 35,441 | 1.44 | 143.3 |
| PP-30 | 3 | A | 24,069 | 34,608 | 1.44 | 143.7 |
| PP-31 | 4 | A | 121,527 | 180,753 | 1.49 | 151.5 |
| PP-32 | 4 | A | 116,563 | 175,453 | 1.51 | 149.7 |
| PP-33 | 4 | A | 112,342 | 170,594 | 1.52 | 151.0 |
| PP-34 | 4 | A | 37,531 | 56,112 | 1.5 | 147.1 |
| PP-35 | 4 | A | 38,172 | 57,905 | 1.52 | 148.2 |
| PP-36 | 4 | A | 40,190 | 60,083 | 1.49 | 148.9 |
| PP-37 | 5* | B | 45,555 | 96,411 | 2.12 | 147.2 |
| PP-38 | 5* | B | 46,484 | 97,413 | 2.1 | 146.8 |
| PP-39 | 5* | B | 46,263 | 96,866 | 2.09 | 146.9 |
| PP-40 | 5* | B | — | — | — | — |
| PP-41 | 5* | B | — | — | — | — |
| PP-42 | 5* | B | — | — | — | — |
| PP-43 | 5 | A | 71,260 | 128,956 | 1.81 | 146.5 |
| PP-44 | 5 | A | 71,786 | 137,919 | 1.92 | 146.3 |
| PP-45 | 5 | A | 69,132 | 134,983 | 1.95 | 146.7 |
| PP-46 | 5 | A | 25,256 | 42,036 | 1.66 | 136.6 |
| PP-47 | 5 | A | 24,191 | 40,190 | 1.66 | 136.0 |
| PP-48 | 5 | A | 23,756 | 39,754 | 1.67 | 135.6 |
| PP-49 | 6* | B | — | — | — | — |
| PP-50 | 6* | B | — | — | — | — |
| PP-51 | 6* | B | — | — | — | — |
| PP-52 | 6* | B | 2,016 | 2,358 | 1.17 | 131.7 |

TABLE 3b-continued

Propylene polymerization examples - Part 2

| Exp# | Cat ID | Act ID | Mn | Mw | Mw/Mn | $T_m$ (° C.) |
|---|---|---|---|---|---|---|
| PP-53 | 6* | B | — | — | — | — |
| PP-54 | 6* | B | 2,072 | 2,668 | 1.29 | 131.5 |
| PP-55 | 6 | A | 20,549 | 241,965 | 11.77 | — |
| PP-56 | 6 | A | 27,799 | 318,139 | 11.44 | — |
| PP-57 | 6 | A | 31,287 | 350,425 | 11.2 | — |
| PP-58 | 6 | A | 9,170 | 66,394 | 7.24 | — |
| PP-59 | 6 | A | 7,885 | 55,242 | 7.01 | — |
| PP-60 | 6 | A | 8,242 | 60,659 | 7.36 | — |
| PP-61 | 7a | A | 51,071 | 127,803 | 2.5 | 152.1 |
| PP-62 | 7a | A | 45,182 | 108,582 | 2.4 | 150.2 |
| PP-63 | 7a | A | 51,968 | 132,231 | 2.54 | 150.9 |
| PP-64 | 7a | A | 19,400 | 35,884 | 1.85 | 144.8 |
| PP-65 | 7a | A | 18,462 | 34,147 | 1.85 | 144.8 |
| PP-66 | 7a | A | 18,458 | 34,532 | 1.87 | 144.9 |
| PP-67 | 7b | A | 75,641 | 125,826 | 1.66 | 152.9 |
| PP-68 | 7b | A | 88,326 | 142,421 | 1.61 | 152.8 |
| PP-69 | 7b | A | 84,516 | 136,239 | 1.61 | 153.8 |
| PP-70 | 7b | A | 31,088 | 46,418 | 1.49 | 147.3 |
| PP-71 | 7b | A | 27,657 | 41,684 | 1.51 | 146.7 |
| PP-72 | 7b | A | 29,785 | 43,966 | 1.48 | 147.0 |
| PP-73 | 8 | A | 24,381 | 41,770 | 1.71 | 150.0 |
| PP-74 | 8 | A | 29,401 | 48,039 | 1.63 | 150.1 |
| PP-75 | 8 | A | 25,676 | 44,121 | 1.72 | 150.4 |
| PP-76 | 8 | A | 4,413 | 6,794 | 1.54 | 140.6 |
| PP-77 | 8 | A | 4,298 | 6,671 | 1.55 | 139.2 |
| PP-78 | 8 | A | 3,969 | 6,209 | 1.56 | 140.2 |
| PP-79 | 8 | A | 21,444 | 38,635 | 1.8 | 150.2 |
| PP-80 | 8 | A | 24,352 | 41,477 | 1.7 | 150.9 |
| PP-81 | 8 | A | 23,683 | 40,944 | 1.73 | 150.4 |
| PP-82 | 8 | A | 4,151 | 6,458 | 1.56 | 140.3 |
| PP-83 | 8 | A | 4,098 | 6,300 | 1.54 | 138.9 |
| PP-84 | 8 | A | 3,712 | 5,592 | 1.51 | 139.5 |
| PP-85 | 9 | A | 103,751 | 142,605 | 1.37 | 148.4 |
| PP-86 | 9 | A | 100,530 | 138,955 | 1.38 | 148.2 |
| PP-87 | 9 | A | 101,645 | 139,548 | 1.37 | 148.0 |
| PP-88 | 9 | A | 24,918 | 34,774 | 1.4 | 141.1 |
| PP-89 | 9 | A | 25,328 | 35,063 | 1.38 | 140.5 |
| PP-90 | 9 | A | 25,192 | 35,272 | 1.4 | 140.4 |
| PP-91 | 10* | B | — | — | — | — |
| PP-92 | 10* | B | 98,962 | 174,084 | 1.76 | 151.8 |
| PP-93 | 10* | B | 89,066 | 156,410 | 1.76 | 152.2 |
| PP-94 | 10* | B | — | — | — | — |
| PP-95 | 10* | B | — | — | — | — |
| PP-96 | 10* | B | — | — | — | — |
| PP-97 | 10 | A | 65,468 | 103,481 | 1.58 | 153.0 |
| PP-98 | 10 | A | 72,810 | 113,880 | 1.56 | 153.3 |
| PP-99 | 10 | A | 68,412 | 107,999 | 1.58 | 152.7 |
| PP-100 | 10 | A | 52,508 | 78,658 | 1.5 | 150.6 |
| PP-101 | 10 | A | 63,903 | 94,221 | 1.47 | 151.9 |
| PP-102 | 10 | A | 57,334 | 84,281 | 1.47 | 151.4 |
| PP-103 | 10 | A | 14,855 | 24,472 | 1.65 | 142.9 |
| PP-104 | 10 | A | 15,016 | 24,987 | 1.66 | 142.8 |
| PP-105 | 10 | A | 13,348 | 22,419 | 1.68 | 142.4 |
| PP-106 | 10 | A | 14,456 | 21,744 | 1.5 | 141.3 |
| PP-107 | 10 | A | 13,889 | 20,847 | 1.5 | 142.2 |
| PP-108 | 10 | A | 13,614 | 20,798 | 1.53 | 141.7 |
| PP-109 | 11 | A | 240,608 | 378,015 | 1.57 | — |
| PP-110 | 11 | A | 260,847 | 414,692 | 1.59 | — |
| PP-111 | 11 | A | 242,280 | 389,386 | 1.61 | — |
| PP-112 | 11 | A | 63,741 | 100,528 | 1.58 | — |
| PP-113 | 11 | A | 57,731 | 90,242 | 1.56 | — |
| PP-114 | 11 | A | 61,619 | 94,824 | 1.54 | — |
| PP-115 | 12* | B | — | — | — | — |
| PP-116 | 12* | B | — | — | — | — |
| PP-117 | 12* | B | — | — | — | — |
| PP-118 | 12* | B | — | — | — | — |
| PP-119 | 12* | B | — | — | — | — |
| PP-120 | 12* | B | — | — | — | — |
| PP-121 | 12 | A | — | — | — | — |
| PP-122 | 12 | A | — | — | — | — |
| PP-123 | 12 | A | — | — | — | — |
| PP-124 | 12 | A | 5,023 | 17,676 | 3.52 | 132.9 |
| PP-125 | 12 | A | 3,861 | 7,624 | 1.97 | — |
| PP-126 | 12 | A | 4,037 | 7,999 | 1.98 | — |
| C-28 | CB | A | 72,417 | 103,663 | 1.43 | 143.5 |
| C-29 | CB | A | 72,911 | 107,306 | 1.47 | 143.3 |
| C-30 | CB | A | 72,449 | 104,518 | 1.44 | 143.3 |
| C-31 | CB | A | 18,609 | 26,172 | 1.41 | 134.0 |
| C-32 | CB | A | 17,468 | 25,677 | 1.47 | 134.6 |
| C-33 | CB | A | 18,241 | 25,266 | 1.39 | 133.6 |
| C-34 | CC | A | 71,643 | 106,093 | 1.48 | 149.7 |
| C-35 | CC | A | 83,262 | 124,778 | 1.5 | 150.5 |
| C-36 | CC | A | 77,423 | 120,414 | 1.56 | 150.0 |
| C-37 | CC | A | 55,638 | 87,066 | 1.56 | 150.7 |
| C-38 | CC | A | 42,485 | 67,921 | 1.6 | 150.0 |
| C-39 | CC | A | 56,639 | 90,914 | 1.61 | 150.5 |
| C-40 | CC | A | 22,912 | 33,633 | 1.47 | 143.9 |
| C-41 | CC | A | 23,497 | 34,715 | 1.48 | 143.4 |
| C-42 | CC | A | 24,694 | 36,270 | 1.47 | 143.4 |
| C-43 | CC | A | 16,990 | 25,991 | 1.53 | 143.8 |
| C-44 | CC | A | 17,327 | 26,356 | 1.52 | 144.0 |
| C-45 | CC | A | 16,488 | 25,228 | 1.53 | 144.4 |

TABLE 4

$^{13}C$ NMR data for select polypropylene examples

| Ex# | Cat ID | Act ID | m | r | mmmm | mmmr | rmmr | mmrr | mmrm + rmrr |
|---|---|---|---|---|---|---|---|---|---|
| PP-8 | 2 | B | 0.9841 | 0.0159 | 0.9299 | 0.0126 | 0.0366 | 0.0038 | 0.0026 |
| PP-10 | 2 | B | 0.9599 | 0.0401 | 0.8716 | 0.0550 | 0.0187 | 0.0106 | 0.0105 |
| PP-13 | 2 | A | 0.9827 | 0.0173 | 0.9542 | 0.0183 | 0.0023 | 0.0110 | 0.0019 |
| PP-16 | 2 | A | 0.9617 | 0.0383 | 0.9166 | 0.0285 | 0.0054 | 0.0157 | 0.0013 |
| PP-19 | 3* | B | 0.9867 | 0.0133 | 0.9275 | 0.0415 | 0.0142 | 0.0040 | 0.0012 |
| **PP-22, 23, 24 | 3* | B | 0.9632 | 0.0368 | 0.8657 | 0.0620 | 0.0218 | 0.0090 | 0.0055 |
| **PP-26 | 3 | A | 0.9812 | 0.0188 | 0.9499 | 0.0199 | 0.0023 | 0.0115 | 0.0054 |
| **PP-28 | 3 | A | 0.9573 | 0.0427 | 0.9094 | 0.0301 | 0.0019 | 0.0188 | 0.0113 |
| **PP-79, 80, 81 | 8 | A | 0.8776 | 0.1224 | 0.6893 | 0.0999 | 0.0260 | 0.0080 | 0.0789 |
| **PP-85, 87 | 9 | A | 0.9035 | 0.0965 | 0.7780 | 0.0580 | 0.0278 | 0.0052 | 0.0410 |
| **PP-88, 89 | 9 | A | 0.9452 | 0.0548 | 0.8556 | 0.0522 | 0.0136 | 0.0035 | 0.0275 |
| **PP-100, 101, 102 | 10 | A | 0.9719 | 0.0281 | 0.9280 | 0.0261 | 0.0074 | 0.0049 | 0.0099 |
| **PP-106, 107, 108 | 10 | A | 0.9397 | 0.0603 | 0.8399 | 0.0353 | 0.0367 | 0.0268 | 0.0160 |

TABLE 4-continued

¹³C NMR data for select polypropylene examples

| | | | | | | | | |
|---|---|---|---|---|---|---|---|---|
| **PP-109, 110, 111 | 11 | A | 0.4577 | 0.5423 | 0.0647 | 0.1112 | 0.0556 | 0.1597 | 0.199 |
| **PP-112, 113, 114 | 11 | A | 0.4053 | 0.5947 | 0.0326 | 0.0803 | 0.0554 | 0.1302 | 0.222 |
| **C-28, 29, 30 | CB | A | 0.7549 | 0.2451 | 0.506 | 0.0788 | 0.0397 | 0.0714 | 0.1244 |
| **C-31, 32, 33 | CB | A | 0.7768 | 0.2232 | 0.5385 | 0.0905 | 0.0353 | 0.0633 | 0.1082 |
| **C-37, 38, 39 | CC | A | 0.9691 | 0.0309 | 0.9037 | 0.0461 | 0.0107 | 0.0020 | 0.0069 |

| Ex# | mmrm | rrrr | mrrr | mrmm | stereo defects/ 10000 monomer | 2,1-regio (e) defects/ 10000 monomer | 1,3 regio defects/ 10000 monomer | ave. meso run length |
|---|---|---|---|---|---|---|---|---|
| PP-8 | 0.0037 | 0.0019 | 0.0003 | 0.0087 | 49 | 10 | 19 | 127.4 |
| PP-10 | 0.0081 | 0.0044 | 0.0020 | 0.0191 | 142 | 5 | 30 | 56.6 |
| PP-13 | 0.0030 | 0.0030 | 0.0002 | 0.0061 | 78 | 16 | 23 | 85.8 |
| PP-16 | 0.0054 | 0.0093 | 0.0020 | 0.0157 | 110 | 0 | 39 | 66.9 |
| PP-19 | 0.0019 | 0.0033 | 0.0024 | 0.0041 | 35 | 16 | 5 | 178.3 |
| **PP-22, 23, 24 | 0.0128 | 0.0084 | 0.0019 | 0.0128 | 136 | 0 | 0 | 73.5 |
| **PP-26 | 0.0015 | 0.0038 | 0.0004 | 0.0054 | 91 | 0 | 15 | 93.8 |
| **PP-28 | 0.0019 | 0.0075 | 0.0004 | 0.0188 | 160 | 0 | 0 | 62.6 |
| **PP-79, 80, 81 | 0.0380 | 0.0180 | 0.0160 | 0.0260 | 611 | 0 | 24 | 15.8 |
| **PP-85, 87 | 0.0331 | 0.0151 | 0.0203 | 0.0215 | 393 | 40 | 7 | 22.8 |
| **PP-88, 89 | 0.0165 | 0.0064 | 0.0100 | 0.0147 | 231 | 39 | 41 | 32.2 |
| **PP-100, 101, 102 | 0.0059 | 0.0069 | 0.0015 | 0.0094 | 104 | 0 | 0 | 96.5 |
| **PP-106, 107, 108 | 0.0127 | 0.0088 | 0.0110 | 0.0127 | 275 | 0 | 18 | 34.1 |
| **PP-109, 110, 111 | 0.0937 | 0.0917 | 0.1268 | 0.0976 | 2262 | 0 | 0 | 4.4 |
| **PP-112, 113, 114 | 0.1218 | 0.107 | 0.1529 | 0.0977 | 2370 | 0 | 0 | 4.2 |
| **C-28, 29, 30 | 0.0651 | 0.026 | 0.0534 | 0.0352 | 1294 | 41 | 0 | 7.5 |
| **C-31, 32, 33 | 0.0537 | 0.028 | 0.0457 | 0.0369 | 1126 | 0 | 0 | 8.9 |
| **C-37, 38, 39 | 0.0085 | 0.0056 | 0.0048 | 0.0118 | 85 | 24 | 18 | 78.7 |

**The following polymer samples were mixed for ¹³C NMR analysis: PP-22, 23, 24; PP-79, 80, 81; PP-85, 87; PP-88, 89; PP100, 101, 102: PP-106, 107, 108; PP-109, 110, 111; PP-112, 113, 114; C-28, 29, 30; C-31, 32, 33; C37, 38, 39.

All documents described herein are incorporated by reference herein, including any priority documents and/or testing procedures to the extent they are not inconsistent with this text, provided however that any priority document not named in the initially filed application or filing documents is not incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

We claim:

1. A metallocene compound represented by the formula (2):

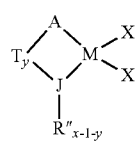

wherein:

M is a group 3, 4, 5 or 6 transition metal atom, or a lanthanide metal atom, or actinide metal atom;

A is a substituted monocyclic or polycyclic ligand that is pi-bonded to M and is substituted with at least one cyclopropyl substituent directly bonded to any sp² carbon atom at a bondable ring position of the ligand;

wherein the cyclopropyl substituent is represented by the formula:

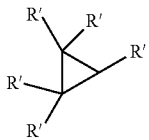

wherein each R' is, independently, hydrogen, a substituted hydrocarbyl group, an unsubstituted hydrocarbyl group, or a halogen;

T is an optional bridging group that is bonded to A and J, and is present when y is one and absent when y is zero;

y is zero or one;

J is a heteroatom with a coordination number of three from group 15 or with a coordination number of two from group 16 of the Periodic Table of Elements;

R" is selected from a $C_1$-$C_{100}$ substituted or unsubstituted hydrocarbyl radical;

x is the coordination number of the heteroatom J where "x-1-y" indicates the number of R" substituents bonded to J; and each X is a univalent anionic ligand, or two Xs are joined and bound to the metal atom to form a metallocycle ring, or two Xs are joined to form a chelating ligand, a diene ligand, or an alkylidene ligand.

2. The metallocene compound of claim 1, wherein A is a monocyclic ligand and is selected from the group consisting of substituted cyclopentadienyl, heterocyclopentadienyl, and heterophenyl ligands.

3. The metallocene compound of claim 1, wherein A is a polycyclic ligand and is selected from the group consisting of substituted indenyl, fluorenyl, cyclopenta[a]naphthyl, cyclopenta[b]naphthyl, heteropentalenyl, heterocylopentapentalenyl, heteroindenyl, heterofluorenyl, heterocyclopentanaphthyl, heterocyclopentaindenyl, and heterobenzocyclopentaindenyl ligands.

4. The metallocene compound of claim 1, wherein M is a group 4 metal and T is represented by the formula, $(R'''_2G)_g$, where each G is C, Si, or Ge, g is 1 or 2, and each R''' is, independently, hydrogen, halogen, $C_1$ to $C_{20}$ hydrocarbyl or a $C_1$ to $C_{20}$ substituted hydrocarbyl, and two or more R''' can form a cyclic structure including aromatic, partially saturated, or saturated cyclic or fused ring system.

5. The metallocene compound of claim 1, wherein A is a substituted indenyl ligand, optionally substituted with one or more cyclopropyl substituents in the 2 and/or 4 positions.

6. The metallocene compound of claim 1, wherein J is nitrogen, phosphorus, oxygen or sulfur.

7. A metallocene compound represented by one of the following formulae:

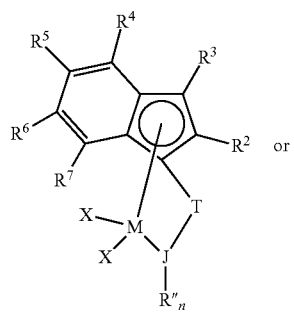

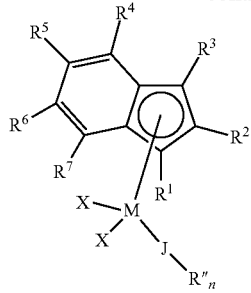

wherein:

M is a transition metal atom selected from group 3, 4, or 5 of the Periodic Table of Elements;

T is a bridging group;

J is a heteroatom with a coordination number of three from group 15 or a heteroatom with a coordination number of two from group 16 of the Periodic Table of Elements;

n represents the number of R" substituents, and n is one when J is a group 15 heteroatom and T is present, or a group 16 heteroatom and T is absent; n is two when J is a group 15 heteroatom and T is absent; n is zero when J is a group 16 heteroatom and T is present;

R" is selected from a $C_1$-$C_{100}$ substituted or unsubstituted hydrocarbyl radical;

each X is a univalent anionic ligand, or two X groups are joined and bound to the metal atom to form a metallocycle ring, or two X groups are joined to form a chelating ligand, a diene ligand, or an alkylidene ligand;

each $R^1$, $R^2$, $R^3$, $R^4$, $R^5$, $R^6$, and $R^7$ is, independently, hydrogen, a substituted hydrocarbyl group, an unsubstituted hydrocarbyl group, or a halide, provided that at least one of $R^1$, $R^2$, $R^3$, $R^4$, $R^5$, $R^6$, and $R^7$ is a cyclopropyl substituent;

provided that any adjacent $R^1$ to $R^7$ groups that are not a cyclopropyl substituent may form a fused ring or multicenter fused ring system where the rings may be aromatic, partially saturated or saturated.

8. The metallocene compound of claim 7, wherein M is hafnium, zirconium or titanium and T is represented by the formula, $(R'''_2G)_g$, where each G is C, Si, or Ge, g is 1 or 2, and each R''' is, independently, hydrogen, halogen, $C_1$ to $C_{20}$ hydrocarbyl or a $C_1$ to $C_{20}$ substituted hydrocarbyl, and two or more R''' can form a cyclic structure including aromatic, partially saturated, or saturated cyclic or fused ring system.

9. The metallocene compound of claim 7, wherein $R^2$ and/or $R^4$ are cyclopropyl substituents.

10. The metallocene compound of claim 7, wherein J is nitrogen, phosphorus, oxygen or sulfur.

11. The metallocene compound of claim 8, wherein when one $R^1$, $R^2$, $R^3$, $R^4$, $R^5$, $R^6$, and $R^7$ is a cyclopropyl substituent, at least one of the other $R^1$ to $R^7$ substitutents is not hydrogen.

12. A metallocene catalyst compound selected from the group consisting of:
dimethylsilylene-(2-cyclopropylindenyl)(tert-butylamido)zirconium dichloride;
dimethylsilylene-(2-cyclopropylindenyl)(tert-butylamido)titanium dichloride;
where, in alternate embodiments, the dichloride in any of the compounds listed above may be replaced with dialkyl, dialkaryl, diflouride, diiodide, or dibromide, or a combination thereof.

13. The metallocene compound of claim 1, wherein each X is independently selected from halides and $C_1$ to $C_5$ alkyl groups.

14. The metallocene compound of claim 1, wherein each X is a methyl group.

15. The metallocene compound of claim 1, wherein A is a monocyclic ligand selected from the group consisting of substituted or unsubstituted cyclopentadienyl, heterocyclopentadienyl, and heterophenyl ligands.

16. The metallocene compound of claim 1, wherein M is a group 4 metal.

17. The metallocene compound of claim 1, wherein each R' is hydrogen.

18. The metallocene compound of claim 1, wherein A is a substituted or unsubstituted indenyl ligand.

19. The metallocene compound of claim 1, wherein A is a substituted indenyl ligand and the indenyl ligand is substituted with one or more cyclopropyl substituents in the 2 and/or 4 and/or 6 positions.

20. The metallocene compound of claim 1, wherein T is represented by the formula, $(R'''_2G)_g$, where each G is C, Si, or Ge, g is 1 or 2, and each R''' is, independently, hydrogen, halogen, $C_1$ to $C_{20}$ hydrocarbyl or a $C_1$ to $C_{20}$ substituted hydrocarbyl, and two or more R''' can form a cyclic structure including aromatic, partially saturated, or saturated cyclic or fused ring system.

21. The metallocene compound of claim 1, wherein T is $CH_2$, $CH_2CH_2$, $C(CH_3)_2$, $SiMe_2$, $SiPh_2$, $SiMePh$, $Si(CH_2)_3$, $Si(CH_2)_4$, or $Si(CH_2)_5$.

22. A catalyst system comprising activator and the metallocene catalyst compound of claim 1.

23. The catalyst system of claim 22, wherein the activator comprises alumoxane.

24. The catalyst system of claim 22, wherein the activator comprises a non-coordinating anion activator.

25. The catalyst system of claim 22, wherein activator is represented by the formula:

wherein Z is (L-H) or a reducible Lewis Acid, L is an neutral Lewis base; H is hydrogen; (L-H)$^+$ is a Bronsted acid; $A^{d-}$ is a non-coordinating anion having the charge d−; and d is an integer from 1 to 3.

26. The catalyst system of claim 22, wherein the activator is one or more of:
N,N-dimethylanilinium tetrakis(pentafluorophenyl)borate,
triphenylcarbenium tetrakis(pentafluorophenyl)borate,
trimethylammonium tetrakis(perfluoronaphthyl)borate,
triethylammonium tetrakis(perfluoronaphthyl)borate,
tripropylammonium tetrakis(perfluoronaphthyl)borate,
tri(n-butyl)ammonium tetrakis(perfluoronaphthyl)borate,
tri(t-butyl)ammonium tetrakis(perfluoronaphthyl)borate,
N,N-dimethylanilinium tetrakis(perfluoronaphthyl)borate,
N,N-diethylanilinium tetrakis(perfluoronaphthyl)borate,
N,N-dimethyl-(2,4,6-trimethylanilinium) tetrakis(perfluoronaphthyl)borate,
tropillium tetrakis(perfluoronaphthyl)borate,
triphenylcarbenium tetrakis(perfluoronaphthyl)borate,
triphenylphosphonium tetrakis(perfluoronaphthyl)borate,
triethylsilylium tetrakis(perfluoronaphthyl)borate,
benzene(diazonium) tetrakis(perfluoronaphthyl)borate,
trimethylammonium tetrakis(perfluorobiphenyl)borate,
triethylammonium tetrakis(perfluorobiphenyl)borate,
tripropylammonium tetrakis(perfluorobiphenyl)borate,
tri(n-butyl)ammonium tetrakis(perfluorobiphenyl)borate,
tri(t-butyl)ammonium tetrakis(perfluorobiphenyl)borate,
N,N-dimethylanilinium tetrakis(perfluorobiphenyl)borate,
N,N-diethylanilinium tetrakis(perfluorobiphenyl)borate,
N,N-dimethyl-(2,4,6-trimethylanilinium) tetrakis(perfluorobiphenyl)borate,
tropillium tetrakis(perfluorobiphenyl)borate,
triphenylcarbenium tetrakis(perfluorobiphenyl)borate,
triphenylphosphonium tetrakis(perfluorobiphenyl)borate,
triethylsilylium tetrakis(perfluorobiphenyl)borate,
benzene(diazonium) tetrakis(perfluorobiphenyl)borate,
[4-t-butyl-PhNMe$_2$H][(C$_6$F$_3$(C$_6$F$_5$)$_2$)$_4$B],
trimethylammonium tetraphenylborate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl-(2,4,6-trimethylanilinium) tetraphenylborate,
tropillium tetraphenylborate,
triphenylcarbenium tetraphenylborate,
triphenylphosphonium tetraphenylborate,
triethylsilylium tetraphenylborate,
benzene(diazonium)tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl-(2,4,6-trimethylanilinium) tetrakis(pentafluorophenyl)borate,
tropillium tetrakis(pentafluorophenyl)borate,
triphenylcarbenium tetrakis(pentafluorophenyl)borate,
triphenylphosphonium tetrakis(pentafluorophenyl)borate,
triethylsilylium tetrakis(pentafluorophenyl)borate,
benzene(diazonium) tetrakis(pentafluorophenyl)borate,
trimethylammonium tetrakis-(2,3,4,6-tetrafluorophenyl) borate,
triethylammonium tetrakis-(2,3,4,6-tetrafluorophenyl)borate,
tripropylammonium tetrakis-(2,3,4,6-tetrafluorophenyl) borate,
tri(n-butyl)ammonium tetrakis-(2,3,4,6-tetrafluoro-phenyl)borate,
dimethyl(t-butyl)ammonium tetrakis-(2,3,4,6-tetrafluorophenyl)borate,
N,N-dimethylanilinium tetrakis-(2,3,4,6-tetrafluorophenyl)borate,
N,N-diethylanilinium tetrakis-(2,3,4,6-tetrafluorophenyl) borate,
N,N-dimethyl-(2,4,6-trimethylanilinium) tetrakis-(2,3,4,6-tetrafluorophenyl)borate,
tropillium tetrakis-(2,3,4,6-tetrafluorophenyl)borate,
triphenylcarbenium tetrakis-(2,3,4,6-tetrafluorophenyl) borate,
triphenylphosphonium tetrakis-(2,3,4,6-tetrafluorophenyl)borate,
triethylsilylium tetrakis-(2,3,4,6-tetrafluorophenyl)borate,
benzene(diazonium) tetrakis-(2,3,4,6-tetrafluorophenyl) borate, trimethylammonium tetrakis(3,5-bis(trifluoromethyl)phenyl)borate,
triethylammonium tetrakis(3,5-bis(trifluoromethyl)phenyl)borate,
tripropylammonium tetrakis(3,5-bis(trifluoromethyl)phenyl)borate,
tri(n-butyl)ammonium tetrakis(3,5-bis(trifluoromethyl)phenyl)borate,
tri(t-butyl)ammonium tetrakis(3,5-bis(trifluoromethyl)phenyl)borate,
N,N-dimethylanilinium tetrakis(3,5-bis(trifluoromethyl)phenyl)borate,
N,N-diethylanilinium tetrakis(3,5-bis(trifluoromethyl)phenyl)borate,
N,N-dimethyl-(2,4,6-trimethylanilinium) tetrakis(3,5-bis(trifluoromethyl)phenyl)borate,
tropillium tetrakis(3,5-bis(trifluoromethyl)phenyl)borate,
triphenylcarbenium tetrakis(3,5-bis(trifluoromethyl)phenyl)borate,
triphenylphosphonium tetrakis(3,5-bis(trifluoromethyl)phenyl)borate,
triethylsilylium tetrakis(3,5-bis(trifluoromethyl)phenyl)borate,
benzene(diazonium) tetrakis(3,5-bis(trifluoromethyl)phenyl)borate,
di-(i-propyl)ammonium tetrakis(pentafluorophenyl)borate,
dicyclohexylammonium tetrakis(pentafluorophenyl)borate,
tri(o-tolyl)phosphonium tetrakis(pentafluorophenyl)borate,
tri(2,6-dimethylphenyl)phosphonium tetrakis(pentafluorophenyl)borate,
triphenylcarbenium tetrakis(perfluorophenyl)borate,
1-(4-(tris(pentafluorophenyl)borate)-2,3,5,6-tetrafluorophenyl)pyrrolidinium,
4-(tris(pentafluorophenyl)borate)-2,3,5,6-tetrafluoropyridine, and
triphenylcarbenium tetrakis(3,5-bis(trifluoromethyl)phenyl)borate).

27. The catalyst system of claim 22, wherein the catalyst system is supported.

28. The catalyst system of claim 22, wherein the catalyst system comprises two catalyst compounds at least one of which is represented by formula (2):

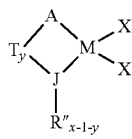

wherein:

M is a group 3, 4, 5 or 6 transition metal atom, or a lanthanide metal atom, or actinide metal atom;

A is a substituted monocyclic or polycyclic ligand that is pi-bonded to M and is substituted with at least one cyclopropyl substituent directly bonded to any $sp^2$ carbon atom at a bondable ring position of the ligand;

wherein the cyclopropyl substituent is represented by the formula:

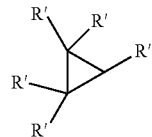

wherein each R' is, independently, hydrogen, a substituted hydrocarbyl group, an unsubstituted hydrocarbyl group, or a halogen;

T is an optional bridging group that is bonded to A and J, and is present when y is one and absent when y is zero;

y is zero or one;

J is a heteroatom with a coordination number of three from group 15 or with a coordination number of two from group 16 of the Periodic Table of Elements;

R" is selected from a $C_1$-$C_{100}$ substituted or unsubstituted hydrocarbyl radical;

x is the coordination number of the heteroatom J where "x-1-y" indicates the number of R" substituents bonded to J; and each X is a univalent anionic ligand, or two Xs are joined and bound to the metal atom to form a metallocycle ring, or two Xs are joined to form a chelating ligand, a diene ligand, or an alkylidene ligand.

29. A catalyst system comprising activator and the metallocene catalyst compound of claim 19.

30. A catalyst system comprising activator and the metallocene catalyst compound of claim 1, where $R^2$ is a cyclopropyl substituent.

31. A process to polymerize olefins comprising contacting one or more olefins with a catalyst system comprising an activator and a compound of claim 1.

32. The process of claim 31, wherein the activator comprises alumoxane.

33. The process of claim 31, wherein the activator comprises a non-coordinating anion activator.

34. The process of claim 31, wherein activator is represented by the formula:

$$(Z)_d^+(A^{d-})$$

wherein Z is (L-H) or a reducible Lewis Acid, L is an neutral Lewis base; H is hydrogen; (L-H)$^+$ is a Bronsted acid; $A^{d-}$ is a non-coordinating anion having the charge d−; and d is an integer from 1 to 3.

35. The process of claim 31, wherein the process occurs at a temperature of from about 0° C. to about 300° C., at a pressure in the range of from about 0.35 MPa to about 10 MPa, and at a time up to 300 minutes.

36. The process of claim 31 further comprising obtaining polymer.

37. The process of claim 31, wherein the olefins comprise ethylene and or propylene.

38. The process of claim 31, wherein a polymer of propylene is obtained.

39. A process to polymerize olefins comprising contacting one or more olefins with a catalyst system comprising an activator and a compound of claim 29.

40. A process to polymerize olefins comprising contacting one or more olefins with a catalyst system comprising an activator and a compound of claim 30.

41. A metallocene compound represented by the formula (2):

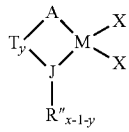

wherein:

M is a group 3, 4, 5 or 6 transition metal atom, or a lanthanide metal atom, or actinide metal atom;

A is a substituted monocyclic or polycyclic ligand substituted with at least one cyclopropyl substituent directly bonded to any $sp^2$ carbon atom at a bondable ring position of the ligand;

wherein the cyclopropyl substituent is represented by the formula:

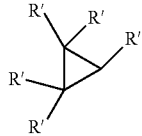

wherein each R' is, independently, hydrogen, a substituted hydrocarbyl group, an unsubstituted hydrocarbyl group, or a halogen;

T is an optional bridging group that is bonded to A and J, and is present when y is one and absent when y is zero;

y is zero or one;

J is a heteroatom with a coordination number of three from group 15 or with a coordination number of two from group 16 of the Periodic Table of Elements;

R" is selected from a $C_1$-$C_{100}$ substituted or unsubstituted hydrocarbyl radical;

x is the coordination number of the heteroatom J where "x-1-y" indicates the number of R" substituents bonded to J; and each X is a univalent anionic ligand, or two Xs are joined and bound to the metal atom to form a metallocycle ring, or two Xs are joined to form a chelating ligand, a diene ligand, or an alkylidene ligand.

42. A catalyst system comprising activator and the metallocene compound of claim 41.

* * * * *